US010781453B2

(12) United States Patent
Heslin et al.

(10) Patent No.: US 10,781,453 B2
(45) Date of Patent: Sep. 22, 2020

(54) NON-HUMAN ANIMALS HAVING A HEXANUCLEOTIDE REPEAT EXPANSION IN A C9ORF72 LOCUS

(71) Applicant: Regeneron Pharmaceuticals, Inc., Tarrytown, NY (US)

(72) Inventors: David Heslin, Closter, NJ (US); Roxanne Ally, Briarwood, NY (US); Chia-Jen Siao, New York, NY (US); Ka-Man Venus Lai, Seattle, WA (US); David M. Valenzuela, Yorktown Heights, NY (US); Aarti Sharma-Kanning, New York, NY (US); Daisuke Kajimura, New York, NY (US); Gustavo Droguett, New City, NY (US); David Frendewey, New York, NY (US); Alexander O. Mujica, Elmsford, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 89 days.

(21) Appl. No.: 15/721,517

(22) Filed: Sep. 29, 2017

(65) Prior Publication Data
US 2018/0094267 A1 Apr. 5, 2018

Related U.S. Application Data

(60) Provisional application No. 62/402,613, filed on Sep. 30, 2016, provisional application No. 62/452,795, filed on Jan. 31, 2017.

(51) Int. Cl.
| | | |
|---|---|---|
| *C12N 15/62* | (2006.01) |
| *A01K 67/027* | (2006.01) |
| *C12N 15/113* | (2010.01) |
| *C12N 15/90* | (2006.01) |
| *C12N 5/0793* | (2010.01) |
| *C12N 5/0797* | (2010.01) |
| *C12N 9/22* | (2006.01) |

(52) U.S. Cl.
CPC ........ *C12N 15/625* (2013.01); *A01K 67/0278* (2013.01); *C12N 5/0619* (2013.01); *C12N 5/0623* (2013.01); *C12N 15/113* (2013.01); *C12N 15/907* (2013.01); *A01K 2217/072* (2013.01); *A01K 2227/105* (2013.01); *A01K 2267/0318* (2013.01); *C12N 9/22* (2013.01); *C12N 2310/20* (2017.05); *C12N 2800/30* (2013.01)

(58) Field of Classification Search
CPC .................................................. C12N 15/625
See application file for complete search history.

(56) References Cited

U.S. PATENT DOCUMENTS

| | | |
|---|---|---|
| 5,670,356 A | 9/1997 | Sherf et al. |
| 5,874,304 A | 2/1999 | Zolotukhin et al. |
| 5,942,435 A | 8/1999 | Wheeler et al. |
| 6,586,251 B2 | 7/2003 | Economides et al. |
| 6,596,541 B2 | 7/2003 | Murphy et al. |
| 7,105,348 B2 | 9/2006 | Murphy et al. |
| 7,294,754 B2 | 11/2007 | Poueymirou et al. |
| 7,576,259 B2 | 8/2009 | Poueymirou et al. |
| 7,612,250 B2 | 11/2009 | Overstrom et al. |
| 7,659,442 B2 | 2/2010 | Poueymirou et al. |
| 8,354,389 B2 | 1/2013 | Frendewey et al. |
| 8,518,392 B2 | 8/2013 | Frendewey et al. |
| 8,697,359 B1 * | 4/2014 | Zhang .................... C12N 15/85 |
| | | 435/6.1 |
| 8,697,851 B2 | 4/2014 | Frendewey et al. |
| 10,285,388 B2 | 5/2019 | Atanasio et al. |
| 10,329,582 B2 | 6/2019 | Lee et al. |
| 10,385,359 B2 | 8/2019 | Lee et al. |
| 10,508,289 B2 | 12/2019 | Duchateau et al. |

(Continued)

FOREIGN PATENT DOCUMENTS

| | | |
|---|---|---|
| WO | 1999/005266 | 2/1999 |
| WO | 2002/036789 | 5/2002 |

(Continued)

OTHER PUBLICATIONS

Chew et al. (Science. 2015; 348(6239): 1151-1154) (Year: 2015).*
Renton et al. (Nature Neuroscience. Jan. 2014; 17(1): 17-23) (Year: 2014).*
Buchman et al. Molecular Neurodegeneration 2013, 8:12, pp. 1-6 (Year: 2013).*
Adams, et al., "A genome-wide, end-sequenced 129Sv BAC library resource for targeting vector construction," Genomics, 86:753-758 (2005).
Almeida S. et al., "Modeling Key Pathological Features of Frontotemporal Dementia with C9ORF72 Repeat Expansion in iPSC-Derived Human Neurons", Acta Neuropathol 126:385-399 (2013).

(Continued)

*Primary Examiner* — Scott Long
(74) *Attorney, Agent, or Firm* — Rita S. Wu; Yongjin Choi; FisherBroyles, LLP

(57) ABSTRACT

A non-human animal (e.g., a rodent) model for diseases associated with a C9ORF72 heterologous hexanucleotide repeat expansion sequence is provided, which non-human animal comprises a heterologous hexanucleotide repeat (GGGGCC) in an endogenous C9ORF72 locus. A non-human animal disclosed herein comprising a heterologous hexanucleotide repeat expansion sequence comprising at least one instance, e.g., repeat, of a hexanucleotide (GGGGCC) sequence may further exhibit a characteristic and/or phenotype associated with one or more neurodegenerative disorders (e.g., amyotrophic lateral sclerosis (ALS) and/or frontotemporal dementia (FTD), etc.). Methods of identifying therapeutic candidates that may be used to prevent, delay or treat one or more neurodegenerative (e.g., amyotrophic lateral sclerosis (ALS, also referred to as Lou Gehrig's disease) and frontotemporal dementia (FTD)) are also provided.

48 Claims, 18 Drawing Sheets
(3 of 18 Drawing Sheet(s) Filed in Color)
Specification includes a Sequence Listing.

(56) References Cited

U.S. PATENT DOCUMENTS

| | | |
|---|---|---|
| 2004/0018626 A1 | 1/2004 | Murphy et al. |
| 2004/0177390 A1 | 9/2004 | Lewis et al. |
| 2005/0144655 A1 | 6/2005 | Economides et al. |
| 2006/0085866 A1 | 4/2006 | Poueymirou et al. |
| 2008/0028479 A1 | 1/2008 | Poueymirou et al. |
| 2008/0078000 A1 | 3/2008 | Poueymirou et al. |
| 2008/0078001 A1 | 3/2008 | Poueymirou et al. |
| 2008/0092249 A1 | 4/2008 | Lewis et al. |
| 2010/0035768 A1 | 2/2010 | Gibson et al. |
| 2013/0309670 A1 | 11/2013 | Frendewey et al. |
| 2014/0178879 A1 | 6/2014 | Economides et al. |
| 2014/0235933 A1 | 8/2014 | Lee et al. |
| 2014/0309487 A1 | 10/2014 | Lee et al. |
| 2014/0310828 A1 | 10/2014 | Lee et al. |
| 2014/0331340 A1 | 11/2014 | Poueymirou et al. |
| 2015/0267197 A1 | 9/2015 | Bennett et al. |
| 2015/0376628 A1 | 12/2015 | Schoenherr et al. |
| 2015/0376651 A1 | 12/2015 | Frendewey et al. |
| 2016/0115486 A1 | 4/2016 | Schoenherr et al. |
| 2016/0145646 A1 | 5/2016 | Frendewey et al. |
| 2016/0177339 A1 | 6/2016 | Voronina et al. |
| 2016/0273002 A1 | 9/2016 | Duchateau et al. |
| 2016/0355796 A1 | 12/2016 | Davidson et al. |
| 2018/0023077 A1 | 1/2018 | Rigo |
| 2018/0100144 A1 | 4/2018 | Buj Bello et al. |
| 2018/0344817 A1 | 12/2018 | Smith et al. |
| 2019/0167814 A1 | 6/2019 | Dion et al. |
| 2019/0167815 A1 | 6/2019 | Holmes et al. |
| 2019/0216062 A1 | 7/2019 | Atanasio et al. |
| 2019/0249230 A1 | 8/2019 | Pederson et al. |
| 2019/0270980 A1 | 9/2019 | Ikeda et al. |

FOREIGN PATENT DOCUMENTS

| | | |
|---|---|---|
| WO | 2006/044962 | 4/2006 |
| WO | 2008/017234 | 2/2008 |
| WO | 2011/020014 | 2/2011 |
| WO | 2013/030588 | 3/2013 |
| WO | 2013/041577 | 3/2013 |
| WO | 2013/163394 | 10/2013 |
| WO | 2014/062736 | 4/2014 |
| WO | 2014/130706 A1 | 8/2014 |
| WO | 2014/172489 A2 | 10/2014 |
| WO | 2015/059265 | 4/2015 |
| WO | 2015/153760 | 10/2015 |
| WO | 2015/200334 | 12/2015 |
| WO | 2015/200805 A2 | 12/2015 |
| WO | 2016/081923 | 5/2016 |
| WO | 2016/100819 | 6/2016 |
| WO | 2016/174056 | 11/2016 |
| WO | 2016/179112 | 11/2016 |
| WO | 2017/109757 | 6/2017 |
| WO | 2017/178590 A1 | 10/2017 |
| WO | 2018/078131 A1 | 5/2018 |
| WO | 2018/078134 A1 | 5/2018 |
| WO | 2018/165541 A1 | 9/2018 |
| WO | 2018/208972 | 11/2018 |
| WO | 2019/084140 | 5/2019 |

OTHER PUBLICATIONS

Altschul, et al., "Basic Local Alignment Search Tool," J. Mol. Biol., 215(3): 403-410 (1990).

Altschul, et al., "Local Alignment Statistics," Methods in Enzymology 460-480 (1997).

Altschul, et al., "Gapped BLAST and PSI-BLAST: a new generation of protein database search programs," Nucleic Acids Res., 25(17):3389-3402 (1997).

Angrand, et al., "Simplified generation of targenting constructs using ET recombination," Nucleic Acids Res. 27(17):e16 (1999).

Atanasio A. et al., "C9orf72 Ablation Causes Immune Dysregulation Characterized by Leukocyte Expansion, Autoantibody Production, and Glomerulonephropathy in Mice", Nature 6:23204 (14 pages) (2016).

Atanasio A. et al., "C9orf72 Ablation Causes Immune Dysregulation Characterized by Leukocyte Expansion, Autoantibody Production, and Glomerulonephropathy in Mice", Nature 6:23204 (11 pages), Supplemental Material (2016).

Atkinson R.A.K. et al., "C9ORF72 Expression and Cellular Localization Over Mouse Development", Acta Neuropathologica Commmunications 3:59 (11 pages) (2015).

Auerbach, et al., "Establishment and Chimera Analysis of 129/SvEv- and C57BL/6-Derived Mouse Embryonic Stem Cell Lines," Biotechniques 29(5):1024-1032 (2000).

Bacchetti, et al., "Transfer of the gene for thymidine kinase to thymidine kinase-deficient human cells by purified herpes simplex viral DNA," Proc. Natl. Acad. Sci. USA 74(4): 1590-1594 (1977).

Beck, et al. "Nucleotide sequence and exact localization of the neomycin phosphotransferase gene from transposon Tn5," Gene 19(3):327-336 (1982).

Bertram "MATra—Magnet Assisted Transfection: Combining Nanotechnology and Magnetic Forces to Improve Intracellular Delivery of Nucleic Acids," Current Pharmaceutical Biotechnology 7(4):277-285 (2006).

Bieniek K.F. et al., "Expanded C9ORF72 Hexanucleotide Repeat in Depressive Pseudodementia", JAMA Neurology 71(6):775-781 (Jun. 2014).

Burberry A. et al., "Loss-of-Function Mutations in the C9ORF72 Mouse Ortholog Cause Fatal Autoimmune Disease", 8(347):1-12 (Jul. 13, 2016).

Chan et al., "RNA-mediated pathogenic mechanism in polyglutamine diseases and amyotrophic lateral sclerosis," Frontiers in Cellular Neuroscience, 8:Figure 6 (2014).

Chew J. et al., "C9ORF72 Repeat Expansions in Mice Cause TDP-43 Pathology, Neuronal Loss, and Behavioral Deficits", Science 348(6239):1151-1154 (Jun. 2015).

Ciura S. et al., "Loss of Function of C9ORF72 Causes Motor Deficits in a Zebrafish Model of Amyotrophic Lateral Sclerosis", Ann Neurol 74:180-187 (Aug. 2013).

Dechiara, et al., 2010, Methods Enzymol. 476:285-294.

Dechiara, et al., "VelociMouse: Fully ES Cell-Derived Fo-Generation Mice Obtained from the Injection of ES Cells into Eight-Cell-Stage Embryos," Methods Mol. Biol. 530:311-324 (2009).

Dejesus-Hernandez M. et al., "Expanded GGGGCC Hexanucleotide Repeat in Noncoding Region of C9ORF72 Causes Chromosome 9p-Linked FTD and ALS", Neuron 72:245-256 (Oct. 20, 2011).

Dennis (2002) "Welfare issues of genetically modified animals," ILAR Journal, 43(2):100-109.

Egawa, et al., "Drug Screening for ALS Using Patient-Specific Induced Pluripotent Stem Cells," Science Translational Medicine, 4(145):145ra104-145ra104Figures 1-4 (2012).

Farg M.A. et al., "C9ORF72, Implicated in Amytrophic Lateral Sclerosis and Frontotemporal Dementia, Regulates Endosomal Trafficking," Human Molecular Genetics 23(13):3579-3595 (2014).

Festing, et al., "Revised nomenclature for strain 129 mice," Mammalian Genome 10:836 (1999).

Frendewey, et al., "The Loss-Of-Allele Assay for ES Cell Screening and Mouse Genotyping," Methods Enzymol., 476:295-307 (2010).

GenBank Accession No. NM_145005.6 (5 pages) (Jul. 9, 2016).
GenBank Accession No. NP_659442.2 (3 pages) (Jul. 9, 2016).
GenBank Accession No. NM_018325.4 (5 pages) (Jul. 9, 2016).
GenBank Accession No. NP_060795.1 (3 pages) (Jul. 9, 2016).
GenBank Accession No. NH_001256054.2 (5 pages) (Jul. 9, 2016).
GenBank Accession No. NP_001242983.1 (3 pages) (Jul. 9, 2016).
GenBank Accession No. NM_001081343.1 (4 pages) (Dec. 12, 2015).
GenBank Accession No. NP_001074812.1 (2 pages) (Dec. 12, 2015).
GenBank Accession No. NM_001007702.1 (3 pages) (Aug. 10, 2014).
GenBank Accession No. NP_001007703.1 (2 pages) (Aug. 10, 2014).

Gibson, et al. "Enzymatic assembly of DNA molecules up to several hundred kilobases," Nature Methods 6(5): 343-345 (2009).

(56) References Cited

OTHER PUBLICATIONS

Gill, et al., "No Benefit from Chronic Lithium Dosing in a Sibling-Matched, Gender Balanced, Investigator-Blinded Trial Using a Standard Mouse Model of Familial ALS," PLoS One, 4(8):e6489 (2009).
Gonnet, et al., "Exhaustive Matching of the Entire Protein," Science, 256:1443-1445.
Graham, et al., "A New Technique for the Assay of Infectivity of Human Adenovirus 5 DNA," Virology, 52(2): 456-467 (1973).
Heutink P. et al., "C9orf72; Abnormal RNA Expression is the Key", Experimental Neurology 262:102-110 (Dec. 2014).
Hukema R.K. et al., "A New Inducible Transgenic Mouse Model for C9orf72-Associated GGGGCC Repeat Expansion Supports a Gain-of-Function Mechanism in C9orf72-Associated ALS and FTD", Acta Neuropathologica Communications 2:166 (4 pages) (2014).
Koppers M. et al., "C9orf72 Ablation in Mice Does Not Cause Motor Neuron Degeneration or Motor Deficits", Ann Neurol 78(3):426-438 (2015).
Lagier-Tourenne C. et al., "Targeted Degradation of Sense and Antisense C9orf72 RNA Foci as Therapy for ALS and Frontotemporal Degeneration", PNAS, pp. E4530-E4539 (Oct. 29, 2013).
Lakso, et al., "Targeted oncogene activation by site-specific recombination in transgenic mice," Proc. Natl. Acad. Sci. USA, 89:6232-6236 (1992).
Liu, et al., "c9orf72 Disease-Related Foci Are Each Composed of One Mutant Expanded Repeat RNA," Cell Chemical Biology, 24:141-148, (2017) http://dx.doi.org/10.1016/j.chembiol.2016.12.018.
Majounie E. et al., "Frequency of the C9orf72 Hexanucleotide Repeat Expansion in Patients With Amyotrophic Lateral Sclerosis and Frontotemporal Dementia: A Cross-Sectional Study", Lancet Neurology 11:323-330 (Apr. 2012).
Menalled, et al., "Knock-In Mouse Models of Huntington's Disease," Journal of the American Society for Experimental NeuroTherapeutics, 2(3):465-470 (2005).
Meyer, et al., "Gene targeting by homologous recombination in mouse zygotes mediated by zinc-finger nucleases," PNAS, 107(34):15022-15026 (2010).
Meyer, et al., "Modeling disease mutations by gene targeting in one-cell mouse embryos," PNAS, 109(24):9354-9359 (2012).
Mori K. et al., "The C9orf72 Ggggcc Repeat is Translated into Aggregating Dipeptide-Repeat Proteins in FTLD/ALS", Science 339(6125):1335-1338 (Mar. 15, 2013).
Muller U., "Ten Years of Gene Targeting: Targeted Mouse Mutants, from Vector Design to Phenotype Analysis", Mechanisms of Development 82:3-21 (1999).
Muyrers, et al., "Rapid modification of bacterial artificial chromosomes by ET-recombination," Nucleic Acids Res. 27(6):1555-1557 (1999).
Narayanan, et al., "Efficient and precise engineering of a 200 kb b-globin human/bacterial artificial chromosome in E. coli DH106 using an inducible homologous recombination system," Gene Ther., 6:442-447 (1999).
O'Gorman, et al, "Recombinase-mediated gene activation and site-specific integration in mammalian cells," Science 251(4999):1351-1355 (1991).
O'Rourke, et al., "C9orf72BAC Transgenic Mice Display Typical Pathologic Features of ALS/FTD," Neuron, 88(5):892-901 (2015).
O'Rourke J.G. et al., "C9orf72 is Required for Proper Macrophage and Microglial Function in Mice", Science 351 (6279):1324-1329 (Mar. 18, 2016).
O'Rourke J.G. et al., "C9orf72 is Required for Proper Macrophage and Microglial Function in Mice", Science 351 (6279):1324-1329, Supplementary Materials (24 pages) (2016).
Panda S.K. et al., "Highly Efficient Targeted Mutagenesis in Mice Using TALENs", Genetics 195:703-713 (Nov. 2013).
Panda S.K. et al., "Highly Efficient Targeted Mutagenesis in Mice Using TALENs", Genetics 195:703-713, Supporting Information (15 pages) (2013).

Picher-Martel, et al., "From animal models to human disease: a genetic approach for personalized medicine in ALS," ATA Neuropathological Communications, 4(1):Table 5 (2016).
Poueymirou, et al., "F0 generation mice fully derived from gene-targeted embryonic stem cels allowing immediate phenotypic analysis," Nat. Biotechnol. 25:91-99 (2007).
Pribadi, et al., "CRISPR-Cas9 targeted deletion of the C9orf72 repeat expansion mutation corrects cellular phenotypes in patient-derived iPS cells," BioRXiv, pp. 13-14; figure 1 (2016) https://www.biorxiv.org/content/biorxiv/early/2016/05/02/051193.full.pdf (retrieved on Nov. 28, 2017).
Renton A.E. et al., "A Hexanucleotide Repeat Expansion in C9ORF72 is the Cause of Chromosome 9p21-Linked ALS-FTD", Neuron 72:257-268 (Oct. 20, 2011).
Renton, et al., "State of play in amyotrophic lateral sclerosis genetics," Nature Neuroscience, 17(1):17-23 (2014).
Robberecht W. et al., "The Changing Scene of Amyotrophic Lateral Sclerosis", Nature Reviews. Neuroscience 14(4):248-264 (Mar. 6, 2013).
Roberson E.D. et al., "Mouse Models of Frontotemporal Dementia", Ann Neurol. 72(6):837-849 (Dec. 2012).
Santerre, et al., "Expression of prokaryotic genes for hygromycin B and G418 resistance as dominant-selection markers in mouse L cells," Gene, 30(1-3):147-156 (1984).
Skarnes W.C. et al., "A Conditional Knockout Resource for the Genome-Wide Study of Mouse Gene Function", Nature 474(7351):337-342 (2011).
Stepto A. et al., "Modelling C9ORF72 Hexanucleotide Repeat Expansion in Amyotrophic Lateral Sclerosis and Frontotemporal Dementia", Acta Neuropathol 127:377-389 (2014).
Suda et al., (1987) "Mouse Embryonic Sterm Cells Exhibit Indefinite Proliferative Potential," Journal of Cellular Physiology, 133:197-201.
Sudria-Lopez E. et al., "Full Ablation of C9orf72 in Mice Causes Immune-System-Related Pathology and Neoplastic Events But No Motor Neuron Defects", Acta Neuropathologica 132(1):145-147 (2016).
Suzuki N. et al., "The Mouse C9ORF72 Ortholog is Enriched in Neurons Known to Degenerate in ALS and FTD" Nat Neurosci. 16(12):1725-1727 (Dec. 2013).
Thys, et al., "DNA Replication Dynamics of the GGGGCC Repeat of the C9orf72 Gene," Journal of Biological Chemistry, 290(48):28953-28962 (2015).
Valenzuela, et al., "High-throughput engineering of the mouse genome coupled with high-resolution expression analysis," Nature Biotech., 21(6):652-659 (2003).
Van Blitterswijk M. et al., "Genetic Modifiers in Carriers of Repeat Expansions in the C9ORF72 Gene", Molecular Neurodegeneration 9:38 (10 pages) (2014).
Waite A.J. et al., "Reduced C9orf72 Protein Levels in Frontal Cortex of Amyotrophic Lateral Sclerosis and Frontotemporal Degeneration Brain With the C9ORF72 Hexanucleotide Repeat Expansion", Neurobiology of Aging 35:1779.e5-1779.e13 (2014).
Xu Z. et al., "Expanded GGGGCC Repeat RNA Associated With Amyotrophic Lateral Sclerosis and Frontotemporal Dementia Causes Neurodegeneration", PNAS 110(19):7778-7783 (May 7, 2013).
Yang, et al., "Homologous recombination based modification in Esherichia coli and germline transmission in transgenic mice of a bacterial artificial chromsome," Nat. Biotechnol., 15:859-865 (1997).
Yu, et al., "An efficient recombination system for chromosome engineering in Escherichia coli," Proc. Natl. Acad. Sci. U.S.A. 97(11):5978-5983 (2000).
Zaias J. et al., "Reference Values for Serum Proteins of Common Laboratory Rodent Strains", Journal of American Association for Laboratory Animal Science 48(4):387-390 (Jul. 2009).
Zhang, et al., "A new logic for DNA engineering using recombination in Escherichia coli," Nat. Genet., 20:123-128 (1998).
Zhou et al., (2009) "Developing tTA transgenic rats for inducible and reversible gene expression," International Journal of Biological Sciences, 5:171-181.
International Search Report and Written Opinion dated Aug. 22, 2016 received in International Application No. PCT/US2016/034304.

(56) References Cited

OTHER PUBLICATIONS

International Search Report and Written Opinion with respect to PCT/US2017/054551 dated Dec. 11, 2017.
Statement of Relatedness under MPEP 2001.06 with Respect to U.S. Appl. No. 15/721,517 dated May 21, 2018.
Balendra and Isaacs "C9orf72-mediated ALS and FTD: multiple pathways to disease," Nat Rev Neurol. Author manuscript; available in PMC Mar. 14, 2019. Published in final edited form as: Nat Rev Neurol. Sep. 2018; 14(9): 544-558. doi:10.1038/s41582-018-0047-2.
Brevini et al., (2010) "No shortcuts to pig embryonic stem cells," Theriogenology 74:544-550.
Cao et al., (2009) "Isolation and Culture of Primary Bovine Embryonic Stem Cell Colonies by a Novel Method," Journal of Experimental Zoology, 311A:368-376.
Cinesi et al., "Contracting CAG/CTG repeats using the CRISPR-Cas9 nickase," Nature Communications, 7:13272 (Nov. 9, 2016) DOI 10.1038/ncomms13272.
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Iyer et al., (2018) "A comparative bioinformatic analysis of C9orf72", PeerJ, 6:e4391; DOI 10.7717/peerj.4391.
Jiang et al., "Gain of toxicity from ALS/FTD-linked repeat expansions in C9ORF72 is alleviated by antisense oligonucleotides targeting GGGGCC-containing RNAs," Neuron, May 4, 2016; 90(3):535-550.
Liu, et al., "C9orf72 BAC Mouse Model with Motor Deficits and Neurodegenerative Features of ALS/FTD," Neuron, May 4, 2016, 90:521-534.
Paris and Stout (2010) "Equine embryos and embryonic stem cells: Defining reliable markers of pluripotency," Theriogenology 74:516-524.
Peters, et al., "Human C9ORF72 Hexanucleotide Expansion Reproduces RNA Foci and Dipeptide Repeat Proteins but Not Neurodegeneration in BAC Transgenic Mice," Neuron, Dec. 2, 2015, 88(5):902-909.
Picher-Martel, et al., "From animal models to human disease: a genetic approach for personalized medicine in ALS," Acta Neuropathologica Communications, (2016) 4:70 (29 pages).
Tong, et al., "Production of p53 gene knockout rats by homologous recombination in embryonic stem cells," Nature, 467(7312):211-213 (Sep. 9, 2010).
Statement of Relatedness under MPEP 2001.06 with Respect to U.S. Appl. No. 15/721,517, dated Jan. 10, 2020.
Abramycheva, et al., "C9ORF72 hexanucleotide repeat expansion in ALS patients from the Central European Russia population," Neurobiology of Aging, 36(10):2908:e5-e9, (2015).
Abugable, et al., "DNA repair and neurological disease: From molecular understanding to the development of diagnostics and model organisms," DNA Repair (Amst.), 81:102669, 13 pages (2019).
Arogundade, et al., "Antisense RNA foci are associated with nucleoli and TDP-43 mislocalization in C9orf72-ALS/FTD: a quantitative study," Acta Neuropathologica, 137(3):527- 530 (2019).
Barthold, "Genetically altered mice: phenotypes, no phenotypes, and Faux phenotypes," Genetica, 122(1):75-88 (2004).
Birling, et al., "Modeling human disease in rodents by CRISPR/Cas9 genome editing," Mamm. Genome, 28(7-8):291-301 (2017).
Brevini, et al., "Porcine embryonic stem cells: Facts, challenges and hopes," Theriogenology, 68 Suppl. 1:S206-S213 (2007).
Brown et al., "Amyotrophic Lateral Sclerosis," The New England Journal of Medicine, 377(2):162-172 (2017).
Chang et al., "Non-homologous DNA end joining and alternative pathways to double-strand break repair," Nat. Rev. Mol. Cell Biol.,18(8):495-506 (2017).
Clark, et al., "A future for transgenic livestock," Nat. Rev. Genet., 4(10):825-833 (2003).
Cleary et al., "Improved PCR based methods for detecting C9orf72 hexanucleotide repeat expansions," Mol. Cell. Probes, 30(4):218-224 (2016).
Conlon et al., "The C9ORF72 GGGGCC expansion forms RNA G-quadruplex inclusions and sequesters hnRNP H to disrupt splicing in ALS brains," eLife, 5:e17820, 28 pages, (2016).
Engle, Sandra J., "Utilizing iPSC for Target Discovery in CNS," Biogen, Predict 3D, Sep. 5-6, 2019, Boston, MA, 22 pages.
Genoway, "Humanized Mouse Model," retrieved from https://www.genoway.com/services/customized-mouse/knockin models/humanisation.htm on May 12, 2018.
Gomez, et al., "Derivation of cat embryonic stem-like cells from in vitro-produced blastocysts on homologous and heterologous feeder cells," Theriogenology, 74(4): 498-515 (2010).
Graham, et al., "Resources for the design of CRISPR gene editing experiments," Genome Biol., 16:260, (2015).
Harari, et al., "Bridging the Species Divide: Transgenic Mice Humanized for Type-I Interferon Response," PLoS One, 9(1): e84259, (2014).
Hukema et al., "Retraction Note to: A new inducible transgenic mouse model for C9orf72-associated GGGGCC repeat expansion supports a gain-of-function mechanism in C9orf72-associated ALS and FTD," Acta Neuropathologica Communications, 4(1):129, (2016).
Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Kumar, et al., "Transgenic Mouse Technology: Principles and Methods," Methods Mol. Biol., 590:335-362, (2009).
La Spada et al., "Repeat expansion disease: Progress and puzzles in disease pathogenesis," Nat Rev Genet., 11(4):247-258, (2010).
McMurray, "Mechanisms of trinucleotide repeat instability during human development," Nat. Rev. Genet., 11(11):786-799, (2010).
Mullins, et al., "Transgenesis in the rat and larger mammals," J. Clin. Invest. 97(7):1557-1560, (1996).
Munoz, et al., "Conventional pluripotency markers are unspecific for bovine embryonicderived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75 (1998).
Paulson, "Chapter 9: Repeat expansion diseases," Handbook of Clinical Neurology, 147:105123, (2018).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Schludi et al., "Distribution of dipeptide repeat proteins in cellular models and C9orf72 mutation cases suggests link to transcriptional silencing," Acta Neuropathol., 130(4):537-555, (2015).
Schludi et al., "Erratum to: Distribution of dipeptide repeat proteins in cellular models and C9orf72 mutation cases suggests link to transcriptional silencing," Acta Neuropathol., 130(4):557-558, (2015).
Sigmund, "Viewpoint: Are Studies in Genetically Altered Mice Out of Control?," Arterioscler. Thromb. Vasc. Biol., 20(6):1425-1429, (2000).
Traynor et al., "Special Issue on amyotrophic lateral sclerosis," Exp. Neurol., 262 Pt B:73-74, (2014).
Van Der Zee, et al., "A pan-European study of the C9orf72 repeat associated with FTLD: geographic prevalence, genomic instability, and intermediate repeats," Hum. Mutat., 34(2):363- 373, (2013).
Wakchaure, et al., "Transgenic Animals: A Review on its Various Dimensions and Applications in Animal Biotechnology," International Journal of Emerging Technology and Advanced Engineering, 5(11):210-213, (2015).
WIPO Application No. PCT/US2019/066317, PCT International Search Report and Written Opinion of the International Searching Authority dated Mar. 11, 2020.

(56) References Cited

OTHER PUBLICATIONS

Statement of Relatedness under MPEP 2001.06 with Respect to U.S. Appl. No. 15/721,517, dated Mar. Apr. 2, 2020.

* cited by examiner

SEQUENCE LISTING

<160> NUMBER OF SEQ ID NOS: 84

<210> SEQ ID NO 1
<211> LENGTH: 6
<212> TYPE: DNA
<213> ORGANISM: Artificial Sequence
<220> FEATURE:
<223> OTHER INFORMATION: Heterologous Hexanucleotide sequence

<400> SEQUENCE: 1 ggggcc                                                                    6

<210> SEQ ID NO 2
<211> LENGTH: 964
<212> TYPE: DNA
<213> ORGANISM: Homo sapiens

<400> SEQUENCE: 2
gggtctagca agagcaggtg tgggtttagg aggtgtgtgt ttttgttttt cccaccctct         60
ctccccacta cttgctctca cagtactcgc tgagggtgaa caagaaaaga cctgataaag        120
attaaccaga agaaaacaag gagggaaaca accgcagcct gtagcaagct ctggaactca        180
ggagtcgcgc gctatgcgat cgcggggccg gggccggggc cgcgatcgcg ggcgtggtc         240 ggggcgggcc cggggcgggc cccggggcgg ggctgcggtt gcggtgcctg cgcccgcggc        300
ggcggaggcg caggcggtgg cgagtgggtg agtgaggagg cggcatcctg gcgggtggct        360
gtttggggtt cggctgccgg gaagaggcgc gggtagaagc gggggctctc ctcagagctc        420
gacgcatttt tactttccct ctcatttctc tgaccgaagc tgggtgtcgg gctttcgcct        480
ctagcgactg gtggaattgc ctgcatccgg gccccgggct tcccggcggc ggcggcggcg        540
gcggcggcgc agggacaagg gatggggatc tggcctcttc cttgctttcc cgccctcagt        600
acccgagctg tctccttccc ggggacccgc tgggagcgct gccgctgcgg gctcgagaaa        660
agggagcctc gggtactgag aggcctcgcc tgggggaagg ccggagggtg ggcggcgcgc        720
ggcttctgcg gaccaagtcg gggttcgcta ggaacccgag acggtccctg ccggcgagga        780
gatcatgcgg gatgagatgg gggtgtggag acgcctgcac aatttcagcc caagcttcta        840
gagagtggtg atgacttgca tatgagggca gcaatgcaag tcggtgtgct ccccattctg        900
tgggacatga cctggttgct tcacagctcc gagatgacac agacttgctt aaaggaagtg        960
actc                                                                    964

<210> SEQ ID NO 3
<211> LENGTH: 1528
<212> TYPE: DNA
<213> ORGANISM: Homo sapiens

<400> SEQUENCE: 3
gggtctagca agagcaggtg tgggtttagg aggtgtgtgt ttttgttttt cccaccctct         60
ctccccacta cttgctctca cagtactcgc tgagggtgaa caagaaaaga cctgataaag        120
attaaccaga agaaaacaag gagggaaaca accgcagcct gtagcaagct ctggaactca        180
ggagtcgcgc gctatgcgat cgccgtctcg ggccggggc cggggccggg gccggggccg         240
gggccggggc cggggccggg gccggggccg gggccggggc cggggccggg gccggggccg        300
gggccggggc cggggccggg gccggggccg gggccggggc cggggccggg gccggggccg        360
gggccggggc cggggccggg gccggggccg gggccggggc cggggccggg gccggggccg        420
gggccggggc cggggccggg gccggggccg gggccggggc cggggccggg gccggggccg        480

```
gggccggggc cggggccggg gccggggccg gggccggggc cggggccggg gccggggccg    540
gggccggggc cggggccggg gccggggccg gggccggggc cggggccggg gccggggccg    600
gggccggggc cggggccggg gccggggccg gggccggggc cggggccggg gccggggccg    660
gggccggggc cggggccggg gccggggccg gggccggggc cggggccggg gccggggccg    720
gggccggggc cggggccggg gccggggccg gggccggggc cgagaccctc gagggccggc    780
cgctagcgcg atcgcgggc gtggtcgggg cgggcccggg ggcgggcccg gggcggggct    840
gcggttgcgg tgcctgcgcc cgcggcggcg gaggcgcagg cggtggcgag tgggtgagtg    900
aggaggcgga atcctggcgg gtggctgttt ggggttcggc tgccgggaag aggcgcgggt    960
agaagcgggg gctctcctca gagctcgacg catttttact ttccctctca tttctctgac   1020
cgaagctggg tgtcgggctt tcgcctctag cgactggtgg aattgcctgc atccgggccc   1080
cgggcttccc ggcggcggcg gcggcggcgg cggcgcaggg acaagggatg gggatctggc   1140
ctcttccttg ctttcccgcc ctcagtaccc gagctgtctc cttcccgggg acccgctggg   1200
agcgctgccg ctgcgggctc gagaaaaggg agcctcgggt actgagaggc ctcgcctggg   1260
ggaaggccgg agggtgggcg gcgcgcggct tctgcggacc aagtcggggt tcgctaggaa   1320
cccgagacgg tccctgccgg cgaggagatc atgcgggatg agatgggggt gtggagacgc   1380
ctgcacaatt tcagcccaag cttctagaga gtggtgatga cttgcatatg agggcagcaa   1440
tgcaagtcgg tgtgctcccc attctgtggg acatgacctg gttgcttcac agctccgaga   1500
tgacacagac ttgcttaaag gaagtgac                                     1528

<210> SEQ ID NO 4
<211> LENGTH: 3621
<212> TYPE: DNA
<213> ORGANISM: Artificial Sequence
<220> FEATURE:
<223> OTHER INFORMATION: 8026 insert nucleic acid without homology arms

<400> SEQUENCE: 4
gggtctagca agagcaggtg tgggtttagg aggtgtgtgt ttttgttttt cccaccctct     60
ctccccacta cttgctctca cagtactcgc tgagggtgaa caagaaaaga cctgataaag    120
attaaccaga agaaaacaag gagggaaaca accgcagcct gtagcaagct ctggaactca    180
ggagtcgcgc gctatgcgat cgcggggccg gggccggggc cgcgatcgcg gggcgtggtc    240
ggggcgggcc cggggcgggg cccggggcgg ggctgcggtt gcggtgcctg cgcccgcggc    300
ggcggaggcg caggcggtgg cgagtgggtg agtgaggagg cggcatcctg gcgggtggct    360 gtttgggggtt cggctgccgg gaagaggcgc gggtagaagc gggggctctc ctcagagctc    420
gacgcatttt tactttccct ctcatttctc tgaccgaagc tgggtgtcgg gctttcgcct    480
ctagcgactg gtggaattgc ctgcatccgg gccccgggct tcccggcggc ggcggcggcg    540
gcggcggcgc agggacaagg gatggggatc tggcctcttc cttgctttcc cgccctcagt    600
acccgagctg tctccttccc ggggacccgc tgggagcgct gccgctgcgg gctcgagaaa    660
agggagcctc gggtactgag aggcctcgcc tggggaagg ccggagggtg gcggcgcgc    720 ggcttctgcg gaccaagtcg gggttcgcta ggaacccgag acggtccctg ccggcgagga    780
gatcatgcgg gatgagatgg gggtgtggag acgcctgcac aatttcagcc caagcttcta    840
gagagtggtg atgacttgca tatgagggca gcaatgcaag tcggtgtgct ccccattctg    900
tgggacatga cctggttgct tcacagctcc gagatgacac agacttgctt aaaggaagtg    960
```

```
actcgagata acttcgtata atgtatgcta tacgaagtta tatgcatggc ctccgcgccg    1020
ggttttggcg cctcccgcgg gcgccccct  cctcacggcg agcgctgcca cgtcagacga    1080
agggcgcagc gagcgtcctg atccttccgc ccggacgctc aggacagcgg cccgctgctc    1140
ataagactcg gccttagaac cccagtatca gcagaaggac attttaggac gggacttggg    1200
tgactctagg gcactggttt tctttccaga gagcggaaca ggcgaggaaa agtagtccct    1260
tctcggcgat tctgcggagg gatctccgtg gggcggtgaa cgccgatgat tatataagga    1320
cgcgccgggt gtggcacagc tagttccgtc gcagccggga tttgggtcgc ggttcttgtt    1380
tgtggatcgc tgtgatcgtc acttggtgag tagcgggctg ctgggctggc cggggctttc    1440
gtggccgccg ggccgctcgg tgggacggaa gcgtgtggag agaccgccaa gggctgtagt    1500
ctgggtccgc gagcaaggtt gccctgaact gggggttggg gggagcgcag caaaatggcg    1560
gctgttcccg agtcttgaat ggaagacgct tgtgaggcgg gctgtgaggt cgttgaaaca    1620
aggtgggggg catggtgggc ggcaagaacc caaggtcttg aggccttcgc taatgcggga    1680
aagctcttat tcgggtgaga tgggctgggg caccatctgg ggaccctgac gtgaagtttg    1740
tcactgactg gagaactcgg tttgtcgtct gttgcggggg cggcagttat ggcggtgccg    1800
ttgggcagtg caccegtacc tttggagcg cgcgccctcg tcgtgtcgtg acgtcacccg     1860
ttctgttggc ttataatgca gggtggggcc acctgccggt aggtgtgcgg taggcttttc    1920
tccgtcgcag gacgcagggt tcgggcctag ggtaggctct cctgaatcga caggcgccgg    1980
acctctggtg aggggaggga taagtgaggc gtcagtttct ttggtcggtt ttatgtacct    2040
atcttcttaa gtagctgaag ctccggtttt gaactatgcg ctcggggttg gcgagtgtgt    2100
tttgtgaagt ttttaggca  ccttttgaaa tgtaatcatt tgggtcaata tgtaattttc    2160
agtgttagac tagtaaattg tccgctaaat tctggccgtt tttggctttt ttgttagacg    2220
tgttgacaat taatcatcgg catagtatat cggcatagta taatacgaca aggtgaggaa    2280
ctaaaccatg ggatcggcca ttgaacaaga tggattgcac gcaggttctc cggccgcttg    2340
ggtggagagg ctattcggct atgactgggc acaacagaca atcggctgct ctgatgccgc    2400
cgtgttccgg ctgtcagcgc aggggcgccc ggttcttttt gtcaagaccg acctgtccgg    2460
tgccctgaat gaactgcagg acgaggcagc gcggctatcg tggctggcca cgacgggcgt    2520
tccttgcgca gctgtgctcg acgttgtcac tgaagcggga agggactggc tgctattggg    2580
cgaagtgccg gggcaggatc tcctgtcatc tcaccttgct cctgccgaga agtatccat     2640
catggctgat gcaatgcggc ggctgcatac gcttgatccg gctacctgcc cattcgacca    2700
ccaagcgaaa catcgcatcg agcgagcacg tactcggatg aagccggtc  ttgtcgatca    2760
ggatgatctg gacgaagagc atcagggct  cgcgccagcc gaactgttcg ccaggctcaa    2820
ggcgcgcatg cccgacggcg atgatctcgt cgtgacccat ggcgatgcct gcttgccgaa    2880
tatcatggtg gaaaatggcc gcttttctgg attcatcgac tgtggccggc tgggtgtggc    2940
ggaccgctat caggacatag cgttggctac ccgtgatatt gctgaagagc ttggcggcga    3000
atgggctgac cgcttcctcg tgctttacgg tatcgccgct cccgattcgc agcgcatcgc    3060
cttctatcgc cttcttgacg agttcttctg agggatccg  ctgtaagtct gcagaaattg    3120
atgatctatt aaacaataaa gatgtccact aaaatggaag ttttcctgt  catactttgt    3180
taagaagggt gagaacagag tacctacatt tgaatggaa  ggattggagc tacggggtg     3240
gggtgggggt gggattagat aaatgcctgc tctttactga aggctcttta ctattgcttt    3300
atgataatgt ttcatagttg gatatcataa tttaaacaag caaaaccaaa ttaagggcca    3360
```

```
gctcattcct cccactcatg atctatagat ctatagatct ctcgtgggat cattgttttt    3420
ctcttgattc ccactttgtg gttctaagta ctgtggtttc caaatgtgtc agtttcatag    3480
cctgaagaac gagatcagca gcctctgttc cacatacact tcattctcag tattgttttg    3540
ccaagttcta attccatcag acctcgacct gcagcccta gataacttcg tataatgtat     3600
gctatacgaa gttatgctag c                                              3621

<210> SEQ ID NO 5
<211> LENGTH: 1006
<212> TYPE: DNA
<213> ORGANISM: Artificial Sequence
<220> FEATURE:
<223> OTHER INFORMATION: 8026 insert nucleic acid without homology arms
      and after excision of neo

<400> SEQUENCE: 5
gggtctagca agagcaggtg tgggtttagg aggtgtgtgt ttttgttttt cccaccctct     60
ctccccacta cttgctctca cagtactcgc tgagggtgaa caagaaaaga cctgataaag    120
attaaccaga agaaaacaag gagggaaaca accgcagcct gtagcaagct ctggaactca    180
ggagtcgcgc gctatgcgat cgcggggccg gggccggggc cgcgatcgcg gggcgtggtc    240
ggggcgggcc cggggggcggg cccggggcgg ggctgcggtt gcggtgcctg cgcccgcggc   300
ggcggaggcg caggcggtgg cgagtgggtg agtgaggagg cggcatcctg cgggtggct    360 gtttggggtt cggctgccgg gaagaggcgc gggtagaagc ggggggctctc ctcagagctc   420 gacgcatttt tactttccct ctcatttctc tgaccgaagc tgggtgtcgg gctttcgcct    480
ctagcgactg gtggaattgc ctgcatccgg gccccgggct tcccggcggc ggcggcggcg    540
gcggcggcgc agggacaagg gatggggatc tggcctcttc cttgctttcc cgccctcagt    600
acccgagctg tctccttccc ggggaccccgc tgggagcgct gccgctgcgg gctcgagaaa    660
agggagcctc gggtactgag aggcctcgcc tgggggaagg ccggagggtg ggcggcgcgc    720
ggcttctgcg gaccaagtcg gggttcgcta ggaacccgag acggtccctg ccggcgagga    780
gatcatgcgg gatgagatgg gggtgtggag acgcctgcac aatttcagcc caagcttcta    840
gagagtggtg atgacttgca tatgagggca gcaatgcaag tcggtgtgct ccccattctg    900
tgggacatga cctggttgct tcacagctcc gagatgacac agacttgctt aaaggaagtg    960
actcgagata acttcgtata atgtatgcta tacgaagtta tgctag                  1006

<210> SEQ ID NO 6
<211> LENGTH: 4180
<212> TYPE: DNA
<213> ORGANISM: Artificial Sequence
<220> FEATURE:
<223> OTHER INFORMATION: 8026 Insert Nucleic acid without homology arms
      plus neo cassette

<400> SEQUENCE: 6
ggtctagcaa gagcaggtgt gggtttagga ggtgtgtgtt tttgtttttc ccaccctctc    60
tccccactac ttgctctcac agtactcgct gagggtgaac aagaaaagac ctgataaaga   120
ttaaccagaa gaaaacaagg agggaaacaa ccgcagcctg tagcaagctc tggaactcag   180
gagtcgcgcg ctatgcgatc gccgtctcgg ggccggggcc ggggccgggg ccggggccgg   240
ggccggggcc ggggccgggg ccggggccgg gccggggcc ggggccgggg ccggggccgg   300
ggccggggcc ggggccgggg ccggggccgg ggccggggcc ggggccgggg ccggggccgg   360
```

```
ggccggggcc ggggccgggg ccggggccgg ggccggggcc ggggccgggg ccggggccgg    420
ggccggggcc ggggccgggg ccggggccgg ggccggggcc ggggccgggg ccggggccgg    480
ggccggggcc ggggccgggg ccggggccgg ggccggggcc ggggccgggg ccggggccgg    540
ggccggggcc ggggccgggg ccggggccgg ggccggggcc ggggccgggg ccggggccgg    600
ggccggggcc ggggccgggg ccggggccgg ggccggggcc ggggccgggg ccggggccgg    660
ggccggggcc ggggccgggg ccggggccgg ggccggggcc ggggccgggg ccggggccgg    720
ggccggggcc ggggccgggg ccggggccgg ggccggggcc gagaccctcg agggccggcc    780
gctagcgcga tcgcggggcg tggtcggggc gggcccgggg gcgggcccgg ggcggggctg    840
cggttgcggt gcctgcgccc gcggcggcgg aggcgcaggc ggtggcgagt gggtgagtga    900
ggaggcggca tcctggcggg tggctgtttg gggttcggct gccgggaaga ggcgcgggta    960
gaagcggggg ctctcctcag agctcgacgc attttttactt tccctctcat ttctctgacc   1020
gaagctgggt gtcgggcttt cgcctctagc gactggtgga attgcctgca tccgggcccc   1080
gggcttcccg gcggcggcgg cggcggcggc ggcgcaggga caaggatgg  ggatctggcc   1140
tcttccttgc tttcccgccc tcagtacccg agctgtctcc ttcccgggga cccgctggga   1200
gcgctgccgc tgcgggctcg agaaaaggga gcctcgggta ctgagaggcc tcgcctgggg   1260
gaaggccgga gggtgggcgg cgcgcggctt ctgcggacca agtcggggtt cgctaggaac   1320
ccgagacggt ccctgccggc gaggagatca tgcgggatga gatggggggtg tggagacgcc   1380
tgcacaattt cagcccaagc ttctagagag tggtgatgac ttgcatatga gggcagcaat   1440
gcaagtcggt gtgctcccca ttctgtggga catgacctgg ttgcttcaca gctccgagat   1500
gacacagact tgcttaaagg aagtgactcg agataacttc gtataatgta tgctatacga   1560
agttatatgc atggcctccg cgccgggttt tggcgcctcc cgcgggcgcc ccctcctca   1620
cggcgagcgc tgccacgtca gacgaagggc gcagcgagcg tcctgatcct tccgcccgga   1680
cgctcaggac agcggcccgc tgctcataag actcggcctt agaacccccag tatcagcaga   1740
aggacatttt aggacgggac ttgggtgact ctagggcact ggttttcttt ccagagagcg   1800
gaacaggcga ggaaaagtag tcccttctcg gcgattctgc ggaggatct  ccgtggggcg   1860
gtgaacgccg atgattatat aaggacgcgc cgggtgtggc acagctagtt ccgtcgcagc   1920
cgggatttgg gtcgcggttc ttgtttgtgg atcgctgtga tcgtcacttg gtgagtagcg   1980
ggctgctggg ctggccgggg ctttcgtggc cgccgggccg ctcggtggga cggaagcgtg   2040
tggagagacc gccaagggct gtagtctggg tccgcgagca aggttgccct gaactggggg   2100
ttggggggag cgcagcaaaa tggcggctgt tcccgagtct tgaatggaag acgcttgtga   2160
ggcgggctgt gaggtcgttg aaacaaggtg ggggcatgg  tgggcggcaa gaacccaagg   2220
tcttgaggcc ttcgctaatg cgggaaagct cttattcggg tgagatgggc tggggcacca   2280
tctgggggacc ctgacgtgaa gtttgtcact gactggagaa ctcggtttgt cgtctgttgc   2340
gggggcggca gttatggcgg tgccgttggg cagtgcaccc gtacctttgg gagcgcgcgc   2400
cctcgtcgtg tcgtgacgtc acccgttctg ttggcttata atgcagggtg gggccacctg   2460
ccggtaggtg tgcggtaggc ttttctccgt cgcaggacgc agggttcggg cctagggtag   2520
gctctcctga atcgacaggc gccggacctc tggtgagggg agggataagt gaggcgtcag   2580
tttctttggt cggttttatg tacctatctt cttaagtagc tgaagctccg gttttgaact   2640
atgcgctcgg ggttggcgag tgtgtttgt  gaagtttttt aggcaccttt tgaaatgtaa   2700
tcatttgggt caatatgtaa ttttcagtgt tagactagta aattgtccgc taaattctgg   2760
```

```
ccgttttttgg cttttttgtt agacgtgttg acaattaatc atcggcatag tatatcggca    2820
tagtataata cgacaaggtg aggaactaaa ccatgggatc ggccattgaa caagatggat    2880
tgcacgcagg ttctccggcc gcttgggtgg agaggctatt cggctatgac tgggcacaac    2940
agacaatcgg ctgctctgat gccgccgtgt tccggctgtc agcgcagggg cgcccggttc    3000
tttttgtcaa gaccgacctg tccggtgccc tgaatgaact gcaggacgag gcagcgcggc    3060
tatcgtggct ggccacgacg ggcgttcctt gcgcagctgt gctcgacgtt gtcactgaag    3120
cgggaaggga ctggctgcta ttgggcgaag tgccggggca ggatctcctg tcatctcacc    3180
ttgctcctgc cgagaaagta tccatcatgg ctgatgcaat gcggcggctg catacgcttg    3240
atccggctac ctgcccattc gaccaccaag cgaaacatcg catcgagcga gcacgtactc    3300
ggatggaagc cggtcttgtc gatcaggatg atctggacga agagcatcag gggctcgcgc    3360
cagccgaact gttcgccagg ctcaaggcgc gcatgcccga cggcgatgat ctcgtcgtga    3420
cccatggcga tgcctgcttg ccgaatatca tggtggaaaa tggccgcttt tctggattca    3480
tcgactgtgg ccggctgggt gtggcggacc gctatcagga catagcgttg gctacccgtg    3540
atattgctga agagcttggc ggcgaatggg ctgaccgctt cctcgtgctt tacggtatcg    3600
ccgctcccga ttcgcagcgc atcgccttct atcgccttct tgacgagttc ttctgagggg    3660
atccgctgta agtctgcaga aattgatgat ctattaaaca ataaagatgt ccactaaaat    3720
ggaagttttt cctgtcatac tttgttaaga agggtgagaa cagagtacct acatttgaa    3780 tggaaggatt ggagctacgg gggtggggt ggggtgggat tagataaatg cctgctcttt    3840
actgaaggct ctttactatt gctttatgat aatgtttcat agttggatat cataatttaa    3900
acaagcaaaa ccaaattaag ggccagctca ttcctcccac tcatgatcta tagatctata    3960
gatctctcgt gggatcattg ttttttctctt gattcccact ttgtggttct aagtactgtg    4020
gtttccaaat gtgtcagttt catagcctga agaacgagat cagcagcctc tgttccacat    4080
acacttcatt ctcagtattg ttttgccaag ttctaattcc atcagacctc gacctgcagc    4140
ccctagataa cttcgtataa tgtatgctat acgaagttat                         4180
```

<210> SEQ ID NO 7
<211> LENGTH: 1566
<212> TYPE: DNA
<213> ORGANISM: Artificial Sequence
<220> FEATURE:
<223> OTHER INFORMATION: 8028 insert nucleic acid with lox site after excision of neo and without homology arms

<400> SEQUENCE: 7

```
gggtctagca agagcaggtg tgggtttagg aggtgtgtgt ttttgttttt cccaccctct     60
ctccccacta cttgctctca cagtactcgc tgagggtgaa caagaaaaga cctgataaag    120
attaaccaga agaaaacaag gagggaaaca accgcagcct gtagcaagct ctggaactca    180
ggagtcgcgc gctatgcgat cgccgtctcg ggccggggc cggggccggg gccggggccg    240
gggccggggc cggggccggg gccggggccg gggccggggc cggggccggg gccggggccg    300
gggccggggc cggggccggg gccggggccg gggccggggc cggggccggg gccggggccg    360
gggccggggc cggggccggg gccggggccg gggccggggc cggggccggg gccggggccg    420
gggccggggc cggggccggg gccggggccg gggccggggc cggggccggg gccggggccg    480
gggccggggc cggggccggg gccggggccg gggccggggc cggggccggg gccggggccg    540
gggccggggc cggggccggg gccggggccg gggccggggc cggggccggg gccggggccg    600
```

```
gggccggggc cggggccggg gccggggccg gggccggggc cggggccggg gccggggccg    660
gggccggggc cggggccggg gccggggccg gggccggggc cggggccggg gccggggccg    720
gggccggggc cggggccggg gccggggccg gggccggggc cgagaccctc gagggccggc    780
cgctagcgcg atcgcgggc gtggtcgggg cgggcccggg ggcgggcccg gggcggggct    840
gcggttgcgg tgcctgcgcc cgcggcggcg gaggcgcagg cggtggcgag tgggtgagtg    900
aggaggcgga atcctggcgg gtggctgttt ggggttcggc tgccgggaag aggcgcgggt    960
agaagcgggg gctctcctca gagctcgacg cattttttact ttccctctca tttctctgac   1020
cgaagctggg tgtcgggctt tcgcctctag cgactggtgg aattgcctgc atccgggccc   1080
cgggcttccc ggcggcggcg gcggcggcgg cggcgcaggg acaagggatg gggatctggc   1140
ctcttccttg ctttcccgcc ctcagtaccc gagctgtctc cttcccgggg acccgctggg   1200
agcgctgccg ctgcgggctc gagaaaaggg agcctcgggt actgagaggc ctcgcctggg   1260
ggaaggccgg agggtgggcg gcgcgcggct tctgcggacc aagtcggggt tcgctaggaa   1320
cccgagacgg tccctgccgg cgaggagatc atgcgggatg agatgggggt gtggagacgc   1380
ctgcacaatt tcagcccaag cttctagaga gtggtgatga cttgcatatg agggcagcaa   1440
tgcaagtcgg tgtgctcccc attctgtggg acatgacctg gttgcttcac agctccgaga   1500
tgacacagac ttgcttaaag gaagtgactc gagataactt cgtataatgt atgctatacg   1560
aagtta                                                             1566

<210> SEQ ID NO 8
<211> LENGTH: 3821
<212> TYPE: DNA
<213> ORGANISM: Artificial Sequence
<220> FEATURE:
<223> OTHER INFORMATION: 8026 targeting nucleic acid with homology arms
      and neo cassette

<400> SEQUENCE: 8
gaaccgcggc gcgtcaagca gagacgagtt ccgcccacgt gaaagatggc gtttgtagtg    60
acagccatcc caattgccct ttccttctag gtggaaagtg gggtctagca agagcaggtg   120
tgggtttagg aggtgtgtgt ttttgttttt cccaccctct ctccccacta cttgctctca   180
cagtactcgc tgagggtgaa caagaaaaga cctgataaag attaaccaga agaaaacaag   240
gagggaaaca accgcagcct gtagcaagct ctggaactca ggagtcgcgc gctatgcgat   300
cgcggggccg gggccggggc cgcgatcgcg gggcgtggtc ggggcggggcc cggggggcggg   360 cccggggcgg ggctgcggtt gcggtgcctg cgcccgcggc ggcggaggcg caggcggtgg   420
cgagtggtgg agtgaggagg cggcatcctg gcggtggt gttgggtt cggctgccgg   480 gaagaggcgc gggtagaagc ggggggctctc ctcagagctc gacgcatttt tactttccct   540
ctcatttctc tgaccgaagc tgggtgtcgg gctttcgcct ctagcgactg gtggaattgc   600
ctgcatccgg gccccgggct tcccggcggc ggcggcggcg gcgcggcgc agggacaagg   660 gatggggatc tggcctcttc cttgcttttcc cgccctcagt acccgagctg tctccttccc   720 ggggaccccgc tgggagcgct gccgctgcgg gctcgagaaa agggagcctc gggtactgag   780
aggcctcgcc tggggaagg ccggagggtg gcggcgcgc ggcttctgcg gaccaagtcg   840
gggttcgcta ggaacccgag acggtccctg ccggcgagga gatcatgcgg gatgagatgg   900
gggtgtggag acgcctgcac aatttcagcc caagcttcta gagagtggtg atgacttgca   960
tatgagggca gcaatgcaag tcggtgtgct ccccattctg tgggacatga cctggttgct   1020
```

```
tcacagctcc gagatgacac agacttgctt aaaggaagtg actcgagata acttcgtata    1080
atgtatgcta tacgaagtta tatgcatggc ctccgcgccg ggttttggcg cctcccgcgg    1140 gcgccccct  cctcacggcg agcgctgcca cgtcagacga agggcgcagc gagcgtcctg    1200
atccttccgc ccggacgctc aggacagcgg cccgctgctc ataagactcg gccttagaac    1260
cccagtatca gcagaaggac attttaggac gggacttggg tgactctagg cactggtttt    1320
tctttccaga gagcggaaca ggcgaggaaa agtagtccct tctcggcgat ctgcgcgagg    1380
gatctccgtg gggcggtgaa cgccgatgat tatataagga cgcgccgggt gtggcacagc    1440
tagttccgtc gcagccggga tttgggtcgc ggttcttgtt tgtggatcgc tgtgatcgtc    1500
acttggtgag tagcgggctg ctgggctggc cggggctttc gtggccgccg gccgctcgg     1560 tgggacggaa gcgtgtggag agaccgccaa gggctgtagt ctgggtccgc gagcaaggtt    1620
gccctgaact ggggggttggg gggagcgcag caaaatggcg gctgttcccg agtcttgaat    1680
ggaagacgct tgtgaggcgg gctgtgaggt cgttgaaaca aggtgggggg catggtgggc    1740
ggcaagaacc caaggtcttg aggccttcgc taatgcggga aagctcttat tcgggtgaga    1800
tgggctgggg caccatctgg ggaccctgac gtgaagtttg tcactgactg gagaactcgg    1860
tttgtcgtct gttgcggggg cggcagttat ggcggtgccg ttgggcagtg cacccgtacc    1920
tttgggagcg cgcgccctcg tcgtgtcgtg acgtcacccg ttctgttggc ttataatgca    1980
gggtggggcc acctgccggt aggtgtgcgg taggcttttc tccgtcgcag acgcagggt    2040 tcgggcctag ggtaggctct cctgaatcga caggcgccgg acctctggtg aggggaggga    2100
taagtgaggc gtcagtttct ttggtcggtt ttatgtacct atcttcttaa gtagctgaag    2160
ctccggtttt gaactatgcg ctcggggttg gcgagtgtgt tttgtgaagt tttttaggca    2220 cctttttgaaa tgtaatcatt tgggtcaata tgtaattttc agtgttagac tagtaaattg    2280
tccgctaaat tctggccgtt tttggctttt ttgttagacg tgttgacaat taatcatcgg    2340
catagtatat cggcatagta taatacgaca aggtgaggaa ctaaaccatg ggatcggcca    2400
ttgaacaaga tggattgcac gcaggttctc cggccgcttg ggtggagagg ctattcggct    2460
atgactgggc acaacagaca atcggctgct ctgatgccgc cgtgttccgg ctgtcagcgc    2520
aggggcgccc ggttcttttt gtcaagaccg acctgtccgg tgccctgaat gaactgcagg    2580
acgaggcagc gcggctatcg tggctggcca cgacgggcgt tccttgcgca gctgtgctcg    2640
acgttgtcac tgaagcggga agggactggc tgctattggg cgaagtgccg gggcaggatc    2700
tcctgtcatc tcaccttgct cctgccgaga aagtatccat catggctgat gcaatgcggc    2760
ggctgcatac gcttgatccg gctacctgcc cattcgacca ccaagcgaaa catcgcatcg    2820
agcgagcacg tactcggatg gaagccggtc ttgtcgatca ggatgatctg gacgaagagc    2880 atcagggct  cgcgccagcc gaactgttcg ccaggctcaa ggcgcgcatg cccgacggcg    2940
atgatctcgt cgtgacccat ggcgatgcct gcttgccgaa tatcatggtg gaaaatggcc    3000
gcttttctgg attcatcgac tgtggccggc tgggtgtggc ggaccgctat caggacatag    3060
cgttggctac ccgtgatatt gctgaagagc ttggcggcga atgggctgac cgcttcctcg    3120
tgctttacgg tatcgccgct cccgattcgc agcgcatcgc cttctatcgc cttcttgacg    3180
agttcttctg aggggatccg ctgtaagtct gcagaaattg atgatctatt aaacaataaa    3240
gatgtccact aaaatggaag ttttttcctgt catactttgt taagaagggt gagaacagag    3300
tacctacatt ttgaatggaa ggattggagc tacggggtg  gggtgggg   gggattagat    3360
```

| | |
|---|---|
| aaatgcctgc tctttactga aggctcttta ctattgcttt atgataatgt tcatagttg | 3420 |
| gatatcataa tttaaacaag caaaaccaaa ttaagggcca gctcattcct cccactcatg | 3480 |
| atctatagat ctatagatct ctcgtgggat cattgttttt ctcttgattc ccactttgtg | 3540 |
| gttctaagta ctgtggtttc caaatgtgtc agtttcatag cctgaagaac gagatcagca | 3600 |
| gcctctgttc cacatacact tcattctcag tattgttttg ccaagttcta attccatcag | 3660 |
| acctcgacct gcagcccta gataacttcg tataatgtat gctatacgaa gttatgctag | 3720 |
| cattgtgact tgggcatcac ttgactgatg gtaatcagtt gcagagagag aagtgcactg | 3780 |
| attaagtctg tccacacagg gtctgtctgg ccaggagtgc a | 3821 |

<210> SEQ ID NO 9
<211> LENGTH: 4387
<212> TYPE: DNA
<213> ORGANISM: Artificial Sequence
<220> FEATURE:
<223> OTHER INFORMATION: 8026 insert nucleic acid with homology arms, hexanucleotide repeat(s) and neo cassette

<400> SEQUENCE: 9

| | |
|---|---|
| gaaccgcggc gcgtcaagca gagacgagtt ccgcccacgt gaaagatggc gtttgtagtg | 60 |
| acagccatcc caattgccct ttccttctag gtggaaagtg gggtctagca agagcaggtg | 120 |
| tgggtttagg aggtgtgtgt ttttgttttt cccaccctct ctcccacta cttgctctca | 180 |
| cagtactcgc tgagggtgaa caagaaaaga cctgataaag attaaccaga agaaaacaag | 240 |
| gagggaaaca accgcagcct gtagcaagct ctggaactca ggagtcgcgc gctatgcgat | 300 |
| cgccgtctcg gggccggggc cggggccggg gccggggccg gggccggggc cggggccggg | 360 |
| gccggggccg gggccggggc cggggccggg gccggggccg gggccggggc cggggccggg | 420 |
| gccggggccg gggccggggc cggggccggg gccggggccg gggccggggc cggggccggg | 480 |
| gccggggccg gggccggggc cggggccggg gccggggccg gggccggggc cggggccggg | 540 |
| gccggggccg gggccggggc cggggccggg gccggggccg gggccggggc cggggccggg | 600 |
| gccggggccg gggccggggc cggggccggg gccggggccg gggccggggc cggggccggg | 660 |
| gccggggccg gggccggggc cggggccggg gccggggccg gggccggggc cggggccggg | 720 |
| gccggggccg gggccggggc cggggccggg gccggggccg gggccggggc cggggccggg | 780 |
| gccggggccg gggccggggc cggggccggg gccggggccg gggccggggc cggggccggg | 840 |
| gccggggccg gggccgggc cgagaccctc gagggccggc cgctagcgcg atcgcggggc | 900 |
| gtggtcgggg cgggcccggg ggcgggcccg gggcgggct gcggttgcgg tgcctgcgcc | 960 |
| cgcggcggcg gaggcgcagg cggtggcgag tgggtgagtg aggaggcggc atcctggcgg | 1020 |
| gtggctgttt gggttcggc tgccgggaag aggcgcgggt agaagcgggg gctctcctca | 1080 |
| gagctcgacg cattttact ttccctctca tttctctgac cgaagctggg tgtcgggctt | 1140 |
| tcgcctctag cgactggtgg aattgcctgc atccggccc cggcttccc ggcggcggcg | 1200 |
| gcggcggcgg cggcgcaggg acaagggatg gggatctggc ctcttccttg ctttcccgcc | 1260 |
| ctcagtaccc gagctgtctc cttcccgggg acccgctggg agcgctgccg ctgcgggctc | 1320 |
| gagaaaaggg agcctcgggt actgagaggc ctcgcctggg ggaaggccgg agggtgggcg | 1380 |
| gcgcgcggct tctgcggacc aagtcggggt tcgctaggaa cccgagacgg tcctgccgg | 1440 |
| cgaggagatc atgcgggatg agatgggggt gtggagacgc ctgcacaatt tcagcccaag | 1500 |
| cttctagaga gtggtgatga cttgcatatg agggcagcaa tgcaagtcgg tgtgctcccc | 1560 |

```
attctgtggg acatgacctg gttgcttcac agctccgaga tgacacagac ttgcttaaag   1620
gaagtgactc gagataactt cgtataatgt atgctatacg aagttatatg catggcctcc   1680
gcgccgggtt ttggcgcctc ccgcgggcgc ccccctcctc acggcgagcg ctgccacgtc   1740
agacgaaggg cgcagcgagc gtcctgatcc ttccgcccgg acgctcagga cagcggcccg   1800
ctgctcataa gactcggcct tagaaccccca gtatcagcag aaggacattt taggacggga   1860
cttgggtgac tctagggcac tggttttctt tccagagagc ggaacaggcg aggaaaagta   1920
gtcccttctc ggcgattctg cggagggatc tccgtgggc ggtgaacgcc gatgattata   1980
taaggacgcg ccggggtgtgg cacagctagt tccgtcgcag ccgggatttg ggtcgcggtt   2040
cttgtttgtg gatcgctgtg atcgtcactt ggtgagtagc gggctgctgg gctggccggg   2100
gctttcgtgg ccgccgggcc gctcggtggg acggaagcgt gtggagagac cgccaagggc   2160
tgtagtctgg gtccgcgagc aaggttgccc tgaactgggg gttggggga gcgcagcaaa   2220 atggcggctg ttcccgagtc ttgaatggaa gacgcttgtg aggcgggctg tgaggtcgtt   2280
gaaacaaggt gggggcatg gtgggcggca agaacccaag gtcttgaggc cttcgctaat   2340
gcgggaaagc tcttattcgg gtgagatggg ctggggcacc atctggggac cctgacgtga   2400
agtttgtcac tgactggaga actcggtttg tcgtctgttg cggggcggc agttatggcg   2460 gtgccgttgg gcagtgcacc cgtacctttg ggagcgcgcg ccctcgtcgt gtcgtgacgt   2520
cacccgttct gttggcttat aatgcagggt ggggccacct gccggtaggt gtgcggtagg   2580
cttttctccg tcgcaggacg cagggttcgg gcctagggta ggctctcctg aatcgacagg   2640
cgccggacct ctggtgaggg gagggataag tgaggcgtca gtttctttgg tcggttttat   2700
gtacctatct tcttaagtag ctgaagctcc ggttttgaac tatgcgctcg gggttggcga   2760
gtgtgttttg tgaagttttt taggcacctt ttgaaatgta atcatttggg tcaatatgta   2820
attttcagtg ttagactagt aaattgtccg ctaaattctg gccgttttg gctttttgt   2880 tagacgtgtt gacaattaat catcggcata gtatatcggc atagtataat acgacaaggt   2940
gaggaactaa accatgggat cggccattga acaagatgga ttgcacgcag gttctccggc   3000
cgcttgggtg gagaggctat tcggctatga ctgggcacaa cagacaatcg gctgctctga   3060
tgccgccgtg ttccggctgt cagcgcaggg gcgcccggtt cttttttgtca agaccgacct   3120 gtccggtgcc ctgaatgaac tgcaggacga ggcagcgcgg ctatcgtggc tggccacgac   3180
gggcgttcct tgcgcagctg tgctcgacgt tgtcactgaa gcgggaaggg actggctgct   3240
attgggcgaa gtgccgggc aggatctcct gtcatctcac cttgctcctg ccgagaaagt   3300
atccatcatg gctgatgcaa tgcggcggct gcatacgctt gatccggcta cctgcccatt   3360
cgaccaccaa gcgaaacatc gcatcgagcg agcacgtact cggatggaag ccggtcttgt   3420
cgatcaggat gatctggacg aagagcatca ggggctcgcg ccagccgaac tgttcgccag   3480
gctcaaggcg cgcatgcccg acggcgatga tctcgtcgtg acccatggcg atgcctgctt   3540
gccgaatatc atggtggaaa atggccgctt ttctggattc atcgactgtg ccggctggg   3600 tgtggcggac cgctatcagg acatagcgtt ggctacccgt gatattgctg aagagcttgg   3660
cggcgaatgg gctgaccgct tcctcgtgct ttacggtatc gccgctcccg attcgcagcg   3720
catcgccttc tatcgccttc ttgacgagtt cttctgaggg gatccgctgt aagtctgcag   3780
aaattgatga tctattaaac aataaagatg tccactaaaa tggaagtttt tcctgtcata   3840
ctttgttaag aagggtgaga acagagtacc tacattttga atggaaggat tggagctacg   3900
ggggtggggg tggggtggga ttagataaat gcctgctctt tactgaaggc tctttactat   3960
```

| | |
|---|---|
| tgctttatga taatgtttca tagttggata tcataattta aacaagcaaa accaaattaa | 4020 |
| gggccagctc attcctccca ctcatgatct atagatctat agatctctcg tgggatcatt | 4080 |
| gttttctct tgattcccac tttgtggttc taagtactgt ggtttccaaa tgtgtcagtt | 4140 |
| tcatagcctg aagaacgaga tcagcagcct ctgttccaca tacacttcat tctcagtatt | 4200 |
| gttttgccaa gttctaattc catcagacct cgacctgcag cccctagata acttcgtata | 4260 |
| atgtatgcta tacgaagtta tgctagcatt gtgacttggg catcacttga ctgatggtaa | 4320 |
| tcagttgcag agagaagt gcactgatta agtctgtcca cacagggtct gtctggccag | 4380 |
| gagtgca | 4387 |

<210> SEQ ID NO 10
<211> LENGTH: 1957
<212> TYPE: DNA
<213> ORGANISM: Homo sapiens

<400> SEQUENCE: 10

| | |
|---|---|
| acgtaaccta cggtgtcccg ctaggaaaga gaggtgcgtc aaacagcgac aagttccgcc | 60 |
| cacgtaaaag atgacgcttg atatctccgg agcatttgga taatgtgaca gttggaatgc | 120 |
| agtgatgtcg actctttgcc caccgccatc tccagctgtt gccaagacag agattgcttt | 180 |
| aagtggcaaa tcacctttat tagcagctac ttttgcttac tgggacaata ttcttggtcc | 240 |
| tagagtaagg cacatttggg ctccaaagac agaacaggta cttctcagtg atggagaaat | 300 |
| aactttctt gccaaccaca ctctaaatgg agaaatcctt cgaaatgcag agagtggtgc | 360 |
| tatagatgta aagttttttg tcttgtctga aaagggagtg attattgttt cattaatctt | 420 |
| tgatggaaac tggaatgggg atcgcagcac atatggacta tcaattatac ttccacagac | 480 |
| agaacttagt ttctacctcc cacttcatag agtgtgtgtt gatagattaa cacatataat | 540 |
| ccggaaagga agaatatgga tgcataagga aagacaagaa aatgtccaga agattatctt | 600 |
| agaaggcaca gagagaatgg aagatcaggg tcagagtatt attccaatgc ttactggaga | 660 |
| agtgattcct gtaatggaac tgctttcatc tatgaaatca cacagtgttc ctgaagaaat | 720 |
| agatatagct gatacagtac tcaatgatga tgatattggt gacagctgtc atgaaggctt | 780 |
| tcttctcaag taagaatttt tcttttcata aaagctggat gaagcagata ccatcttatg | 840 |
| ctcacctatg acaagatttg gaagaaagaa ataacagac tgtctactta gattgttcta | 900 |
| gggacattac gtatttgaac tgttgcttaa atttgtgtta tttttcactc attatatttc | 960 |
| tatatatatt tggtgttatt ccatttgcta tttaaagaaa ccgagtttcc atcccagaca | 1020 |
| agaaatcatg gccccttgct tgattctggt ttcttgtttt acttctcatt aaagctaaca | 1080 |
| gaatcctttc atattaagtt gtactgtaga tgaacttaag ttatttaggc gtagaacaaa | 1140 |
| attattcata tttatactga tcttttttcca tccagcagtg gagtttagta cttaagagtt | 1200 |
| tgtgcccttaa aaccagactc cctggattaa tgctgtgtac ccgtgggcaa ggtgcctgaa | 1260 |
| ttctctatac acctatttcc tcatctgtaa aatggcaata atagtaatag tacctaatgt | 1320 |
| gtagggttgt tataagcatt gagtaagata aataatataa agcacttaga acagtgcctg | 1380 |
| gaacataaaa acacttaata atagctcata gctaacattt cctatttaca tttcttctag | 1440 |
| aaatagccag tatttgttga gtgcctacat gttagttcct ttactagttg ctttacatgt | 1500 |
| attatcttat attctgtttt aaagtttctt cacagttaca gatttttcatg aaatttttact | 1560 |
| tttaataaaa gagaagtaaa agtataaagt attcacttttt atgttcacag tcttttcctt | 1620 |

```
taggctcatg atggagtatc agaggcatga gtgtgtttaa cctaagagcc ttaatggctt   1680
gaatcagaag cactttagtc ctgtatctgt tcagtgtcag cctttcatac atcattttaa   1740
atcccatttg actttaagta agtcacttaa tctctctaca tgtcaatttc ttcagctata   1800
aaatgatggt atttcaataa ataaatacat taattaaatg atattatact gactaattgg   1860
gctgttttaa ggctcaataa gaaaatttct gtgaaaggtc tctagaaaat gtaggttcct   1920
atacaaataa aagataacat tgtgcttata aaaaaaa                            1957
```

<210> SEQ ID NO 11
<211> LENGTH: 222
<212> TYPE: PRT
<213> ORGANISM: Homo sapiens

<400> SEQUENCE: 11

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Lys
    210                 215                 220
```

<210> SEQ ID NO 12
<211> LENGTH: 3261
<212> TYPE: DNA
<213> ORGANISM: Homo sapiens

<400> SEQUENCE: 12

```
gggcggggct gcggttgcgg tgcctgcgcc cgcggcggcg gaggcgcagg cggtggcgag    60
tggatatctc cggagcattt ggataatgtg acagttggaa tgcagtgatg tcgactcttt   120
gcccaccgcc atctccagct gttgccaaga cagagattgc tttaagtggc aaatcacctt   180
tattagcagc tactttttgct tactgggaca atattcttgg tcctagagta aggcacattt   240
gggctccaaa gacagaacag gtacttctca gtgatggaga ataacttttt cttgccaacc   300
```

```
acactctaaa tggagaaatc cttcgaaatg cagagagtgg tgctatagat gtaaagtttt    360
ttgtcttgtc tgaaagggga gtgattattg tttcattaat ctttgatgga aactggaatg    420
gggatcgcag cacatatgga ctatcaatta tacttccaca gacagaactt agtttctacc    480
tcccacttca tagagtgtgt gttgatagat taacacatat aatccggaaa ggaagaatat    540
ggatgcataa ggaaagacaa gaaaatgtcc agaagattat cttagaaggc acagagagaa    600
tggaagatca gggtcagagt attattccaa tgcttactgg agaagtgatt cctgtaatgg    660
aactgctttc atctatgaaa tcacacagtg ttcctgaaga aatagatata gctgatacag    720
tactcaatga tgatgatatt ggtgacagct gtcatgaagg ctttcttctc aatgccatca    780
gctcacactt gcaaacctgt ggctgttccg ttgtagtagg tagcagtgca gagaaagtaa    840
ataagatagt cagaacatta tgccttttc tgactccagc agagagaaaa tgctccaggt    900
tatgtgaagc agaatcatca tttaaatatg agtcagggct ctttgtacaa ggcctgctaa    960
aggattcaac tggaagcttt gtgctgcctt tccggcaagt catgtatgct ccatatccca   1020
ccacacacat agatgtggat gtcaatactg tgaagcagat gccaccctgt catgaacata   1080
tttataatca gcgtagatac atgagatccg agctgacagc cttctggaga gccacttcag   1140
aagaagacat ggctcaggat acgatcatct acactgacga aagctttact cctgatttga   1200
atatttttca agatgtctta cacagagaca ctctagtgaa agccttcctg gatcaggtct   1260
ttcagctgaa acctggctta tctctcagaa gtactttcct tgcacagttt ctacttgtcc   1320
ttcacagaaa agccttgaca ctaataaaat atatagaaga cgatacgcag aagggaaaaa   1380 agcccttaa atctcttcgg aacctgaaga tagaccttga tttaacagca gagggcgatc   1440
ttaacataat aatggctctg ctgagaaaa ttaaaccagg cctacactct tttatctttg   1500
gaagaccttt ctacactagt gtgcaagaac gagatgttct aatgactttt taaatgtgta   1560
acttaataag cctattccat cacaatcatg atcgctggta aagtagctca gtggtgtggg   1620
gaaacgttcc cctggatcat actccagaat tctgctctca gcaattgcag ttaagtaagt   1680
tacactacag ttctcacaag agcctgtgag gggatgtcag gtgcatcatt acattgggtg   1740
tctcttttcc tagatttatg cttttgggat acagacctat gtttacaata taataaatat   1800
tattgctatc ttttaaagat ataataatag gatgtaaact tgaccacaac tactgttttt   1860
ttgaaataca tgattcatgg tttacatgtg tcaaggtgaa atctgagttg gcttttacag   1920
atagttgact ttctatcttt tggcattctt tggtgtgtag aattactgta atacttctgc   1980
aatcaactga aaactagagc cttaaatga tttcaattcc acagaaagaa agtgagcttg   2040
aacataggat gagctttaga aagaaaattg atcaagcaga tgtttaattg gaattgatta   2100
ttagatccta ctttgtggat ttagtccctg ggattcagtc tgtagaaatg tctaatagtt   2160
ctctatagtc cttgttcctg gtgaaccaca gttagggtgt tttgtttatt ttattgttct   2220
tgctattgtt gatattctat gtagttgagc tctgtaaaag gaaattgtat tttatgtttt   2280
agtaattgtt gccaactttt taaattaatt ttcattattt ttgagccaaa ttgaaatgtg   2340
cacctcctgt gccttttttc tccttagaaa atctaattac ttggaacaag ttcagatttc   2400
actggtcagt cattttcatc ttgttttctt cttgctaagt cttaccatgt acctgctttg   2460
gcaatcattg caactctgag attataaaat gccttagaga atatactaac taataagatc   2520
tttttttcag aaacagaaaa tagttccttg agtacttcct tcttgcattt ctgcctatgt   2580
ttttgaagtt gttgctgttt gcctgcaata ggctataagg aatagcagga gaaattttac   2640
```

-continued

```
tgaagtgctg ttttcctagg tgctactttg gcagagctaa gttatctttt gttttcttaa    2700
tgcgtttgga ccatttttgct ggctataaaa taactgatta atataattct aacacaatgt   2760
tgacattgta gttacacaaa cacaaataaa tattttattt aaaattctgg aagtaatata    2820
aaagggaaaa tatatttata agaaagggat aaaggtaata gagcccttct gccccccacc    2880
caccaaattt acacaacaaa atgacatgtt cgaatgtgaa aggtcataat agctttccca    2940
tcatgaatca gaaagatgtg gacagcttga tgttttagac aaccactgaa ctagatgact    3000
gttgtactgt agctcagtca tttaaaaaat atataaatac taccttgtag tgtcccatac    3060
tgtgtttttt acatggtaga ttcttattta agtgctaact ggttattttc tttggctggt     3120
ttattgtact gttatacaga atgtaagttg tacagtgaaa taagttatta aagcatgtgt    3180
aaacattgtt atatatcttt tctcctaaat ggagaatttt gaataaaata tatttgaaat    3240
tttaaaaaaa aaaaaaaaa a                                               3261
```

<210> SEQ ID NO 13
<211> LENGTH: 481
<212> TYPE: PRT
<213> ORGANISM: Homo sapiens

<400> SEQUENCE: 13

```
Met Ser Thr Leu Cys Pro Pro Ser Pro Ala Val Ala Lys Thr Glu
1               5                   10                  15

Ile Ala Leu Ser Gly Lys Ser Pro Leu Ala Ala Thr Phe Ala Tyr
                20                  25                  30

Trp Asp Asn Ile Leu Gly Pro Arg Val Arg His Ile Trp Ala Pro Lys
                35                  40                  45

Thr Glu Gln Val Leu Leu Ser Asp Gly Glu Ile Thr Phe Leu Ala Asn
        50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
                100                 105                 110

Ser Ile Ile Leu Pro Gln Thr Glu Leu Ser Phe Tyr Leu Pro Leu His
            115                 120                 125

Arg Val Cys Val Asp Arg Leu Thr His Ile Ile Arg Lys Gly Arg Ile
        130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
```

```
                260                 265                 270
Lys Tyr Glu Ser Gly Leu Phe Val Gln Gly Leu Leu Lys Asp Ser Thr
            275                 280                 285
Gly Ser Phe Val Leu Pro Phe Arg Gln Val Met Tyr Ala Pro Tyr Pro
        290                 295                 300
Thr Thr His Ile Asp Val Asp Val Asn Thr Val Lys Gln Met Pro Pro
305                 310                 315                 320
Cys His Glu His Ile Tyr Asn Gln Arg Arg Tyr Met Arg Ser Glu Leu
                325                 330                 335
Thr Ala Phe Trp Arg Ala Thr Ser Glu Glu Asp Met Ala Gln Asp Thr
            340                 345                 350
Ile Ile Tyr Thr Asp Glu Ser Phe Thr Pro Asp Leu Asn Ile Phe Gln
        355                 360                 365
Asp Val Leu His Arg Asp Thr Leu Val Lys Ala Phe Leu Asp Gln Val
        370                 375                 380
Phe Gln Leu Lys Pro Gly Leu Ser Leu Arg Ser Thr Phe Leu Ala Gln
385                 390                 395                 400
Phe Leu Leu Val Leu His Arg Lys Ala Leu Thr Leu Ile Lys Tyr Ile
                405                 410                 415
Glu Asp Asp Thr Gln Lys Gly Lys Lys Pro Phe Lys Ser Leu Arg Asn
            420                 425                 430
Leu Lys Ile Asp Leu Asp Leu Thr Ala Glu Gly Asp Leu Asn Ile Ile
        435                 440                 445
Met Ala Leu Ala Glu Lys Ile Lys Pro Gly Leu His Ser Phe Ile Phe
        450                 455                 460
Gly Arg Pro Phe Tyr Thr Ser Val Gln Glu Arg Asp Val Leu Met Thr
465                 470                 475                 480
Phe

<210> SEQ ID NO 14
<211> LENGTH: 3356
<212> TYPE: DNA
<213> ORGANISM: Homo sapiens

<400> SEQUENCE: 14
acgtaaccta cggtgtcccg ctaggaaaga gaggtgcgtc aaacagcgac aagttccgcc      60
cacgtaaaag atgacgcttg gtgtgtcagc cgtcccctgct gcccggttgc ttctcttttg    120
ggggcggggt ctagcaagag caggtgtggg tttaggagat atctccggag catttggata    180
atgtgacagt tggaatgcag tgatgtcgac tctttgccca ccgccatctc cagctgttgc    240
caagacagag attgctttaa gtggcaaatc acctttatta gcagctactt ttgcttactg    300
ggacaatatt cttggtccta gagtaaggca catttgggct ccaaagacag aacaggtact    360
tctcagtgat ggagaaataa cttttcttgc caaccacact ctaaatggag aaatccttcg    420
aaatgcagag agtggtgcta tagatgtaaa gttttttgtc ttgtctgaaa agggagtgat    480
tattgtttca ttaatctttg atggaaactg gaatgggat cgcagcacat atggactatc    540
aattatactt ccacagacag aacttagttt ctacctccca cttcatagag tgtgtgttga    600
tagattaaca catataatcc ggaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
```

```
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa   1020
atatgagtca gggctctttg tacaaggcct gctaaaggat tcaactggaa gctttgtgct   1080
gcctttccgg caagtcatgt atgctccata tcccaccaca cacatagatg tggatgtcaa   1140
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtctttcag ctgaaacctg cttatctct    1380 cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actctttat ctttggaaga cctttctaca ctagtgtgca    1620
agaacgagat gttctaatga cttttttaaat gtgtaactta ataagcctat tccatcacaa   1680
tcatgatcgc tggtaaagta gctcagtggt gtggggaaac gttcccctgg atcatactcc   1740
agaattctgc tctcagcaat tgcagttaag taagttacac tacagttctc acaagagcct   1800 gtgagggggat gtcaggtgca tcattacatt gggtgtctct tttcctagat ttatgctttt   1860
gggatacaga cctatgttta caatataata aatattattg ctatctttta aagatataat   1920
aataggatgt aaacttgacc acaactctg tttttttgaa atacatgatt catggtttac     1980
atgtgtcaag gtgaaatctg agttggcttt tacagatagt tgactttcta tcttttggca   2040
ttctttggtg tgtagaatta ctgtaatact tctgcaatca actgaaaact agagccttta   2100
aatgatttca attccacaga aagaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtatttat gtttttagtaa ttgttgccaa cttttaaat    2400 taatttttcat tattttttgag ccaaattgaa atgtgcacct cctgtgcctt ttttctcctt   2460
agaaaatcta attacttgga acaagttcag atttcactgg tcagtcattt tcatcttgtt   2520
ttcttcttgc taagtcttac catgtacctg ctttggcaat cattgcaact ctgagattat   2580
aaaatgcctt agagaatata ctaactaata agatcttttt ttcagaaaca gaaaatagtt   2640
ccttgagtac ttccttcttg catttctgcc tatgttttg aagttgttgc tgtttgcctg    2700
caataggcta taaggaatag caggagaaat tttactgaag tgctgttttc ctaggtgcta   2760
ctttggcaga gctaagttat cttttgtttt cttaatgcgt ttggaccatt ttgctggcta   2820
taaaataact gattaatata attctaacac aatgttgaca ttgtagttac acaaacacaa   2880
ataatatttt tatttaaaat tctggaagta atataaaagg gaaaatatat ttataagaaa   2940
gggataaagg taatagagcc cttctgcccc ccacccacca aatttacaca acaaaatgac   3000
atgttcgaat gtgaaaggtc ataatagctt tcccatcatg aatcagaaag atgtggacag   3060
cttgatgttt tagacaacca ctgaactaga tgactgttgt actgtagctc agtcatttaa   3120
aaaatatata aatactacct tgtagtgtcc catactgtgt ttttttacatg gtagattctt   3180 atttaagtgc taactggtta ttttctttgg ctggtttatt gtactgttat acagaatgta   3240
```

```
agttgtacag tgaaataagt tattaaagca tgtgtaaaca ttgttatata tcttttctcc    3300
taaatggaga attttgaata aaatatattt gaaattttaa aaaaaaaaaa aaaaaa         3356
```

<210> SEQ ID NO 15
<211> LENGTH: 481
<212> TYPE: PRT
<213> ORGANISM: Homo sapiens

<400> SEQUENCE: 15

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ser Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350
```

Ile Ile Tyr Thr Asp Glu Ser Phe Thr Pro Asp Leu Asn Ile Phe Gln
            355                 360                 365

Asp Val Leu His Arg Asp Thr Leu Val Lys Ala Phe Leu Asp Gln Val
        370                 375                 380

Phe Gln Leu Lys Pro Gly Leu Ser Leu Arg Ser Thr Phe Leu Ala Gln
385                 390                 395                 400

Phe Leu Leu Val Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
                420                 425                 430

Leu Lys Ile Asp Leu Asp Leu Thr Ala Glu Gly Asp Leu Asn Ile Ile
            435                 440                 445

Met Ala Leu Ala Glu Lys Ile Lys Pro Gly Leu His Ser Phe Ile Phe
        450                 455                 460

Gly Arg Pro Phe Tyr Thr Ser Val Gln Glu Arg Asp Val Leu Met Thr
465                 470                 475                 480

Phe

<210> SEQ ID NO 16
<211> LENGTH: 3198
<212> TYPE: DNA
<213> ORGANISM: Mus musculus

<400> SEQUENCE: 16
gtgtccgggg cggggcggtc ccggggcggg gcccggagcg ggctgcggtt gcggtccctg      60
cgccggcggt gaaggcgcag cagcggcgag tggctattgc aagcgttcgg ataatgtgag     120
acctggaatg cagtgagacc tgggatgcag ggatgtcgac tatctgcccc ccaccatctc     180
ctgctgttgc caagacagag attgctttaa gtggtgaatc cccttgttg gcggctacct      240
ttgcttactg ggataatatt cttggtccta gagtaaggca tatttgggct ccaaagacag     300
accaagtgct tctcagtgat ggagaaataa ctttcttgc caaccacact ctaaatggag      360
aaattcttcg aaatgcagag agtggggcta tagatgtaaa attttttgtc ttatctgaaa     420
aagggggtaat tattgtttca ttaatcttcg acggaaactg gaatggagat cggagcactt    480
atggactatc aattatactg ccgcagacag agctgagctt ctacctccca cttcacagag     540
tgtgtgttga caggctaaca cacattattc gaaaaggaag aatatggatg cataaggaaa     600
gacaagaaaa tgtccagaaa attgtcttgg aaggcacaga gaggatggaa gatcagggtc     660
agagtatcat tcccatgctt actggggaag tcattcctgt aatggagctg cttgcatcta    720
tgaaatccca cagtgttcct gaagacattg atatagctga tacagtgctc aatgatgatg    780
acattggtga cagctgtcac gaaggcttc ttctcaatgc catcagctca cacctgcaga     840
cctgtggctg ttccgttgta gttggcagca gtgcagagaa agtaaataag atagtaagaa     900
cgctgtgcct ttttctgaca ccagcagaga ggaaatgctc caggctgtgt gaagcagaat     960
cgtccttaa gtacgaatcg ggactctttg tgcaaggctt gctaaaggat gcaacaggca    1020
gttttgtcct acccttccgg caagttatgt atgccccgta ccccaccacg cacattgatg    1080
tggatgtcaa cactgtcaag cagatgccac cgtgtcatga acatattat aatcaacgca    1140
gatacatgag gtcagagctg acagccttct ggagggcaac ttcagaagag acatggcgc     1200
aggacaccat catctacaca gatgagagct tcactcctga tttgaatatt ttccaagatg    1260
tcttacacag agacactcta gtgaaagcct tcctggatca ggtcttccat ttgaagcctg    1320
gcctgtctct caggagtact ttccttgcac agttcctcct cattcttcac agaaaagcct    1380

```
tgacactaat caagtacatc gaggatgata cgcagaaggg gaaaaagccc tttaagtctc    1440
ttcggaacct gaagatagat cttgatttaa cagcagaggg cgatcttaac ataataatgg    1500
ctctagctga gaaaattaag ccaggcctac actctttcat ctttgggaga cctttctaca    1560
ctagtgtaca agaacgtgat gttctaatga ccttttgacc gtgtggtttg ctgtgtctgt    1620
ctcttcacag tcacacctgc tgttacagtg tctcagcagt gtgtgggcac atccttcctc    1680
ccgagtcctg ctgcaggaca gggtacacta cacttgtcag tagaagtctg tacctgatgt    1740
caggtgcatc gttacagtga atgactcttc ctagaataga tgtactcttt tagggcctta    1800
tgtttacaat tatcctaagt actattgctg tcttttaaag atatgaatga tggaatatac    1860
acttgaccat aactgctgat tggttttttg ttttgttttg tttgttttct tggaaactta    1920
tgattcctgg tttacatgta ccacactgaa accctcgtta gctttacaga taaagtgtga    1980
gttgacttcc tgcccctctg tgttctgtgg tatgtccgat tacttctgcc acagctaaac    2040
attagagcat ttaaagtttg cagttcctca gaaaggaact tagtctgact acagattagt    2100
tcttgagaga agacactgat agggcagagc tgtaggtgaa atcagttgtt agcccttcct    2160
ttatagacgt agtccttcag attcggtctg tacagaaatg ccgaggggtc atgcatgggc    2220
cctgagtatc gtgacctgtg acaagttttt tgttggttta ttgtagttct gtcaaagaaa    2280
gtggcatttg tttttataat tgttgccaac tttaaggtt aattttcatt attttttgagc     2340 cgaattaaaa tgcgcacctc ctgtgccttt cccaatcttg gaaaatataa tttcttggca    2400
gagggtcaga tttcagggcc cagtcacttt catctgacca ccctttgcac ggctgccgtg    2460
tgcctggctt agattagaag tccttgttaa gtatgtcaga gtacattcgc tgataagatc    2520
tttgaagagc agggaagcgt cttgcctctt cctttggtt tctgcctgta ctctggtgtt     2580
tcccgtgtca cctgcatcat aggaacagca gagaaatctg acccagtgct attttttctag    2640 gtgctactat ggcaaactca agtggtctgt ttctgttcct gtaacgttcg actatctcgc    2700
tagctgtgaa gtactgatta gtggagttct gtgcaacagc agtgtaggag tatacacaaa    2760
cacaaatatg tgtttctatt taaaactgtg gacttagcat aaaaagggag aatatattta    2820
ttttttacaa aagggataaa aatgggcccc gttcctcacc caccagattt agcgagaaaa    2880
agctttctat tctgaaaggt cacggtggct ttggcattac aaatcagaac aacacacact    2940
gaccatgatg gcttgtgaac taactgcaag gcactccgtc atggtaagcg agtaggtccc    3000
acctcctagt gtgccgctca ttgctttaca cagtagaatc ttatttgagt gctaattgtt    3060
gtctttgctg ctttactgtg ttgttataga aaatgtaagc tgtacagtga ataagttatt    3120
gaagcatgtg taaacactgt tatatatctt ttctcctaga tggggaattt tgaataaaat    3180
acctttgaaa ttctgtgt                                                  3198
```

<210> SEQ ID NO 17
<211> LENGTH: 481
<212> TYPE: PRT
<213> ORGANISM: Mus musculus

<400> SEQUENCE: 17

Met Ser Thr Ile Cys Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

```
Thr Asp Gln Val Leu Leu Ser Asp Gly Glu Ile Thr Phe Leu Ala Asn
 50                      55                  60
His Thr Leu Asn Gly Glu Ile Leu Arg Asn Ala Glu Ser Gly Ala Ile
 65                  70                  75                  80
Asp Val Lys Phe Phe Val Leu Ser Glu Lys Gly Val Ile Ile Val Ser
                 85                  90                  95
Leu Ile Phe Asp Gly Asn Trp Asn Gly Asp Arg Ser Thr Tyr Gly Leu
                100                 105                 110
Ser Ile Ile Leu Pro Gln Thr Glu Leu Ser Phe Tyr Leu Pro Leu His
            115                 120                 125
Arg Val Cys Val Asp Arg Leu Thr His Ile Ile Arg Lys Gly Arg Ile
        130                 135                 140
Trp Met His Lys Glu Arg Gln Glu Asn Val Gln Lys Ile Val Leu Glu
145                 150                 155                 160
Gly Thr Glu Arg Met Glu Asp Gln Gly Gln Ser Ile Ile Pro Met Leu
                165                 170                 175
Thr Gly Glu Val Ile Pro Val Met Glu Leu Leu Ala Ser Met Lys Ser
            180                 185                 190
His Ser Val Pro Glu Asp Ile Asp Ile Ala Asp Thr Val Leu Asn Asp
        195                 200                 205
Asp Asp Ile Gly Asp Ser Cys His Glu Gly Phe Leu Leu Asn Ala Ile
    210                 215                 220
Ser Ser His Leu Gln Thr Cys Gly Cys Ser Val Val Gly Ser Ser
225                 230                 235                 240
Ala Glu Lys Val Asn Lys Ile Val Arg Thr Leu Cys Leu Phe Leu Thr
                245                 250                 255
Pro Ala Glu Arg Lys Cys Ser Arg Leu Cys Glu Ala Glu Ser Ser Phe
            260                 265                 270
Lys Tyr Glu Ser Gly Leu Phe Val Gln Gly Leu Leu Lys Asp Ala Thr
        275                 280                 285
Gly Ser Phe Val Leu Pro Phe Arg Gln Val Met Tyr Ala Pro Tyr Pro
    290                 295                 300
Thr Thr His Ile Asp Val Asp Val Asn Thr Val Lys Gln Met Pro Pro
305                 310                 315                 320
Cys His Glu His Ile Tyr Asn Gln Arg Arg Tyr Met Arg Ser Glu Leu
                325                 330                 335
Thr Ala Phe Trp Arg Ala Thr Ser Glu Glu Asp Met Ala Gln Asp Thr
            340                 345                 350
Ile Ile Tyr Thr Asp Glu Ser Phe Thr Pro Asp Leu Asn Ile Phe Gln
        355                 360                 365
Asp Val Leu His Arg Asp Thr Leu Val Lys Ala Phe Leu Asp Gln Val
    370                 375                 380
Phe His Leu Lys Pro Gly Leu Ser Leu Arg Ser Thr Phe Leu Ala Gln
385                 390                 395                 400
Phe Leu Leu Ile Leu His Arg Lys Ala Leu Thr Leu Ile Lys Tyr Ile
                405                 410                 415
Glu Asp Asp Thr Gln Lys Gly Lys Lys Pro Phe Lys Ser Leu Arg Asn
            420                 425                 430
Leu Lys Ile Asp Leu Asp Leu Thr Ala Glu Gly Asp Leu Asn Ile Ile
        435                 440                 445
Met Ala Leu Ala Glu Lys Ile Lys Pro Gly Leu His Ser Phe Ile Phe
    450                 455                 460
```

Gly Arg Pro Phe Tyr Thr Ser Val Gln Glu Arg Asp Val Leu Met Thr
465                 470                 475                 480

Phe

<210> SEQ ID NO 18
<211> LENGTH: 3435
<212> TYPE: DNA
<213> ORGANISM: Rattus norvegicus

<400> SEQUENCE: 18

| | |
|---|---|
| cgtttgtagt gtcagccatc ccaattgcct gttccttctc tgtgggagtg gtgtctagac | 60 |
| agtccaggca gggtatgcta ggcaggtgcg ttttggttgc ctcagatcgc aacttgactc | 120 |
| cataacggtg accaaagaca aagaaggaa accagattaa aaagaaccgg acacagaccc | 180 |
| ctgcagaatc tggagcggcc gtggttgggg gcggggctac gacggggcgg actcggggc | 240 |
| gtgggagggc ggggccgggg cggggcccgg agccggctgc ggttgcggtc cctgcgccgg | 300 |
| cggtgaaggc gcagcggcgg cgagtggcta ttgcaagcgt ttggataatg tgagacctgg | 360 |
| gatgcaggga tgtcgactat ctgcccccca ccatctcctg ctgttgccaa gacagagatt | 420 |
| gctttaagtg gtgaatcacc cttgttggcg gctacctttg cttactggga taatattctt | 480 |
| ggtcctagag taaggcacat ttgggctcca agacagacc aagtactcct cagtgatgga | 540 |
| gaaatcactt tccttgccaa ccacactctg aatggagaaa ttcttcggaa tgcggagagt | 600 |
| ggggcaatag atgtaaagtt ttttgtctta tctgaaaagg gcgtcattat tgtttcatta | 660 |
| atcttcgacg ggaactggaa cggagatcgg agcacttacg gactatcaat tatactgccg | 720 |
| cagacggagc tgagtttcta cctcccactg cacagagtgt gtgttgacag gctaacgcac | 780 |
| atcattcgaa aaggaaggat atggatgcac aaggaaagac aagaaaatgt ccagaaaatt | 840 |
| gtcttggaag gcaccgagag gatggaagat cagggtcaga gtatcatccc tatgcttact | 900 |
| ggggaggtca tccctgtgat ggagctgctt gcgtctatga gatcacacag tgttcctgaa | 960 |
| gacctcgata tagctgatac agtactcaat gatgatgaca ttggtgacag ctgtcatgaa | 1020 |
| ggctttcttc tcaatgccat cagctcacat ctgcagacct gcggctgttc tgtggtggta | 1080 |
| ggcagcagtg cagagaaagt aaataagata gtaagaacac tgtgcctttt tctgacacca | 1140 |
| gcagagagga agtgctccag gctgtgtgaa gccgaatcgt cctttaaata cgaatctgga | 1200 |
| ctctttgtac aaggcttgct aaaggatgcg actggcagtt ttgtactacc tttccggcaa | 1260 |
| gttatgtatg ccccttatcc caccacacac atcgatgtgg atgtcaacac tgtcaagcag | 1320 |
| atgccaccgt gtcatgaaca tatttataat caacgcagat acatgaggtc agagctgaca | 1380 |
| gccttctgga gggcaacttc agaagaggac atggctcagg acaccatcat ctacacagat | 1440 |
| gagagcttca ctcctgattt gaatatttc caagatgtct tacacagaga cactctagtg | 1500 |
| aaagcctttc tggatcaggt cttccatttg aagcctggcc tgtctctcag gagtactttc | 1560 |
| cttgcacagt tcctcctcat tcttcacaga aaagccttga cactaatcaa gtacatagag | 1620 |
| gatgacacgc agaaggggaa aaagcccttt aagtctcttc ggaacctgaa gatagatctt | 1680 |
| gatttaacag cagagggcga ccttaacata ataatggctc tagctgagaa aattaagcca | 1740 |
| ggcctacact ctttcatctt cgggagacct ttctacacta gtgtccaaga acgtgatgtt | 1800 |
| ctaatgactt tttaaacatg tggtttgctc cgtgtgtctc atgacagtca cacttgctgt | 1860 |
| tacagtgtct cagcgctttg gacacatcct tcctccaggg tcctgccgca ggacacgtta | 1920 |
| cactacactt gtcagtagag gtctgtacca gatgtcaggt acatcgttgt agtgaatgtc | 1980 |

```
tcttttccta gactagatgt accctcgtag ggacttatgt ttacaaccct cctaagtact    2040
agtgctgtct tgtaaggata cgaatgaagg gatgtaaact tcaccacaac tgctggttgg    2100
ttttgttgtt tttgttttt gaaacttata attcatggtt tacatgcatc acactgaaac    2160
cctagttagc ttttacagg taagctgtga gttgactgcc tgtccctgtg ttctctggcc    2220
tgtacgatct gtggcgtgta ggatcacttt tgcaacaact aaaaactaaa gcactttgtt    2280
tgcagttcta cagaaagcaa cttagtctgt ctgcagattc gttttgaaa gaagacatga    2340
gaaagcggag ttttaggtga agtcagttgt tggatcttcc tttatagact tagtccttta    2400
gatgtggtct gtatagacat gcccaaccat catgcatggg cactgaatat cgtgaactgt    2460
ggtatgcttt ttgttggttt attgtacttc tgtcaaagaa agtggcattg gtttttataa    2520
ttgttgccaa gttttaaggt taattttcat tattttgag ccaaattaaa atgtgcacct    2580
cctgtgcctt tcccaatctt ggaaaatata atttcttggc agaaggtcag atttcagggc    2640
ccagtcactt tcgtctgact tccctttgca cagtccgcca tgggcctggc ttagaagttc    2700
ttgtaaacta tgccagagag tacattcgct gataaaatct tctttgcaga gcaggagagc    2760
ttcttgcctc tttcctttca tttctgcctg gactttggtg ttctccacgt tccctgcatc    2820
ctaaggacag caggagaact ctgaccccag tgctatttct ctaggtgcta ttgtggcaaa    2880
ctcaagcggt ccgtctctgt ccctgtaacg ttcgtacctt gctggctgtg aagtactgac    2940
tggtaaagct ccgtgctaca gcagtgtagg gtatacacaa acacaagtaa gtgttttatt    3000
taaaactgtg gacttagcat aaaaagggag actatattta ttttttacaa aagggataaa    3060
aatgaaccc tttcctcacc caccagattt agtcagaaaa aaacattcta ttctgaaagg    3120
tcacagtggt tttgacatga cacatcagaa caacgcacac tgtccatgat ggcttatgaa    3180
ctccaagtca ctccatcatg gtaaatgggt agatccctcc ttctagtgtg ccacaccatt    3240
gcttcccaca gtagaatctt atttaagtgc taagtgttgt ctctgctggt ttactctgtt    3300
gttttagaga atgtaagttg tatagtgaat aagttattga agcatgtgta aacactgtta    3360
tacatctttt ctcctagatg gggaatttgg aataaaatac ctttaaaatt caaaaaaaaa    3420
aaaaaaaaaa aaaaa                                                    3435
```

<210> SEQ ID NO 19
<211> LENGTH: 481
<212> TYPE: PRT
<213> ORGANISM: Rattus norvegicus

<400> SEQUENCE: 19

```
Met Ser Thr Ile Cys Pro Pro Ser Pro Ala Val Ala Lys Thr Glu
1               5                  10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Val Ser
                85                  90                  95

Leu Ile Phe Asp Gly Asn Trp Asn Gly Asp Arg Ser Tyr Gly Leu
            100                 105                 110
```

```
Ser Ile Ile Leu Pro Gln Thr Glu Leu Ser Phe Tyr Leu Pro Leu His
            115                 120                 125
Arg Val Cys Val Asp Arg Leu Thr His Ile Ile Arg Lys Gly Arg Ile
        130                 135                 140
Trp Met His Lys Glu Arg Gln Glu Asn Val Gln Lys Ile Val Leu Glu
145                 150                 155                 160
Gly Thr Glu Arg Met Glu Asp Gln Gly Gln Ser Ile Ile Pro Met Leu
                165                 170                 175
Thr Gly Glu Val Ile Pro Val Met Glu Leu Leu Ala Ser Met Arg Ser
            180                 185                 190
His Ser Val Pro Glu Asp Leu Asp Ile Ala Asp Thr Val Leu Asn Asp
        195                 200                 205
Asp Asp Ile Gly Asp Ser Cys His Glu Gly Phe Leu Leu Asn Ala Ile
    210                 215                 220
Ser Ser His Leu Gln Thr Cys Gly Cys Ser Val Val Gly Ser Ser
225                 230                 235                 240
Ala Glu Lys Val Asn Lys Ile Val Arg Thr Leu Cys Leu Phe Leu Thr
                245                 250                 255
Pro Ala Glu Arg Lys Cys Ser Arg Leu Cys Glu Ala Glu Ser Ser Phe
            260                 265                 270
Lys Tyr Glu Ser Gly Leu Phe Val Gln Gly Leu Leu Lys Asp Ala Thr
        275                 280                 285
Gly Ser Phe Val Leu Pro Phe Arg Gln Val Met Tyr Ala Pro Tyr Pro
    290                 295                 300
Thr Thr His Ile Asp Val Asp Val Asn Thr Val Lys Gln Met Pro Pro
305                 310                 315                 320
Cys His Glu His Ile Tyr Asn Gln Arg Arg Tyr Met Arg Ser Glu Leu
                325                 330                 335
Thr Ala Phe Trp Arg Ala Thr Ser Glu Glu Asp Met Ala Gln Asp Thr
            340                 345                 350
Ile Ile Tyr Thr Asp Glu Ser Phe Thr Pro Asp Leu Asn Ile Phe Gln
        355                 360                 365
Asp Val Leu His Arg Asp Thr Leu Val Lys Ala Phe Leu Asp Gln Val
    370                 375                 380
Phe His Leu Lys Pro Gly Leu Ser Leu Arg Ser Thr Phe Leu Ala Gln
385                 390                 395                 400
Phe Leu Leu Ile Leu His Arg Lys Ala Leu Thr Leu Ile Lys Tyr Ile
                405                 410                 415
Glu Asp Asp Thr Gln Lys Gly Lys Lys Pro Phe Lys Ser Leu Arg Asn
            420                 425                 430
Leu Lys Ile Asp Leu Asp Leu Thr Ala Glu Gly Asp Leu Asn Ile Ile
        435                 440                 445
Met Ala Leu Ala Glu Lys Ile Lys Pro Gly Leu His Ser Phe Ile Phe
    450                 455                 460
Gly Arg Pro Phe Tyr Thr Ser Val Gln Glu Arg Asp Val Leu Met Thr
465                 470                 475                 480
Phe

<210> SEQ ID NO 20
<211> LENGTH: 100
<212> TYPE: DNA
<213> ORGANISM: Mus musculus

<400> SEQUENCE: 20
```

| | |
|---|---|
| gaaccgcggc gcgtcaagca gagacgagtt ccgcccacgt gaaagatggc gtttgtagtg | 60 |
| acagccatcc caattgccct ttccttctag gtggaaagtg | 100 |

<210> SEQ ID NO 21
<211> LENGTH: 2648
<212> TYPE: DNA
<213> ORGANISM: Artificial Sequence
<220> FEATURE:
<223> OTHER INFORMATION: floxed neo cassette of 8026 plus lox sites

<400> SEQUENCE: 21

| | |
|---|---|
| ataacttcgt ataatgtatg ctatacgaag ttatatgcat ggcctccgcg ccgggttttg | 60 |
| gcgcctcccg cgggcgcccc cctcctcacg gcgagcgctg ccacgtcaga cgaagggcgc | 120 |
| agcgagcgtc ctgatccttc cgcccggacg ctcaggacag cggcccgctg ctcataagac | 180 |
| tcggccttag aaccccagta tcagcagaag gacattttag gacgggactt gggtgactct | 240 |
| agggcactgg ttttctttcc agagagcgga acaggcgagg aaaagtagtc ccttctcggc | 300 |
| gattctgcgg agggatctcc gtggggcggt gaacgccgat gattatataa ggacgcgccg | 360 |
| ggtgtggcac agctagttcc gtcgcagccg ggatttgggt cgcggttctt gtttgtggat | 420 |
| cgctgtgatc gtcacttggt gagtagcggg ctgctgggct ggccggggct ttcgtggccg | 480 |
| ccgggccgct cggtgggacg gaagcgtgtg gagagaccgc caagggctgt agtctgggtc | 540 |
| cgcgagcaag gttgccctga actgggggtt ggggggagcg cagcaaaatg gcggctgttc | 600 |
| ccgagtcttg aatggaagac gcttgtgagg cgggctgtga ggtcgttgaa caaggtggg | 660 |
| gggcatggtg ggcggcaaga acccaaggtc ttgaggcctt cgctaatgcg ggaaagctct | 720 |
| tattcgggtg agatgggctg gggcaccatc tggggaccct gacgtgaagt ttgtcactga | 780 |
| ctggagaact cggtttgtcg tctgttgcgg gggcggcagt tatggcggtg ccgttgggca | 840 |
| gtgcacccgt acctttggga gcgcgcgccc tcgtcgtgtc gtgacgtcac ccgttctgtt | 900 |
| ggcttataat gcagggtggg gccacctgcc ggtaggtgtg cggtaggctt ttctccgtcg | 960 |
| caggacgcag ggttcgggcc tagggtaggc tctcctgaat cgacaggcgc cggacctctg | 1020 |
| gtgaggggag ggataagtga ggcgtcagtt tctttggtcg gttttatgta cctatcttct | 1080 |
| taagtagctg aagctccggt tttgaactat gcgctcgggg ttggcgagtg tgttttgtga | 1140 |
| agttttttag gcaccttttg aaatgtaatc atttgggtca atatgtaatt ttcagtgtta | 1200 |
| gactagtaaa ttgtccgcta aattctggcc gttttttggct tttttgttag acgtgttgac | 1260 |
| aattaatcat cggcatagta tatcggcata gtataatacg acaaggtgag gaactaaacc | 1320 |
| atgggatcgg ccattgaaca agatggattg cacgcaggtt ctccggccgc ttgggtggag | 1380 |
| aggctattcg gctatgactg gcacaacag acaatcggct gctctgatgc cgccgtgttc | 1440 |
| cggctgtcag cgcaggggcg cccggttctt tttgtcaaga ccgacctgtc cggtgccctg | 1500 |
| aatgaactgc aggacgaggc agcgcggcta tcgtggctgg ccacgacggg cgttccttgc | 1560 |
| gcagctgtgc tcgacgttgt cactgaagcg ggaagggact ggctgctatt gggcgaagtg | 1620 |
| ccggggcagg atctcctgtc atctcacctt gctcctgccg agaaagtatc catcatggct | 1680 |
| gatgcaatgc ggcggctgca tacgcttgat ccggctacct gcccattcga ccaccaagcg | 1740 |
| aaacatcgca tcgagcgagc acgtactcgg atggaagccg gtcttgtcga tcaggatgat | 1800 |
| ctggacgaag agcatcaggg gctcgcgcca gccgaactgt tcgccaggct caaggcgcgc | 1860 |
| atgcccgacg gcgatgatct cgtcgtgacc catggcgatg cctgcttgcc gaatatcatg | 1920 |
| gtggaaaatg gccgcttttc tggattcatc gactgtggcc ggctgggtgt ggcggaccgc | 1980 |

```
tatcaggaca tagcgttggc tacccgtgat attgctgaag agcttggcgg cgaatgggct    2040
gaccgcttcc tcgtgcttta cggtatcgcc gctcccgatt cgcagcgcat cgccttctat    2100
cgccttcttg acgagttctt ctgagggat ccgctgtaag tctgcagaaa ttgatgatct     2160
```
(… continued)
```
cgccttcttg acgagttctt ctgagggdat ccgctgtaag tctgcagaaa ttgatgatct    2160
attaaacaat aaagatgtcc actaaaatgg aagttttttcc tgtcatactt tgttaagaag   2220
ggtgagaaca gagtacctac attttgaatg gaaggattgg agctacgggg gtggggtgg    2280 ggtgggatta gataaatgcc tgctctttac tgaaggctct ttactattgc tttatgataa   2340
tgtttcatag ttggatatca taatttaaac aagcaaaacc aaattaaggg ccagctcatt   2400
cctcccactc atgatctata gatctataga tctctcgtgg gatcattgtt tttctcttga   2460
ttcccacttt gtggttctaa gtactgtggt ttccaaatgt gtcagtttca tagcctgaag   2520
aacgagatca gcagcctctg ttccacatac acttcattct cagtattgtt ttgccaagtt   2580
ctaattccat cagacctcga cctgcagccc ctagataact tcgtataatg tatgctatac   2640
gaagttat                                                            2648
```

```
<210> SEQ ID NO 22
<211> LENGTH: 100
<212> TYPE: DNA
<213> ORGANISM: Mus musculus

<400> SEQUENCE: 22
attgtgactt gggcatcact tgactgatgg taatcagttg cagagagaga agtgcactga    60
ttaagtctgt ccacacaggg tctgtctggc caggagtgca                         100

<210> SEQ ID NO 23
<211> LENGTH: 100
<212> TYPE: DNA
<213> ORGANISM: Mus musculus

<400> SEQUENCE: 23
gaaccgcggc gcgtcaagca gagacgagtt ccgcccacgt gaaagatggc gtttgtagtg    60
acagccatcc caattgccct ttccttctag gtggaaagtg                         100

<210> SEQ ID NO 24
<211> LENGTH: 2648
<212> TYPE: DNA
<213> ORGANISM: Artificial Sequence
<220> FEATURE:
<223> OTHER INFORMATION: floxed cassette of 8028 plus lox sites

<400> SEQUENCE: 24
ataacttcgt ataatgtatg ctatacgaag ttatatgcat ggcctccgcg ccgggttttg    60
gcgcctcccg cgggcgcccc cctcctcacg gcgagcgctg ccacgtcaga cgaagggcgc   120
agcgagcgtc ctgatccttc cgcccggacg ctcaggacag cggcccgctg ctcataagac   180
tcggccttag aacccagta tcagcagaag gacattttag gacgggactt gggtgactct    240
agggcactgg ttttctttcc agagagcgga acaggcgagg aaaagtagtc ccttctcggc   300
gattctgcgg agggatctcc gtggggcggt gaacgccgat gattatataa ggacgcgccg   360
ggtgtggcac agctagttcc gtcgcagccg ggatttgggt cgcggttctt gtttgtggat   420
cgctgtgatc gtcacttggt gagtagcggg ctgctgggct ggccggggct ttcgtggccg   480
ccgggccgct cggtgggacg gaagcgtgtg gagagaccgc caagggctgt agtctgggtc   540
cgcgagcaag gttgccctga actgggggtt gggggggagcg cagcaaaatg gcggctgttc   600
```

```
ccgagtcttg aatggaagac gcttgtgagg cgggctgtga ggtcgttgaa acaaggtggg      660
gggcatggtg ggcggcaaga acccaaggtc ttgaggcctt cgctaatgcg ggaaagctct      720
tattcgggtg agatgggctg gggcaccatc tggggaccct gacgtgaagt tgtcactga       780
ctggagaact cggtttgtcg tctgttgcgg ggcggcagt tatggcggtg ccgttgggca       840
gtgcacccgt acctttggga gcgcgcgccc tcgtcgtgtc gtgacgtcac ccgttctgtt      900
ggcttataat gcagggtggg gccacctgcc ggtaggtgtg cggtaggctt ttctccgtcg      960
caggacgcag ggttcgggcc tagggtaggc tctcctgaat cgacaggcgc cggacctctg     1020
gtgaggggag ggataagtga ggcgtcagtt tctttggtcg gttttatgta cctatcttct     1080
taagtagctg aagctccggt tttgaactat gcgctcgggg ttggcgagtg tgttttgtga     1140
agttttttag gcacctttg aaatgtaatc atttgggtca atatgtaatt ttcagtgtta      1200
gactagtaaa ttgtccgcta aattctggcc gttttttggct tttttgttag acgtgttgac    1260
aattaatcat cggcatagta tatcggcata gtataaatcg acaaggtgag gaactaaacc     1320
atgggatcgg ccattgaaca agatggattg cacgcaggtt ctccggccgc ttgggtggag     1380
aggctattcg gctatgactg ggcacaacag acaatcggct gctctgatgc cgccgtgttc     1440
cggctgtcag cgcaggggcg cccggttctt tttgtcaaga ccgacctgtc cggtgccctg     1500
aatgaactgc aggacgaggc agcgcggcta tcgtggctgg ccacgacggg cgttccttgc     1560
gcagctgtgc tcgacgttgt cactgaagcg ggaagggact ggctgctatt gggcgaagtg     1620
ccggggcagg atctcctgtc atctcacctt gctcctgccg agaaagtatc catcatggct     1680
gatgcaatgc ggcggctgca tacgcttgat ccggctacct gcccattcga ccaccaagcg     1740
aaacatcgca tcgagcgagc acgtactcgg atggaagccg gtcttgtcga tcaggatgat     1800
ctggacgaag agcatcaggg gctcgcgcca gccgaactgt tcgccaggct caaggcgcgc     1860
atgcccgacg gcgatgatct cgtcgtgacc catggcgatg cctgcttgcc gaatatcatg     1920
gtggaaaatg gccgcttttc tggattcatc gactgtggcc ggctgggtgt ggcggaccgc     1980
tatcaggaca tagcgttggc tacccgtgat attgctgaag agcttggcgg cgaatgggct     2040
gaccgcttcc tcgtgcttta cggtatcgcc gctcccgatt cgcagcgcat cgccttctat     2100
cgccttcttg acgagttctt ctgaggggat ccgctgtaag tctgcagaaa ttgatgatct     2160
attaaacaat aaagatgtcc actaaaatgg aagttttttcc tgtcatactt tgttaagaag    2220
ggtgagaaca gagtacctac attttgaatg aaggattgg agctacgggg gtgggggtgg      2280
ggtgggatta gataaatgcc tgctctttac tgaaggctct ttactattgc tttatgataa     2340
tgtttcatag ttggatatca taatttaaac aagcaaaacc aaattaaggg ccagctcatt     2400
cctcccactc atgatctata gatctataga tctctcgtgg gatcattgtt tttctcttga    2460
ttcccacttt gtggttctaa gtactgtggt ttccaaatgt gtcagtttca tagcctgaag     2520
aacgagatca gcagcctctg ttccacatac acttcattct cagtattgtt ttgccaagtt     2580
ctaattccat cagacctcga cctgcagccc ctagataact tcgtataatg tatgctatac     2640
gaagttat                                                              2648
```

<210> SEQ ID NO 25
<211> LENGTH: 100
<212> TYPE: DNA
<213> ORGANISM: Mus musculus

<400> SEQUENCE: 25

```
attgtgactt gggcatcact tgactgatgg taatcagttg cagagagaga agtgcactga       60
```

```
ttaagtctgt ccacacaggg tctgtctggc caggagtgca                          100
```

<210> SEQ ID NO 26
<211> LENGTH: 680
<212> TYPE: DNA
<213> ORGANISM: Mus musculus

<400> SEQUENCE: 26

```
ccagtagcag cacccacgtc caccttctgt ctagtaatgt ccaacacctc cctcagtcca    60
aacactgctc tgcatccatg tggctcccat ttatacctga agcacttgat ggggcctcaa   120
tgttttacta gagcccaccc ccctgcaact ctgagaccct ctggatttgt ctgtcagtgc   180
ctcactgggg cgttggataa tttcttaaaa ggtcaagttc cctcagcagc attctctgag   240
cagtctgaag atgtgtgctt ttcacagttc aaatccatgt ggctgtttca cccacctgcc   300
tggccttggg ttatctatca ggacctagcc tagaagcagg tgtgtggcac ttaacaccta   360
agctgagtga ctaactgaac actcaagtgg atgccatctt tgtcacttct tgactgtgac   420
acaagcaact cctgatgcca agccctgcc caccctctc atgcccatat ttggacatgg    480
tacaggtcct cactggccat ggtctgtgag gtcctggtcc tctttgactt cataattcct   540
agggccact agtatctata agaggaagag ggtgctggct cccaggccac agcccacaaa   600
attccacctg ctcacaggtt ggctggctcg acccaggtgg tgtcccctgc tctgagccag   660
ctcccggcca agccagcacc                                               680
```

<210> SEQ ID NO 27
<211> LENGTH: 1052
<212> TYPE: DNA
<213> ORGANISM: Mus musculus

<400> SEQUENCE: 27

```
tgccatcatc acaggatgtc cttccttctc cagaagacag actggggctg aaggaaaagc    60
cggccaggct cagaacgagc cccactaatt actgcctcca acagctttcc actcactgcc   120
cccagcccaa catccccttt ttaactggga agcattccta ctctccattg tacgcacacg   180
ctcggaagcc tggctgtggg tttgggcatg agaggcaggg acaacaaaac cagtatatat   240
gattataact ttttcctgtt tccctatttc caaatggtcg aaaggaggaa gttaggtcta   300
cctaagctga atgtattcag ttagcaggag aaatgaaatc ctatacgttt aatactagag   360
gagaaccgcc ttagaatatt tatttcattg gcaatgactc caggactaca cagcgaaatt   420
gtattgcatg tgctgccaaa atactttagc tctttccttc gaagtacgtc ggatcctgta   480
attgagacac cgagtttagg tgactagggt tttcttttga ggaggagtcc cccaccccgc   540
cccgctctgc cgcgacagga agctagcgat ccggaggact agaatacaa tcgtagtgtg    600
ggtaaacatg gagggcaagc gcctgcaaag ggaagtaaga agattcccag tccttgttga   660
aatccatttg caaacagagg aagctgccgc gggtcgcagt cggtgggggg aagccctgaa   720
ccccacgctg cacggctggg ctggccaggt gcggccacgc cccatcgcg gcggctggta    780
ggagtgaatc agaccgtcag tattggtaaa gaagtctgcg gcagggcagg gaggggaag    840
agtagtcagt cgctcgctca ctcgctcgct cgcacagaca ctgctgcagt gacactcggc   900
cctccagtgt cgcggagacg caagagcagc gcgcagcacc tgtccgcccg gagcgagccc   960
ggcccgcggc cgtagaaaag gagggaccgc cgaggtgcgc gtcagtactg ctcagcccgg  1020
cagggacgcg ggaggatgtg gactgggtgg ac                                1052
```

<210> SEQ ID NO 28
<211> LENGTH: 2008
<212> TYPE: DNA
<213> ORGANISM: Mus musculus

<400> SEQUENCE: 28

| | | | | | |
|---|---|---|---|---|---|
| gtggtgctga | ctcagcatcg | gttaataaac | cctctgcagg | aggctggatt | tcttttgttt | 60 |
| aattatcact | tggaccttc | tgagaactct | taagaattgt | tcattcgggt | tttttttgttt | 120 |
| tgttttggtt | tggttttttt | gggttttttt | ttttttttt | ttttggttt | ttggagacag | 180 |
| ggtttctctg | tatatagccc | tggcacaaga | gcaagctaac | agcctgtttc | ttcttggtgc | 240 |
| tagcgcccc | tctggcagaa | aatgaaataa | caggtggacc | tacaacccc | cccccccc | 300 |
| ccagtgtatt | ctactcttgt | ccccggtata | aatttgattg | ttccgaacta | cataaattgt | 360 |
| agaaggattt | tttagatgca | catatcattt | tctgtgatac | cttccacaca | ccctccccc | 420 |
| ccaaaaaaat | ttttctggga | agtttcttg | aaaggaaaac | agaagaacaa | gcctgtcttt | 480 |
| atgattgagt | tgggcttttg | ttttgctgtg | tttcatttct | tcctgtaaac | aaatactcaa | 540 |
| atgtccactt | cattgtatga | ctaagttggt | atcattaggt | tgggtctggg | tgtgtgaatg | 600 |
| tgggtgtgga | tctggatgtg | ggtggtgtg | tatgcccgt | gtgtttagaa | tactagaaaa | 660 |
| gataccacat | cgtaaacttt | tgggagagat | gattttaaa | aatgggggtg | gggtgaggg | 720 |
| gaacctgcga | tgaggcaagc | aagataaggg | gaagacttga | gttctgtga | tctaaaaagt | 780 |
| cgctgtgatg | ggatgctggc | tataaatggg | cccttagcag | cattgtttct | gtgaattgga | 840 |
| ggatccctgc | tgaaggcaaa | agaccattga | aggaagtacc | gcatctggtt | tgttttgtaa | 900 |
| tgagaagcag | gaatgcaagg | tccacgctct | taataataaa | caaacaggac | attgtatgcc | 960 |
| atcatcacag | gatgtccttc | cttctccaga | agacagactg | gggctgaagg | aaaagccggc | 1020 |
| caggctcaga | acgagcccca | ctaattactg | cctccaacag | cttccactc | actgccccca | 1080 |
| gcccaacatc | ccctttttaa | ctgggaagca | ttcctactct | ccattgtacg | cacacgctcg | 1140 |
| gaagcctggc | tgtgggtttg | ggcatgagag | gcagggacaa | caaaccagt | atatatgatt | 1200 |
| ataactttt | cctgtttccc | tatttccaaa | tggtcgaaag | gaggaagtta | ggtctaccta | 1260 |
| agctgaatgt | attcagttag | caggagaaat | gaaatcctat | acgtttaata | ctagaggaga | 1320 |
| accgccttag | aatatttatt | tcattggcaa | tgactccagg | actacacagc | gaaattgtat | 1380 |
| tgcatgtgct | gccaaaatac | tttagctctt | tccttcgaag | tacgtcggat | cctgtaattg | 1440 |
| agacaccgag | tttaggtgac | tagggttttc | ttttgaggag | gagtccccca | ccccgccccg | 1500 |
| ctctgccgcg | acaggaagct | agcgatccgg | aggacttaga | atacaatcgt | agtgtgggta | 1560 |
| aacatggagg | gcaagcgcct | gcaaagggaa | gtaagaagat | tcccagtcct | tgttgaaatc | 1620 |
| catttgcaaa | cagaggaagc | tgccgcgggt | cgcagtcggt | gggggaagc | cctgaacccc | 1680 |
| acgctgcacg | gctgggctgg | ccaggtgcgg | ccacgccccc | atcgcggcgg | ctggtaggag | 1740 |
| tgaatcagac | cgtcagtatt | ggtaaagaag | tctgcggcag | ggcagggagg | gggaagagta | 1800 |
| gtcagtcgct | cgctcactcg | ctcgctcgca | cagacactgc | tgcagtgaca | ctcggccctc | 1860 |
| cagtgtcgcg | gagacgcaag | agcagcgcgc | agcacctgtc | cgcccggagc | gagcccggcc | 1920 |
| cgcggccgta | gaaaaggagg | gaccgccgag | gtgcgcgtca | gtactgctca | gcccggcagg | 1980 |
| gacgcgggag | gatgtggact | gggtggac | | | | 2008 |

<210> SEQ ID NO 29
<211> LENGTH: 252

<212> TYPE: DNA
<213> ORGANISM: Artificial Sequence
<220> FEATURE:
<223> OTHER INFORMATION: Southern blot probe

<400> SEQUENCE: 29

```
ccggggcggg gctgcggttg cggtgcctgc gcccgcggcg gcggaggcgc aggcggtggc    60
gagtgggtga gtgaggaggc ggcatcctgg cgggtggctg tttggggttc ggctgccggg   120
aagaggcgcg ggtagaagcg ggggctctcc tcagagctcg acgcattttt actttccctc   180
tcatttctct gaccgaagct gggtgtcggg ctttcgcctc tagcgactgg tggaattgcc   240
tgcatccggg cc                                                       252
```

<210> SEQ ID NO 30
<211> LENGTH: 39
<212> TYPE: DNA
<213> ORGANISM: Artificial Sequence
<220> FEATURE:
<223> OTHER INFORMATION: Asuragen 2-Primer Fwd

<400> SEQUENCE: 30

```
tgcgcctccg ccgccgcggg cgcaggcacc gcaaccgca                           39
```

<210> SEQ ID NO 31
<211> LENGTH: 35
<212> TYPE: DNA
<213> ORGANISM: Artificial Sequence
<220> FEATURE:
<223> OTHER INFORMATION: Asuragen 2-Primer Rev

<400> SEQUENCE: 31

```
cgcagcctgt agcaagctct ggaactcagg agtcg                               35
```

<210> SEQ ID NO 32
<211> LENGTH: 36
<212> TYPE: DNA
<213> ORGANISM: Artificial Sequence
<220> FEATURE:
<223> OTHER INFORMATION: Asuragen 3-Primer Fwd

<400> SEQUENCE: 32

```
atgcaggcaa ttccaccagt cgctagaggc gaaagc                              36
```

<210> SEQ ID NO 33
<211> LENGTH: 40
<212> TYPE: DNA
<213> ORGANISM: Artificial Sequence
<220> FEATURE:
<223> OTHER INFORMATION: Asuragen 3-Primer Rev

<400> SEQUENCE: 33

```
taaccagaag aaaacaagga gggaaacaac cgcagcctgt                          40
```

<210> SEQ ID NO 34
<211> LENGTH: 158
<212> TYPE: DNA
<213> ORGANISM: Homo sapiens

<400> SEQUENCE: 34

```
acgtaaccta cggtgtcccg ctaggaaaga gaggtgcgtc aaacagcgac aagttccgcc    60
cacgtaaaag atgacgcttg gtgtgtcagc cgtccctgct gcccggttgc ttctcttttg   120
ggggcggggt ctagcaagag caggtgtggg tttaggag                            158
```

<210> SEQ ID NO 35
<211> LENGTH: 487
<212> TYPE: DNA
<213> ORGANISM: Homo sapiens

<400> SEQUENCE: 35

| | | | | | |
|---|---|---|---|---|---|
| tatctccgga | gcatttggat | aatgtgacag | ttggaatgca | gtgatgtcga | ctctttgccc | 60 |
| accgccatct | ccagctgttg | ccaagacaga | gattgcttta | agtggcaaat | cacctttatt | 120 |
| agcagctact | tttgcttact | gggacaatat | tcttggtcct | agagtaaggc | acatttgggc | 180 |
| tccaaagaca | gaacaggtac | ttctcagtga | tggagaaata | acttttcttg | ccaaccacac | 240 |
| tctaaatgga | gaaatccttc | gaaatgcaga | gagtggtgct | atagatgtaa | agttttttgt | 300 |
| cttgtctgaa | aagggagtga | ttattgtttc | attaatcttt | gatggaaact | ggaatgggga | 360 |
| tcgcagcaca | tatggactat | caattatact | tccacagaca | gaacttagtt | tctacctccc | 420 |
| acttcataga | gtgtgtgttg | atagattaac | acatataatc | cggaaaggaa | gaatatggat | 480 |
| gcataag | | | | | 487 |

<210> SEQ ID NO 36
<211> LENGTH: 198
<212> TYPE: DNA
<213> ORGANISM: Homo sapiens

<400> SEQUENCE: 36

| | | | | | |
|---|---|---|---|---|---|
| gggtctagca | agagcaggtg | tgggtttagg | aggtgtgtgt | ttttgttttt | cccaccctct | 60 |
| ctccccacta | cttgctctca | cagtactcgc | tgagggtgaa | caagaaaaga | cctgataaag | 120 |
| attaaccaga | agaaaacaag | gagggaaaca | accgcagcct | gtagcaagct | ctggaactca | 180 |
| ggagtcgcgc | gctatgcg | | | | 198 |

<210> SEQ ID NO 37
<211> LENGTH: 118
<212> TYPE: DNA
<213> ORGANISM: Homo sapiens

<400> SEQUENCE: 37

| | | | | | |
|---|---|---|---|---|---|
| gcgatcgcgg | ggcgtggtcg | gggcgggccc | ggggcgggc | ccggggcggg | gctgcggttg | 60 |
| cggtgcctgc | gcccgcggcg | gcggaggcgc | aggcggtggc | gagtgggtga | gtgaggag | 118 |

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
agtactgtga gagcaagtag                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gctctcacag tactcgctga                                                20

```
<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ccgcagcctg tagcaagctc                                                   20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cggccgctag cgcgatcgcg                                                   20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
acgccccgcg atcgcgctag                                                   20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
tggcgagtgg gtgagtgagg                                                   20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ggaagaggcg cgggtagaag                                                   20

<210> SEQ ID NO 45
<211> LENGTH: 1302
<212> TYPE: DNA
<213> ORGANISM: Artificial Sequence
<220> FEATURE:
<223> OTHER INFORMATION: Synthetic

<400> SEQUENCE: 45
gaacttacgg agtcccacga gggaaccgcg gcgcgtcaag cagagacgag ttccgcccac       60
gtgaaagatg gcgtttgtag tgacagccat cccaattgcc ctttccttct aggtggaaag     120
tggggtctag caagagcagg tgtgggttta ggaggtgtgt gttttgtttt tcccacccct     180
ctctccccac tacttgctct cacagtactc gctgagggtg aacaagaaaa gacctgataa     240
agattaacca gaagaaaaca aggagggaaa caaccgcagc ctgtagcaag ctctggaact     300
```

-continued

| | |
|---|---|
| caggagtcgc gcgctatgcg atcgccgtct cggggccggg gccggggccg gggccggggc | 360 |
| cggggccggg gccggggccg gggccggggc cggggccggg gccggggccg gggccggggc | 420 |
| cggggccggg gccggggccg gggccggggc cggggccggg gccggggccg gggccggggc | 480 |
| cggggccggg gccggggccg gggccggggc cggggccggg gccggggccg gggccggggc | 540 |
| cggggccggg gccggggccg gggccggggc cggggccggg gccggggccg gggccggggc | 600 |
| cggggccggg gccggggccg gggccggggc cggggccggg gccggggccg gggccggggc | 660 |
| cggggccggg gccggggccg gggccggggc cggggccggg gccggggccg gggccggggc | 720 |
| cggggccggg gccggggccg gggccggggc cggggccggg gccggggccg gggccggggc | 780 |
| cggggccggg gccggggccg gggccggggc cggggccggg gccggggccg gggccggggc | 840 |
| cggggccggg gccggggccg gggccggggc cggggccggg gccgagaccc tcgagggccg | 900 |
| gccgctagcg cgatcgcggg gcgtggtcgg ggcgggcccg gggcgggcc cggggcgggg | 960 |
| ctgcggttgc ggtgcctgcg cccgcggcgg cggaggcgca ggcggtgcga gtgggtgagt | 1020 |
| gaggaggcgg catcctggcg ggtggctgtt tggggttcgg ctgccgggaa gaggcgcggg | 1080 |
| tagaagcggg ggctctcctc agagctcgac gcatttttac tttccctctc atttctctga | 1140 |
| ccgaagctgg gtgtcgggct ttcgcctcta gcgactggtg gaattgcctg catccgggcc | 1200 |
| ccgggcttcc cggcggcggc ggcggcggcg gcggcgcagg gacaagggat ggggatctgg | 1260 |
| cctcttcctt gctttcccgc cctcagtacc cgagctgtct cc | 1302 |

```
<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
gagtactgtg agagcaagta g                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
gccgcagcct gtagcaagct c                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gcggccgcta gcgcgatcgc g                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
```
gacgccccgc gatcgcgcta g                                          21

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
gtggcgagtg ggtgagtgag g                                          21

<210> SEQ ID NO 51
<211> LENGTH: 26
<212> TYPE: DNA
<213> ORGANISM: Artificial Sequence
<220> FEATURE:
<223> OTHER INFORMATION: Synthetic

<400> SEQUENCE: 51
acaccgctct cacagtactc gctgag                                     26

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
acaccgccgc agcctgtagc aagctcg                                    27

<210> SEQ ID NO 53
<211> LENGTH: 27
<212> TYPE: DNA
<213> ORGANISM: Artificial Sequence
<220> FEATURE:
<223> OTHER INFORMATION: Synthetic

<400> SEQUENCE: 53
acaccgagta ctgtgagagc aagtagg                                    27

<210> SEQ ID NO 54
<211> LENGTH: 27
<212> TYPE: DNA
<213> ORGANISM: Artificial Sequence
<220> FEATURE:
<223> OTHER INFORMATION: Synthetic

<400> SEQUENCE: 54
acaccgacgc cccgcgatcg cgctagg                                    27

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
acaccgcggc cgctagcgcg atcgcgg                                    27

<210> SEQ ID NO 56
<211> LENGTH: 27
<212> TYPE: DNA

```
<213> ORGANISM: Artificial Sequence
<220> FEATURE:
<223> OTHER INFORMATION: Synthetic

<400> SEQUENCE: 56
acaccgtggc gagtgggtga gtgaggg                                        27

<210> SEQ ID NO 57
<211> LENGTH: 26
<212> TYPE: DNA
<213> ORGANISM: Artificial Sequence
<220> FEATURE:
<223> OTHER INFORMATION: Synthetic

<400> SEQUENCE: 57
acaccggaag aggcgcgggt agaagg                                         26

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gacgcgttaa tgccaacttt                                                20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gagggcctat ttcccatgat                                                20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
gacgcgttaa tgccaacttt                                                20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gaacttacgg agtcccacga                                                20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ggagacagct cgggtactga                                                20
```

<210> SEQ ID NO 63
<211> LENGTH: 82
<212> TYPE: DNA
<213> ORGANISM: Artificial Sequence
<220> FEATURE:
<223> OTHER INFORMATION: Synthetic

<400> SEQUENCE: 63
gttggaacca ttcaaaacag catagcaagt taaaataagg ctagtccgtt atcaacttga    60
aaaagtggca ccgagtcggt gc    82

<210> SEQ ID NO 64
<211> LENGTH: 76
<212> TYPE: DNA
<213> ORGANISM: Artificial Sequence
<220> FEATURE:
<223> OTHER INFORMATION: Synthetic

<400> SEQUENCE: 64
gttttagagc tagaaatagc aagttaaaat aaggctagtc cgttatcaac ttgaaaagt    60 ggcaccgagt cggtgc    76

<210> SEQ ID NO 65
<211> LENGTH: 86
<212> TYPE: DNA
<213> ORGANISM: Artificial Sequence
<220> FEATURE:
<223> OTHER INFORMATION: Synthetic

<400> SEQUENCE: 65
gtttaagagc tatgctggaa acagcatagc aagtttaaat aaggctagtc cgttatcaac    60
ttgaaaaagt ggcaccgagt cggtgc    86

<210> SEQ ID NO 66
<211> LENGTH: 19
<212> TYPE: DNA
<213> ORGANISM: Artificial Sequence
<220> FEATURE:
<223> OTHER INFORMATION: Forward Primer

<400> SEQUENCE: 66
catcccaatt gccctttcc    19

<210> SEQ ID NO 67
<211> LENGTH: 21
<212> TYPE: DNA
<213> ORGANISM: Artificial Sequence
<220> FEATURE:
<223> OTHER INFORMATION: Reverse Primer

<400> SEQUENCE: 67
cccacacctg ctcttgctag a    21

<210> SEQ ID NO 68
<211> LENGTH: 17
<212> TYPE: DNA
<213> ORGANISM: Artificial Sequence
<220> FEATURE:
<223> OTHER INFORMATION: Probe

<400> SEQUENCE: 68
tctaggtgga aagtggg    17

```
<210> SEQ ID NO 69
<211> LENGTH: 20
<212> TYPE: DNA
<213> ORGANISM: Artificial Sequence
<220> FEATURE:
<223> OTHER INFORMATION: Forward Primer

<400> SEQUENCE: 69
gagcaggtgt gggtttagga                                              20

<210> SEQ ID NO 70
<211> LENGTH: 20
<212> TYPE: DNA
<213> ORGANISM: Artificial Sequence
<220> FEATURE:
<223> OTHER INFORMATION: Reverse Primer

<400> SEQUENCE: 70
ccaggtctca ctgcattcca                                              20

<210> SEQ ID NO 71
<211> LENGTH: 26
<212> TYPE: DNA
<213> ORGANISM: Artificial Sequence
<220> FEATURE:
<223> OTHER INFORMATION: Probe

<400> SEQUENCE: 71
attgcaagcg ttcggataat gtgaga                                       26

<210> SEQ ID NO 72
<211> LENGTH: 21
<212> TYPE: DNA
<213> ORGANISM: Artificial Sequence
<220> FEATURE:
<223> OTHER INFORMATION: Forward Primer

<400> SEQUENCE: 72
gctgtcacga aggctttctt c                                            21

<210> SEQ ID NO 73
<211> LENGTH: 20
<212> TYPE: DNA
<213> ORGANISM: Artificial Sequence
<220> FEATURE:
<223> OTHER INFORMATION: Reverse Primer

<400> SEQUENCE: 73
gcactgctgc caactacaac                                              20

<210> SEQ ID NO 74
<211> LENGTH: 24
<212> TYPE: DNA
<213> ORGANISM: Artificial Sequence
<220> FEATURE:
<223> OTHER INFORMATION: Probe

<400> SEQUENCE: 74
tcaatgccat cagctcacac ctgc                                         24

<210> SEQ ID NO 75
<211> LENGTH: 17
<212> TYPE: DNA
<213> ORGANISM: Artificial Sequence
<220> FEATURE:
<223> OTHER INFORMATION: Forward Primer
```

<400> SEQUENCE: 75
aagaggcgcg ggtagaa                                                        17

<210> SEQ ID NO 76
<211> LENGTH: 22
<212> TYPE: DNA
<213> ORGANISM: Artificial Sequence
<220> FEATURE:
<223> OTHER INFORMATION: Reverse Primer

<400> SEQUENCE: 76
cagcttcggt cagagaaatg ag                                                  22

<210> SEQ ID NO 77
<211> LENGTH: 24
<212> TYPE: DNA
<213> ORGANISM: Artificial Sequence
<220> FEATURE:
<223> OTHER INFORMATION: Probe

<400> SEQUENCE: 77
ctctcctcag agctcgacgc attt                                                24

<210> SEQ ID NO 78
<211> LENGTH: 20
<212> TYPE: DNA
<213> ORGANISM: Artificial Sequence
<220> FEATURE:
<223> OTHER INFORMATION: Forward Primer

<400> SEQUENCE: 78
ctgcacaatt tcagcccaag                                                     20

<210> SEQ ID NO 79
<211> LENGTH: 20
<212> TYPE: DNA
<213> ORGANISM: Artificial Sequence
<220> FEATURE:
<223> OTHER INFORMATION: Reverse Primer

<400> SEQUENCE: 79
caggtcatgt cccacagaat                                                     20

<210> SEQ ID NO 80
<211> LENGTH: 24
<212> TYPE: DNA
<213> ORGANISM: Artificial Sequence
<220> FEATURE:
<223> OTHER INFORMATION: Probe

<400> SEQUENCE: 80
catatgaggg cagcaatgca agtc                                                24

<210> SEQ ID NO 81
<211> LENGTH: 16
<212> TYPE: DNA
<213> ORGANISM: Artificial Sequence
<220> FEATURE:
<223> OTHER INFORMATION: LNA Probe for sense G4C2 RNA
<220> FEATURE:
<221> NAME/KEY: TYE563
<222> LOCATION: (1)..(1)

<400> SEQUENCE: 81
ccccggcccc ggcccc                                                         16

```
<210> SEQ ID NO 82
<211> LENGTH: 22
<212> TYPE: DNA
<213> ORGANISM: Artificial Sequence
<220> FEATURE:
<223> OTHER INFORMATION: LNA Probe for antisense G4C2 RNA
<220> FEATURE:
<221> NAME/KEY: TYE563
<222> LOCATION: (1)..(1)

<400> SEQUENCE: 82
ggggccgggg ccggggggcc cc                                              22

<210> SEQ ID NO 83
<211> LENGTH: 18
<212> TYPE: DNA
<213> ORGANISM: Artificial Sequence
<220> FEATURE:
<223> OTHER INFORMATION: DNA Probe for sense G4C2 RNA
<220> FEATURE:
<221> NAME/KEY: Cy3
<222> LOCATION: (18)..(18)

<400> SEQUENCE: 83
ccccggcccc ggccccgg                                                   18

<210> SEQ ID NO 84
<211> LENGTH: 17
<212> TYPE: DNA
<213> ORGANISM: Artificial Sequence
<220> FEATURE:
<223> OTHER INFORMATION: DNA Probe for antisense G4C2 RNA
<220> FEATURE:
<221> NAME/KEY: Cy3
<222> LOCATION: (17)..(17)

<400> SEQUENCE: 84
ggggccgggg ccggggc                                                    17
```

NON-HUMAN ANIMALS HAVING A HEXANUCLEOTIDE REPEAT EXPANSION IN A C9ORF72 LOCUS

CROSS-REFERENCE TO RELATED APPLICATIONS

This application claims the benefit of U.S. Provisional Application No. 62/402,613, filed Sep. 30, 2016, and U.S. Provisional Application No. 62/452,795, filed Jan. 31, 2017, each of which is hereby incorporated herein in its entirety by reference.

INCORPORATION BY REFERENCE OF SEQUENCE LISTING

An official copy of the sequence listing is submitted concurrently with the specification electronically via EFS-Web as an ASCII formatted sequence listing with a file name of "2017-09-29-10267US01-SEQ-LIST_ST25", a creation date of Sep. 29, 2017, and a size of about 94 KB. The sequence listing contained in this ASCII formatted document is part of the specification and is herein incorporated by reference in its entirety.

BACKGROUND

Neurodegenerative diseases are major contributors to disability and disease. In particular, amyotrophic lateral sclerosis (ALS, also referred to as Lou Gehrig's disease) and frontotemporal dementia (FTD) are rare nervous system disorders characterized by progressive neuronal loss and/or death.

Although aging is viewed as the greatest risk factor for neurodegenerative disease, several genetic components have been discovered. For example, mutations in the copper-zinc superoxide dismutase (SOD1) gene have long been associated with ALS. Also, expanded hexanucleotide repeats of GGGGCC within a non-coding region of the C9ORF72 gene have been linked to both ALS and FTD. Currently, there is no cure for either disease, although some treatments are able to prolong life by about 3-5 months.

While various laboratory animal models are extensively used in the development of most therapeutics, very few if any models exist that address neurodegenerative and inflammatory diseases in ways that provide for elucidation of the exact molecular mechanism by which identified genetic components cause disease, which elucidation in turn may uncover potential therapeutic modalities for not only ALS or other neurodegenerative diseases having a similar clinical presentation. Thus, the manner in which genetic mutations cause neurodegenerative disease remains largely unknown. Ideal animal models would contain the same genetic components and represent similar characteristics of human disease. Given the genetic differences between species, there is a high unmet need for the development of improved animal models that closely recapitulate human neurodegenerative and/or inflammatory disease. Of course, such improved animal models provide significant value in the development of effective therapeutic and/or prophylactic agents.

SUMMARY

The present invention encompasses the recognition that it is desirable to engineer non-human animals or non-human animal cells (e.g., embryonic stem cell, embryonic stem cell derived-motor neuron, brain cell, neuronal cell, muscle cell, heart cell) to permit improved in vivo or in vitro systems for identifying and developing new therapeutics and, in some embodiments, therapeutic regimens, which can be used for the treatment of neurodegenerative diseases, disorders and conditions. In some embodiments, the in vivo or in vitro systems as described herein can be used for identifying and developing new therapeutics for treating diseases, disorders, and/or conditions associated with the C9ORF72 locus, particularly a heterologous hexanucleotide repeat expansion sequence in the locus, such as, e.g., neurodegenerative disorders. Further, non-human animals or non-human animal cells (e.g., embryonic stem cell, embryonic stem cell derived-motor neuron, brain cell, neuronal cell, muscle cell, heart cell) described herein that comprise an insertion of a hexanucleotide repeat expansion sequence in a C9ORF72 locus are desirable, for example, for use in identifying and developing therapeutics that target a GGGGCC hexanucleotide repeat (SEQ ID NO:1), products derived therefrom, e.g., sense or antisense RNA transcribed therefrom, a RAN translation product and/or dipeptide repeat protein encoded by the hexanucleotide repeat, etc. In some embodiments, non-human animals and non-human animal cells (e.g., embryonic stem cell, embryonic stem cell derived-motor neuron, brain cell, neuronal cell, muscle cell, heart cell) as described herein respectively provide improved in vivo and in vitro systems (or models) for neurodegenerative diseases, disorders and conditions (e.g., ALS and/or FTD).

A non-human animal or non-human animal cell (e.g., embryonic stem cell, embryonic stem cell derived-motor neuron, brain cell, neuronal cell, muscle cell, heart cell) described herein comprises in its genome a heterologous hexanucleotide repeat expansion sequence inserted into an endogenous C9orf72 locus, wherein the heterologous hexanucleotide repeat expansion sequence comprises at least one repeat of the hexanucleotide sequence set forth as SEQ ID NO: 1. In some embodiments, a non-human animal or non-human animal cell (e.g., embryonic stem cell, embryonic stem cell derived-motor neuron, brain cell, neuronal cell, muscle cell, heart cell) described herein comprises in its germline genome a heterologous hexanucleotide repeat expansion sequence inserted into an endogenous C9orf72 locus, wherein the heterologous hexanucleotide repeat expansion sequence comprises at least one repeat of the hexanucleotide sequence set forth as SEQ ID NO: 1. In some embodiments, the heterologous hexanucleotide expansion sequence is a non-rodent (e.g., non-rat or non-mouse, e.g., a human) hexanucleotide expansion sequence that comprises at least one instance, e.g., repeat, of the hexanucleotide sequence set forth as SEQ ID NO:1. In some embodiments, the (human) heterologous hexanucleotide repeat expansion sequence comprises more than one, preferably contiguous, repeats of the hexanucleotide sequence set forth as SEQ ID NO: 1. In some embodiments, the (human) heterologous hexanucleotide repeat expansion sequence comprises at least about three, preferably contiguous, repeats of the hexanucleotide sequence set forth as SEQ ID NO: 1. In some embodiments, the heterologous (human) hexanucleotide repeat expansion sequence comprises at least about five, preferably contiguous, repeats of the hexanucleotide sequence set forth as SEQ ID NO: 1. In some embodiments, the heterologous (human) hexanucleotide repeat expansion sequence comprises at least about ten, preferably contiguous, repeats of the hexanucleotide sequence set forth as SEQ ID NO: 1. In some embodiments, the heterologous (human) hexanucleotide repeat expansion sequence comprises at least about fifteen, preferably contiguous, repeats of the hexanucleotide sequence set forth as SEQ ID NO: 1. In some embodiments, the heterologous (human) hexanucleotide repeat expansion sequence comprises at least about twenty, preferably contiguous, repeats of the hexanucleotide sequence set forth as SEQ ID NO: 1. In some embodiments, the heterologous (human) hexanucleotide repeat expansion sequence comprises at least about thirty, preferably contiguous, repeats of the hexanucleotide sequence set forth as SEQ ID NO: 1. In some embodiments, the heterologous (human) hexanucleotide repeat expansion sequence comprises at least about forty, preferably contiguous, repeats of the hexanucleotide sequence set forth as SEQ ID NO: 1. In some embodiments, the heterologous (human) hexanucleotide repeat expansion sequence comprises at least about fifty, preferably contiguous, repeats of the hexanucleotide sequence set forth as SEQ ID NO: 1. In some embodiments, the heterologous (human) hexanucleotide repeat expansion sequence comprises at least about sixty, preferably contiguous, repeats of the hexanucleotide sequence set forth as SEQ ID NO: 1. In some embodiments, the heterologous (human) hexanucleotide repeat expansion sequence comprises at least about seventy, preferably contiguous, repeats of the hexanucleotide sequence set forth as SEQ ID NO: 1. In some embodiments, the heterologous (human) hexanucleotide repeat expansion sequence comprises at least about eighty, preferably contiguous, repeats of the hexanucleotide sequence set forth as SEQ ID NO: 1. In some embodiments, the heterologous (human) hexanucleotide repeat expansion sequence comprises at least about ninety, preferably contiguous, repeats of the hexanucleotide sequence set forth as SEQ ID NO: 1. In some embodiments, the heterologous (human) hexanucleotide repeat expansion sequence comprises at least about one-hundred, preferably contiguous, repeats of the hexanucleotide sequence set forth as SEQ ID NO: 1. In some embodiments, the non-human animal comprises the heterologous (human) hexanucleotide repeat expansion sequence in its germline genome.

In some embodiments, the heterologous (e.g., non-rodent, non-rat, non-mouse and/or human) hexanucleotide repeat expansion sequence comprises heterologous (e.g., non-rodent, non-rat, non-mouse and/or human) sequences that flank the at least one, e.g., at least about three, at least about five, at least about ten, at least about fifteen, at least about twenty, at least about thirty, at least about forty, at least about fifty, at least about sixty, at least about seventy, at least about eighty, at least about ninety or at least about one-hundred, preferably contiguous, repeats of the hexanucleotide sequence set forth as SEQ ID NO:1. Accordingly, a heterologous (e.g., non-rodent, non-rat, non-mouse, and/or human) hexanucleotide repeat expansion sequence may comprise from 5' to 3': a first heterologous hexanucleotide flanking sequence, one or more (preferably contiguous) instances of the hexanucleotide set forth as SEQ ID NO:1, and a second heterologous hexanucleotide flanking sequence. In some embodiments, a heterologous hexanucleotide repeat expansion sequence is identical to or substantially identical to a naturally occurring genomic sequence comprising a first heterologous hexanucleotide flanking sequence, one or more instances of the hexanucleotide sequence set forth as SEQ ID NO:1, and a second heterologous hexanucleotide flanking sequence. Naturally occurring first and/or second heterologous hexanucleotide flanking sequences may each independently be, e.g., at least 4 base pairs in length, e.g., at least 10 base pairs in length, e.g., at least 20 base pairs in length etc.

In some embodiments, a heterologous human hexanucleotide expansion sequence spans (and optionally encompasses) all or portions of exons 1a and/or exon 1b of a human C9orf72 gene. In some embodiments, a first heterologous hexanucleotide flanking sequence comprises all or part of the sequence of exon 1a of a human C9orf72 gene (set forth as SEQ ID NO:34) and/or a second heterologous hexanucleotide flanking sequence comprises all or part of the sequence of exon 1b of a human C9orf72 gene (set forth as SEQ ID NO:35). In some embodiments, a first heterologous hexanucleotide flanking sequence comprises the sequence set forth as SEQ ID NO:36, or a portion thereof, and/or a second heterologous hexanucleotide flanking sequence comprises the sequence set forth as SEQ ID NO:37, or a portion thereof.

An exemplary human hexanucleotide repeat expansion sequence is set forth as SEQ ID NO:2 (comprising from 5' to 3': a first heterologous hexanucleotide flanking sequence comprising a sequence set forth as SEQ ID NO: 36, 3 repeats of the hexanucleotide sequence set forth as SEQ ID NO:1, and a second heterologous hexanucleotide flanking sequence comprising a sequence set forth as SEQ ID NO:37). Another exemplary human hexanucleotide repeat expansion sequence is set forth as SEQ ID NO:3 (comprising from 5' to 3': a first heterologous hexanucleotide flanking sequence comprising a sequence set forth as SEQ ID NO: 36, 100 repeats of the hexanucleotide sequence set forth as SEQ ID NO:1, and a second heterologous hexanucleotide flanking sequence comprising a sequence set forth as SEQ ID NO:37). Accordingly, disclosed herein are non-human animals, e.g., rodents such as a rat or a mouse, whose genomes comprise in an endogenous C9orf72 locus a sequence set forth as SEQ ID NO:2, a variant of SEQ ID NO:2, a sequence set forth as SEQ ID NO:3, or a variant of SEQ ID NO:3.

In some embodiments, a non-human animal or non-human animal cell (e.g., embryonic stem cell, embryonic stem cell derived-motor neuron, brain cell, neuronal cell, muscle cell, heart cell) comprises in its genome a hexanucleotide repeat expansion sequence comprising a sequence that is a SEQ ID NO:2 variant, which comprises from 5' to 3': a first human hexanucleotide flanking sequence comprising a sequence set forth as SEQ ID NO: 36 (or a portion thereof, e.g., a sequence set forth as SEQ ID NO:34), one or two contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or a non-human animal cell (e.g., embryonic stem cell, embryonic stem cell derived-motor neuron, brain cell, neuronal cell, muscle cell, heart cell) as described herein comprises in its genome a hexanucleotide repeat expansion sequence comprising a sequence that is a SEQ ID NO:3 variant, which comprises from 5' to 3': a first human hexanucleotide flanking sequence comprising a sequence set forth as SEQ ID NO: 36 (or a portion thereof, e.g., a sequence set forth as SEQ ID NO:34), more than one and less than 100 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or non-human animal cell (e.g., embryonic stem cell, embryonic stem cell derived-motor neuron, brain cell, neuronal cell, muscle cell, heart cell) comprises in its (germline) genome a hexanucleotide repeat expansion sequence comprising a sequence that is a SEQ ID NO:3 variant, comprises from 5' to 3': a first human hexanucleotide flanking sequence comprising a sequence set forth as SEQ ID NO: 36 (or a portion thereof, e.g., a sequence set forth as SEQ ID NO:34), 36 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or non-human animal cell (e.g., embryonic stem cell, embryonic stem cell derived-motor neuron, brain cell, neuronal cell, muscle cell, heart cell) as described herein comprises in its genome a hexanucleotide repeat expansion sequence comprising a sequence that is a SEQ ID NO:3 variant, which comprises from 5' to 3': a first human hexanucleotide flanking sequence comprising a sequence set forth as SEQ ID NO: 36 (or a portion thereof, e.g., a sequence set forth as SEQ ID NO:34), 92 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35).

In some embodiments, a non-human animal or non-human animal cell (e.g., embryonic stem cell, embryonic stem cell derived-motor neuron, brain cell, neuronal cell, muscle cell, heart cell) as disclosed herein is heterozygous or homozygous for a hexanucleotide repeat expansion sequence comprising a sequence that is a SEQ ID NO:2 variant, which comprises from 5' to 3': a first human hexanucleotide flanking sequence comprising a sequence set forth as SEQ ID NO: 36 (or a portion thereof, e.g., a sequence set forth as SEQ ID NO:34), one or two contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or non-human animal cell (e.g., embryonic stem cell, embryonic stem cell derived-motor neuron, brain cell, neuronal cell, muscle cell, heart cell) comprises in its (germline) genome a hexanucleotide repeat expansion sequence comprising a sequence that is a SEQ ID NO:3 variant, which comprises from 5' to 3': a first human hexanucleotide flanking sequence comprising a sequence set forth as SEQ ID NO: 36 (or a portion thereof, e.g., a sequence set forth as SEQ ID NO:34), more than one and less than 100 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or non-human animal cell (e.g., embryonic stem cell, embryonic stem cell derived-motor neuron, brain cell, neuronal cell, muscle cell, heart cell) comprises in its (germline) genome a hexanucleotide repeat expansion sequence comprising a sequence that is a SEQ ID NO:3 variant, comprises from 5' to 3': a first human hexanucleotide flanking sequence comprising a sequence set forth as SEQ ID NO: 36 (or a portion thereof, e.g., a sequence set forth as SEQ ID NO:34), 36 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35). In some embodiments, a non-human animal or non-human animal cell (e.g., embryonic stem cell, embryonic stem cell derived-motor neuron, brain cell, neuronal cell, muscle cell, heart cell) comprises in its (germline) genome a hexanucleotide repeat expansion sequence comprising a sequence that is a SEQ ID NO:3 variant, which comprises from 5' to 3': a first human hexanucleotide flanking sequence comprising a sequence set forth as SEQ ID NO: 36 (or a portion thereof, e.g., a sequence set forth as SEQ ID NO:34), 92 contiguous repeats of the hexanucleotide sequence set forth as SEQ ID NO:1, and a second human hexanucleotide flanking sequence comprising a sequence set forth as SEQ ID NO:37 (or a portion thereof, e.g., a sequence set forth as SEQ ID NO:35).

In some embodiments, a non-human animal or non-human animal cell (e.g., embryonic stem cell, embryonic stem cell derived-motor neuron, brain cell, neuronal cell, muscle cell, heart cell) comprises in its (germline) genome a replacement of 5' untranslated and/or non-coding endogenous non-human sequences of the endogenous C9orf72 locus with the heterologous (human) hexanucleotide repeat expansion sequence. In some embodiments, the untranslated and/or non-coding sequence spanning between (and optionally encompassing at least a portion of) endogenous exon 1 (e.g., exon 1a and/or 1b) and the ATG start codon of the endogenous non-human C9orf72 locus, or a portion thereof, is replaced with the heterologous hexanucleotide repeat expansion sequence. Additional sequences (e.g., recombinase recognition sequences, a drug resistance cassette, a reporter gene, etc.) linked to the heterologous (human) hexanucleotide expansion sequence, may also replace the untranslated and/or non-coding sequence spanning between (and optionally encompassing) endogenous exon 1 (e.g., exon 1a and/or exon 1b) and the ATG start codon of the endogenous non-human C9orf72 locus, or a portion thereof.

Accordingly, in some embodiments, a non-human animal or non-human animal cell (e.g., embryonic stem cell, embryonic stem cell derived-motor neuron, brain cell, neuronal cell, muscle cell, heart cell) as disclosed herein may comprise a heterozygous or homozygous replacement of an endogenous sequence that (1) starts from the 5' end, within, or the 3' end of an endogenous exon 1 and (2) ends 5' of the endogenous ATG start codon, or a portion thereof, with a heterologous hexanucleotide repeat expansion sequence, e.g., a hexanucleotide repeat expansion sequence comprising a least one repeat of the hexanucleotide sequence set forth as SEQ ID NO:1. In some embodiments, a non-human animal or non-human animal cell (e.g., embryonic stem cell, embryonic stem cell derived-motor neuron, brain cell, neuronal cell, muscle cell, heart cell) as disclosed herein may comprise a heterozygous or homozygous replacement of an endogenous sequence that (i) starts from the 5' end of, within, or from the 3' end of an endogenous exon 1 and (ii) ends 5' of the endogenous ATG start codon, or a portion thereof, with a heterologous hexanucleotide repeat expansion comprising from 5' to 3': a first human hexanucleotide flanking sequence comprising a sequence set forth as SEQ ID NO: 34, at least one instance of the hexanucleotide sequence set forth as SEQ ID NO:1, and a second human hexanucleotide flanking sequence comprising a sequence set forth as SEQ ID NO:35. In some embodiments, a non-human animal or non-human animal cell (e.g., embryonic stem cell, embryonic stem cell derived-motor neuron, brain cell, neuronal cell, muscle cell, heart cell) as disclosed herein may comprise a heterozygous or homozygous replacement of an endogenous sequence that (ii) starts from the 5' end of, within, or the 3' end of an endogenous exon 1 and (ii) ends 5' of the endogenous ATG start codon, or a portion thereof, with a heterologous hexanucleotide repeat expansion sequence comprising from 5' to 3': a first human hexanucleotide flanking sequence comprising a sequence set forth as SEQ ID NO: 36, at least one instance of the hexanucleotide sequence set forth as SEQ ID NO:1, and a second human hexanucleotide flanking sequence comprising a sequence set forth as SEQ ID NO:37. In some embodiments, a non-human animal or non-human animal cell (e.g., embryonic stem cell, embryonic stem cell derived-motor neuron, brain cell, neuronal cell, muscle cell, heart cell) as disclosed herein may comprise a heterozygous or homozygous replacement of an endogenous sequence that (ii) starts from the 5' end of, within, or the 3' end of an endogenous exon 1 and (ii) ends 5' of the endogenous ATG start codon, or a portion thereof, with a heterologous hexanucleotide repeat expansion sequence comprising the sequence set forth as SEQ ID NO:2, a variant thereof, SEQ ID NO:3 or a variant thereof.

In some embodiments, a non-human animal or non-human animal cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises one or more repeats of the hexanucleotide sequence set forth as SEQ ID NO: 1, and wherein the non-human animal or cell exhibits one or more of the following characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci comprising a C9orf72 RNA sense and/or antisense transcript compared to a control animal or cell comprising a wildtype C9orf72 locus, e.g., as evaluated by fluorescence activated in situ hybridization, (iii) an increased level of dipeptide repeat proteins compared to a control animal or cell comprising a wildtype C9orf72 locus, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises three or more repeats of the hexanucleotide sequence set forth as SEQ ID NO: 1, and wherein the non-human animal or cell exhibits one or more of the following characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci an increased number of RNA foci comprising a C9orf72 RNA sense and/or antisense transcript compared to a control animal or cell comprising a wildtype C9orf72 locus, e.g., as evaluated by fluorescence activated in situ hybridization, (iii) an increased level of dipeptide repeat proteins compared to a control animal or cell comprising a wildtype C9orf72 locus, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises at least thirty repeats of the hexanucleotide sequence set forth as SEQ ID NO: 1, and wherein the non-human animal or cell exhibits one or more of the following characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci comprising an increased number of RNA foci comprising a C9orf72 RNA sense and/or antisense transcript compared to a control animal or cell comprising a wildtype C9orf72 locus, e.g., as evaluated by fluorescence activated in situ hybridization, (iii) an increased level of dipeptide repeat proteins compared to a control animal or cell comprising a wildtype C9orf72 locus, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises ninety or more repeats of the hexanucleotide sequence set forth as SEQ ID NO: 1, and wherein the non-human animal or cell exhibits one or more of the following characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci an increased number of RNA foci comprising a C9orf72 RNA sense and/or antisense transcript compared to a control animal or cell comprising a wildtype C9orf72 locus, e.g., as evaluated by fluorescence activated in situ hybridization, (iii) an increased level of dipeptide repeat proteins compared to a control animal or cell comprising a wildtype C9orf72 locus, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises ninety-two repeats of the hexanucleotide sequence set forth as SEQ ID NO: 1, and wherein the non-human animal or cell exhibits all of the following three characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci comprising an increased number of RNA foci comprising a C9orf72 RNA sense and/or antisense transcript compared to a control animal or cell comprising a wildtype C9orf72 locus, e.g., as evaluated by fluorescence activated in situ hybridization, and (iii) an increased level of dipeptide repeat proteins compared to a control animal or cell comprising a wildtype C9orf72 locus, e.g., as evaluated by immunofluorescence. In some embodiments, a non-human animal or cell (e.g., embryonic stem cell, embryonic stem cell derived-motor neuron, brain cell, neuronal cell, muscle cell, heart cell) described herein comprises in its (germline) genome a heterologous hexanucleotide repeat expansion sequence inserted at an endogenous C9orf72 locus, wherein the heterologous hexanucleotide repeat expansion sequence comprises more than ninety repeats of the hexanucleotide sequence set forth as SEQ ID NO: 1, and wherein the non-human animal or cell exhibits all of the following three characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci comprising an increased number of RNA foci comprising a C9orf72 RNA sense and/or antisense transcript compared to a control animal or cell comprising a wildtype C9orf72 locus, e.g., as evaluated by fluorescence activated in situ hybridization, and (iii) an increased level of dipeptide repeat proteins compared to a control animal or cell comprising a wildtype C9orf72 locus, e.g., as evaluated by immunofluorescence. In some embodiments, a non-human animal or cell (e.g., embryonic stem cell, embryonic stem cell derived-motor neuron, brain cell, neuronal cell, muscle cell, heart cell) described herein comprises in its genome a heterologous hexanucleotide repeat expansion sequence inserted at an endogenous C9orf72 locus, wherein the heterologous hexanucleotide repeat expansion sequence comprises at least 92 repeats of the hexanucleotide sequence set forth as SEQ ID NO: 1, and wherein the non-human animal or cell exhibits all of the following three characteristics: (i) increased expression of C9orf72 RNA sense and/or antisense transcripts compared to a control animal or cell comprising a wildtype C9orf72 locus, e.g., as evaluated by quantitative PCR (ii) an increased number of RNA foci comprising an increased number of RNA foci comprising a C9orf72 RNA sense and/or antisense transcript compared to a control animal or cell comprising a wildtype C9orf72 locus, e.g., as evaluated by fluorescence activated in situ hybridization, and (iii) an increased level of dipeptide repeat proteins compared to a control animal or cell comprising a wildtype C9orf72 locus, e.g., as evaluated by immunofluorescence.

In some embodiments, a non-human animal or cell (e.g., embryonic stem cell, embryonic stem cell derived-motor neuron, brain cell, neuronal cell, muscle cell, heart cell) described herein comprises in its genome a heterologous hexanucleotide repeat expansion sequence inserted at an endogenous C9orf72 locus, wherein the heterologous hexanucleotide repeat expansion sequence comprises a repeat of the hexanucleotide sequence set forth as SEQ ID NO: 1, and wherein one or more of the following characteristics of the non-human animal or cell is not significantly different compared to a control non-human animal or cell comprising a wildtype C9orf72 locus: (i) the amount of C9orf72 RNA sense and/or antisense transcripts compared, e.g., as evaluated by quantitative PCR (ii) the number of RNA foci comprising a C9orf72 RNA sense and/or antisense transcript, e.g., as evaluated by fluorescence activated in situ hybridization, (iii) the level of dipeptide repeat proteins, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its genome a heterologous hexanucleotide repeat expansion sequence inserted at an endogenous C9orf72 locus, wherein the heterologous hexanucleotide repeat expansion sequence comprises three repeats of the hexanucleotide sequence set forth as SEQ ID NO: 1, and wherein one or more of the following characteristics of the non-human animal or cell is not significantly different compared to a control non-human animal or cell comprising a wildtype C9orf72 locus: (i) the amount of C9orf72 RNA sense and/or antisense transcripts compared, e.g., as evaluated by quantitative PCR (ii) the number of RNA foci comprising a C9orf72 RNA sense and/or antisense transcript, e.g., as evaluated by fluorescence activated in situ hybridization, (iii) the level of dipeptide repeat proteins, e.g., as evaluated by immunofluorescence or (iv) any combination of (i)-(iii). In some embodiments, a non-human animal or cell (e.g., embryonic stem cell, embryonic stem cell derived-motor neuron, brain cell, neuronal cell, muscle cell, heart cell) described herein comprises in its genome a heterologous hexanucleotide repeat expansion sequence inserted at an endogenous C9orf72 locus, wherein the heterologous hexanucleotide repeat expansion sequence comprises thirty repeats of the hexanucleotide sequence set forth as SEQ ID NO: 1, and wherein one or more of the following characteristics of the non-human animal or cell is not significantly different compared to a control non-human animal or cell comprising a wildtype C9orf72 locus: (i) the amount of C9orf72 RNA sense and/or antisense transcripts compared, e.g., as evaluated by quantitative PCR (ii) the number of RNA foci comprising a C9orf72 RNA sense and/or antisense transcript, e.g., as evaluated by fluorescence activated in situ hybridization, (iii) the level of dipeptide repeat proteins, e.g., as evaluated by immunofluorescence or (iv) any combination of (i)-(iii).

In some embodiments, a nucleic acid construct (or targeting construct, or targeting vector) as described herein is provided.

In some embodiments, a nucleic acid construct as described herein comprises, from 5' to 3', a 5' non-human targeting arm comprising a polynucleotide that is homologous to a 5' portion of a non-human (e.g., a rodent such as a mouse or a rat) C9ORF72 locus, a heterologous hexanucleotide repeat expansion sequence comprising at least one of a hexanucleotide sequence set forth as SEQ ID NO:1, a first recombinase recognition site; a first promoter operably linked to a selectable marker, a second recombinase recognition site, and a 3' non-human targeting arm comprising a polynucleotide that is homologous to a 3' portion of a non-human (e.g., a rodent such as a mouse or a rat) C9ORF72 locus. In some embodiments, the 5' portion of a non-human (e.g., a rodent such as a mouse or rat) C9ORF72 locus includes a genomic sequence upstream of exon 1 of the non-human (e.g., rodent such as mouse or rat) C9ORF72 gene.

In some embodiments, recombinase recognition sites include loxP, lox511, lox2272, lox2372, lox66, lox71, loxM2, lox5171, FRT, FRT11, FRT71, attp, att, FRT, rox, or a combination thereof. In some embodiments, a recombinase gene is included in the construct, e.g., under the control of an inducible promoter. The recombinase gene may be selected from the group consisting of Cre, Flp (e.g., Flpe, Flpo), and Dre. In some certain embodiments, first and second recombinase recognition sites are lox (e.g., loxP) sites, and a recombinase gene encodes a Cre recombinase.

In some embodiments, a first promoter is selected from the group consisting of protamine (Prot; e.g., Prot1 or Prot5), Blimp1, Blimp1 (1 kb fragment), Blimp1 (2 kb fragment), Gata6, Gata4, Igf2, Lhx2, Lhx5, hUB1, Em7 and Pax3. In some certain embodiments, a first promoter is a hUB1 promoter in combination with an Em7 promoter.

In some embodiments, a selectable marker is selected from group consisting of neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and Herpes simplex virus thymidine kinase (HSV-tk). In some certain embodiments, a selectable marker is neo$^r$.

In some embodiments, the nucleic acid construct comprises the sequence set forth as SEQ ID NO:8, which comprises from 5' to 3': a 5' non-human (mouse) targeting arm, a first human hexanucleotide flanking sequence comprising the sequence set forth as SEQ ID NO:36, three repeats of the hexanucleotide sequence set forth as SEQ ID NO:1, a second human hexanucleotide flanking sequence comprising the sequence set forth as SEQ ID NO:37, a floxed drug resistance (neo') cassette and a 3' non-human (mouse) targeting arm. In some embodiments, the nucleic acid construct comprises the sequence set forth as SEQ ID NO:9, which comprises from 5' to 3': a 5' non-human (mouse) targeting arm, a first human hexanucleotide flanking sequence comprising the sequence set forth as SEQ ID NO:36, one-hundred repeats of the hexanucleotide sequence set forth as SEQ ID NO:1, a second human hexanucleotide flanking sequence comprising the sequence set forth as SEQ ID NO:37, a floxed drug resistance (neo') cassette and a 3' non-human (mouse) targeting arm.

In some embodiments, a method of making a non-human animal or non-human animal cel is provided whose genome comprises an insertion of a heterologous hexanucleotide repeat expansion sequence into an endogenous C9orf72 locus, wherein the heterologous hexanucleotide repeat expansion sequence comprises at least one, e.g., at least about 3 repeats, e.g., at least about 30 repeats, e.g., at least about 90 repeats, of a hexanucleotide sequence set forth as SEQ ID NO:1, the method comprising (a) introducing a nucleic acid sequence, e.g., a nucleic acid construct as described herein (e.g., a nucleic acid construct comprising a sequence set forth as SEQ ID NO:8 or a nucleic acid construct comprising a sequence set forth as SEQ ID NO:9), into a non-human embryonic stem cell so that the heterologous hexanucleotide repeat expansion sequence is inserted into an endogenous C9ORF72 locus, which nucleic acid comprises a polynucleotide that is homologous to the C9ORF72 locus; (b) obtaining a genetically modified non-human embryonic stem cell from (a); and optionally, (c) creating a non-human animal using the genetically modified non-human embryonic stem cell of (b). In some embodiments, a method of making a non-human animal described herein further comprises a step of breeding a non-human animal generated in (c) so that a non-human animal homozygous for the insertion is created.

In some embodiments, a method for making a non-human animal whose genome comprises an insertion of a heterologous hexanucleotide repeat expansion sequence, which comprises at least one repeat of the hexanucleotide sequence set forth as SEQ ID NO:1, in an endogenous C9ORF72 locus is provided, the method comprising modifying the genome of a non-human animal so that it comprises an inserted heterologous hexanucleotide repeat expansion sequence in an endogenous C9ORF72 locus, thereby making said non-human animal.

In some embodiments, a non-human animal is provided which is obtainable by, generated from, or produced from a method as described herein. In some embodiments, a non-human animal as disclosed herein is produced using a nucleic acid construct comprising a sequence set forth as SEQ ID NO:8. Such a non-human animal comprises a heterozygous or homozygous replacement of about 853 bp of an endogenous C9orf72 locus starting from within endogenous exon 1 with a heterologous nucleotide sequence comprising from 5' to 3': a first human hexanucleotide flanking sequence comprising a sequence set forth as SEQ ID NO: 36, one to three repeats of the hexanucleotide sequence set forth as SEQ ID NO:1, a human hexanucleotide flanking sequence comprising a sequence set forth as SEQ ID NO:37, and a floxed drug resistance (neo') cassette, or upon excision of the neo gene, a lox recombination recognition sequence. In some embodiments, a non-human animal as disclosed herein is produced using a nucleic acid construct comprising a sequence set forth as SEQ ID NO:9. Such a non-human animal comprises a heterozygous or homozygous replacement of about 853 bp of an endogenous C9orf72 locus starting from within endogenous exon 1 with a heterologous nucleotide sequence comprising from 5' to 3': a first human hexanucleotide flanking sequence comprising a sequence set forth as SEQ ID NO: 36, one to one-hundred (e.g., 36 or 92) repeats of the hexanucleotide sequence set forth as SEQ ID NO:1, a human hexanucleotide flanking sequence comprising a sequence set forth as SEQ ID NO:37, and a floxed drug resistance (neo') cassette, or upon excision of the neo gene, a lox recombination recognition sequence. In some embodiments, a non-human animal comprises a heterologous nucleotide sequence set forth as SEQ ID NO:4 (8026), a heterologous nucleotide sequence set forth as SEQ ID NO:5 (8027), a heterologous nucleotide sequence set forth as SEQ ID NO:6 (8028), or a heterologous nucleotide sequence set forth as SEQ ID NO:7 (8029), wherein the heterologous nucleotide sequence optionally replaces about 853 bp of an untranslated and/or non-coding sequence of an endogenous C9orf72 locus that starts within endogenous exon 1. In some embodiments, a non-human animal as disclosed herein is produced, e.g., by breeding an animal created using a nucleic acid construct comprising a sequence set forth as SEQ ID NO:8 with an animal created using a nucleic acid construct comprising a sequence set forth as SEQ ID NO:9. Such animals may comprise both (1) a heterozygous replacement of about 853 bp of an endogenous C9orf72 locus starting from within endogenous exon 1 with a heterologous nucleotide sequence comprising from 5' to 3': a first human hexanucleotide flanking sequence comprising a sequence set forth as SEQ ID NO: 36, one to three repeats of the hexanucleotide sequence set forth as SEQ ID NO:1, a human hexanucleotide flanking sequence comprising a sequence set forth as SEQ ID NO:37, and a floxed drug resistance (neo') cassette, or upon excision of the neo gene, a lox recombination recognition sequence and (2) a heterozygous replacement of about 853 bp of an endogenous C9orf72 locus starting from within endogenous exon 1 with a heterologous nucleotide sequence comprising from 5' to 3': a first human hexanucleotide flanking sequence comprising a sequence set forth as SEQ ID NO: 36, one to one-hundred (e.g., 36 or 92) repeats of the hexanucleotide sequence set forth as SEQ ID NO:1, a human hexanucleotide flanking sequence comprising a sequence set forth as SEQ ID NO:37, and a floxed drug resistance (neo') cassette, or upon excision of the neo gene, a lox recombinase recognition sequence.

In some embodiments, an isolated non-human cell or tissue of a non-human animal as described herein, or as made by a method described herein, is provided. In some embodiments, an isolated cell or tissue comprises a C9ORF72 locus as described herein. In some embodiments, a cell is a neuronal cell or a cell from a neuronal lineage. In some embodiments, an immortalized cell line is provided, which is made from an isolated cell of a non-human animal as described herein.

In some embodiments, a non-human embryonic stem cell is provided whose genome comprises a C9ORF72 locus as described herein. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C57BL strains.

Also described herein is a Clustered Regularly Interspersed Short Palindromic Repeats (CRISPR)/CRISPR-associated (Cas) system, or one or more components of a CRISPR/Cas system, which may be used to delete from a cell, e.g., an embryonic stem cell, a heterologous hexanucleotide repeat expansion sequence (or portion thereof) inserted an endogenous C9ORF72 locus as described herein. Such components include, for example, Cas proteins and/or guide RNAs (gRNAs), which gRNA may include two separate RNA molecules; e.g., targeter-RNA (e.g., CRISPR RNAs (crRNA) and activator RNA (e.g., tracrRNAs); or a single-guide RNA (e.g., single-molecule gRNA (sgRNA)).

CRISPR/Cas systems include transcripts and other elements involved in the expression of, or directing the activity of, Cas genes. A CRISPR/Cas system can be, for example, a type I, a type II, or a type III system. Alternatively, a CRISPR/Cas system can be a type V system (e.g., subtype V-A or subtype V-B). A heterologous hexanucleotide repeat expansion sequence (or portion thereof) inserted an endogenous C9ORF72 locus as described herein may be deleted by utilizing CRISPR complexes (comprising a guide RNA (gRNA) complexed with a Cas protein) for site-directed cleavage of nucleic acids.

A CRISPR/Cas system as described herein may comprise a Cas protein (e.g., Cas1, Cas1B, Cas2, Cas3, Cas4, Cas5, Cas5e (CasD), Cas6, Cas6e, Cas6f, Cas7, Cas8a1 , Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cu1966, and homologs or modified versions thereof) and/or one or more guide RNA (gRNA), which target(s) a gRNA recognition sequence. A CRISPR/Cas system as described herein may further comprise at least one expression construct, which comprises a nucleic acid encoding a Cas protein (e.g., which may be operably linked to a promoter) and/or DNA encoding a gRNA as described herein.

In some embodiments a gRNA recognition sequence, e.g., a target nucleic acid sequence to which a DNA-targeting segment of a gRNA will bind provided sufficient conditions for binding exist, is found in SEQ ID NO:45, or portion thereof. Site-specific binding and cleavage of SEQ ID NO:45 by Cas proteins can occur at locations determined by both (i) base-pairing complementarity between the gRNA and the target DNA and (ii) a short motif, called the protospacer adjacent motif (PAM), in the target DNA. The PAM can flank the guide RNA recognition sequence. Optionally, the guide RNA recognition sequence can be flanked on the 3' end by the PAM. Alternatively, the guide RNA recognition sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-$CCN_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In some cases (e.g., for FnCpf1), the PAM sequence can be upstream of the 5' end and have the sequence 5'-TTN-3'. In some embodiments, a gRNA recognition sequence starts at position 190, 196, 274, 899, 905, 1006, or 1068 of SEQ ID NO:45.

As disclosed herein, guide RNAs may be provided in any form. In some embodiments, gRNA can be provided in the form of RNA, either as two molecules (a separate crRNA and tracrRNA) or as one molecule (sgRNA), and optionally in the form of a complex with a Cas protein. The gRNA can also be provided in the form of DNA encoding the gRNA. In some embodiments, the DNA encoding the gRNA can encode a single RNA molecule (sgRNA) or separate RNA molecules (e.g., separate crRNA and tracrRNA) (wherein the separate RNA molecules may be provided as one DNA molecule, or as separate DNA molecules encoding the crRNA and tracrRNA, respectively).

In one embodiment, a CRISPR/Cas system as described herein comprises Cas9 protein or a protein derived from a Cas9 from a type II CRISPR/Cas system and/or at least one gRNA, wherein the at least one gRNA is encoded by DNA that encodes a crRNA and/or a tracrRNA. In some embodiments, a DNA encoding a crRNA comprises a sequence selected from the group consisting of AGTACTGTGAGAG-CAAGTAG (R) (SEQ ID NO:38), GCTCTCACAG-TACTCGCTGA (SEQ ID NO:39), CCGCAGCCTGTAG-CAAGCTC (SEQ ID NO:40), CGGCCGCTAGCGCGATCGCG (SEQ ID NO:41), ACGCCCCGCGATCGCGCTAG (R) (SEQ ID NO:42), TGGCGAGTGGGTGAGTGAGG (SEQ ID NO:43), GGAAGAGGCGCGGGTAGAAG (SEQ ID NO:44), GAGTACTGTGAGAGCAAGTAG (R) (SEQ ID NO:46), GCCGCAGCCTGTAGCAAGCTC (SEQ ID NO:47), GCGGCCGCTAGCGCGATCGCG (SEQ ID NO:48), GACGCCCCGCGATCGCGCTAG (R) (SEQ ID NO:49), and GTGGCGAGTGGGTGAGTGAGG (SEQ ID NO:50).

In one embodiment, a CRISPR/Cas system described herein comprises a combination of at least seven crRNA encoding sequences, wherein each of the seven crRNA encoding sequences comprises a sequence set forth as SEQ ID NO: 38, 39, 40, 41, 42, 43 or 44. In one embodiment, a CRISPR/Cas 9 system described herein comprises a combination of at least seven distinct crRNA encoding sequences, wherein each of the seven crRNA encoding sequences comprises a sequence set forth as SEQ ID NO: 46, 39, 47, 48, 49, 50 or 44. In one embodiment, a CRISPR/Cas 9 system described herein comprises a combination of at least three distinct crRNA encoding sequences, each comprising a sequence set forth as SEQ ID NO: 40, 43 or 44. In one embodiment, a CRISPR/Cas 9 system described herein comprises a combination of at least three distinct crRNA encoding sequences, each comprising a sequence set forth as SEQ ID NO: 47, 50 or 44. In one embodiment, a CRISPR/Cas 9 system described herein comprises a combination of at least four distinct crRNA encoding sequences, each comprising a sequence set forth as SEQ ID NO: 38, 39, 41 or 42. In one embodiment, a CRISPR/Cas 9 system described herein comprises a combination of at least four distinct crRNA encoding sequences, each comprising a sequence set forth as SEQ ID NO: 46, 39, 48, or 49.

In some embodiments, a gRNA disclosed herein is encoded by DNA encoding a tracrRNA. In some embodiments, the tracrRNA encoding sequence comprises a sequence set forth as SEQ ID NO:63, 64 or 65. In some embodiments a gRNA as described herein comprises a crRNA and a tracrRNA. In some embodiments, a gRNA as disclosed herein comprises one or more crRNA (e.g., encoded by DNA comprising a sequence set forth as SEQ ID NO: 38, 39, 40, 41, 42, 43, 44, 46, 47, 48, 49 or 50) and a tracrRNA, e.g., a DNA comprising a sequence set forth as SEQ ID NO:63, 64 or 65. In some embodiments, the DNA encoding the gRNA can encode a single RNA molecule (sgRNA) or separate RNA molecules (e.g., separate crRNA and tracrRNA) (wherein the separate RNA molecules may be provided as one DNA molecule, or as separate DNA molecules encoding the crRNA and tracrRNA, respectively).

Targeted genetic modifications can be generated by contacting a cell with a Cas protein and one or more guide RNAs that hybridize to one or more guide RNA recognition sequences within a target genomic locus. At least one of the one or more guide RNAs can form a complex with and can guide the Cas protein to at least one of the one or more guide RNA recognition sequences, and the Cas protein can cleave the target genomic locus within at least one of the one or more guide RNA recognition sequences. Cleavage by the Cas protein can create a double-strand break or a single-strand break (e.g., if the Cas protein is a nickase). The end sequences generated by the double-strand break or the single-strand break can then undergo recombination.

In some embodiments, a non-human germ cell is provided whose genome comprises a C9ORF72 locus as described herein. In some embodiments, a non-human germ cell is a rodent germ cell. In some certain embodiments, a rodent germ cell is a mouse germ cell and is from a 129 strain, C57BL strain, or a mixture thereof. In some certain embodiments, a rodent germ cell is a mouse germ cell and is a mixture of 129 and C57BL strains.

In some embodiments, the use of a non-human embryonic stem cell or germ cell as described herein is provided to make a genetically modified non-human animal. In some certain embodiments, a non-human embryonic stem cell or germ cell is a mouse embryonic stem cell or germ cell and is used to make a mouse comprising a C9ORF72 locus as described herein. In some certain embodiments, a non-human embryonic stem cell or germ cell is a rat embryonic stem cell germ cell and is used to make a rat comprising a C9ORF72 locus as described herein.

In some embodiments, a non-human embryo is provided comprising, made from, obtained from, or generated from a non-human embryonic stem cell comprising a C9ORF72 locus as described herein. In some certain embodiments, a non-human embryo is a rodent embryo; in some embodiments, a mouse embryo; in some embodiments, a rat embryo.

In some embodiments, the use of a non-human embryo as described herein is provided to make a genetically modified non-human animal. In some certain embodiments, a non-human embryo is a mouse embryo and is used to make a mouse comprising a C9ORF72 locus as described herein. In some certain embodiments, a non-human embryo is a rat embryo and is used to make a rat comprising a C9ORF72 locus as described herein.

In some embodiments, a non-human animal model of amyotrophic lateral sclerosis (ALS) or frontotemporal dementia (FTD) is provided, which non-human animal has an endogenous C9ORF72 locus comprising a heterologous hexanucleotide repeat expansion sequence as disclosed herein.

In some embodiments, a non-human animal model of amyotrophic lateral sclerosis (ALS) or frontotemporal dementia (FTD) is provided, which is obtained by an insertion of a heterologous hexanucleotide repeat expansion sequence in an endogenous C9ORF72 locus.

In some embodiments, a method for identifying a therapeutic candidate for the treatment of a neurodegenerative disease, disorder or condition is provided, the method comprising (a) administering a candidate agent to a non-human animal or non-human animal cell (e.g., embryonic stem cell, an embryonic stem cell-derived motor neuron, a brain cell, a cortical cell, a neuronal cell, a muscle cell, a heart cell) whose genome comprises an endogenous C9ORF72 locus modified as described herein; (b) performing one or more assays to determine if the candidate agent has a modulating effect on one or more signs, symptoms and/or conditions associated with the disease, disorder or condition (e.g., increased transcription of sense or antisense C9orf72 RNA from the C9orf72 locus, increased nuclear and/or cytoplasmic RNA foci comprising sense or antisense C9orf72 RNA, increased RAN translation products (e.g., dipeptide repeat proteins); and (c) identifying the candidate agent that has a modulating effect on the one or more signs, symptoms and/or conditions associated with the disease, disorder or condition as the therapeutic candidate. In some embodiments, the disease or condition is selected from the group consisting of a neurodegenerative disease or condition. In some embodiments, the candidate agent is administered in vivo to a non-human animal as described herein, and one or more assays are performed on tissue comprising a brain cell, a cortical cell, a neuronal cell, a muscle cell, a heart cell, or a germ cell isolated from the non-human animal after administration. In some embodiments, the candidate agent is administered to a cell (e.g., an embryonic stem cell, an embryonic stem cell-derived motor neuron, a brain cell, a cortical cell, a neuronal cell, a muscle cell, a heart cell) comprising a hexanucleotide repeat expansion sequence at the C9orf72 locus as described herein, and the assay performed, in vitro. In some embodiments, the assay is quantitative polymerase chain reaction (qPCR) to detect C9orf72 gene products, e.g., sense and antisense C9orf72 RNA. In some embodiments, qPCR may be performed with a primer and/or probe having a nucleotide sequence set forth in SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, or any combination thereof. In some embodiments, the assay measures RNA foci comprising a C9orf72 sense or antisense RNA transcript, e.g., an RNA transcript of a hexanucleotide repeat expansion sequence. In some embodiments, the assay that measures RNA foci comprising a C9orf72 sense or antisense RNA transcript, e.g., an RNA transcript of a hexanucleotide repeat expansion sequence, using one or more probes having a nucleotide sequence as set forth in any one of SEQ ID NO:81, SEQ ID NO:82, SEQ ID NO:83, and/or SEQ ID NO:84. In some embodiments, the assay is measures RAN translation products, e.g., the assay is immunofluorescence and RAN translation products (e.g., dipeptide repeat proteins, e.g., polyGA dipeptide repeat proteins) are measured with an anti-polyGA antibody. In some embodiments, the assay is measures C9orf72 protein levels.

In some embodiments, use of a non-human animal as described herein is provided in the manufacture of a medicament for the treatment of a neurodegenerative disease, disorder or condition.

In some embodiments, a neurodegenerative disease, disorder or condition is amyotrophic lateral sclerosis (ALS). In some embodiments, a neurodegenerative disease, disorder or condition is frontotemporal dementia (FTD).

In various embodiments, one or more phenotypes as described herein is or are as compared to a reference or control. In some embodiments, a reference or control includes a non-human animal having a modification as described herein, a modification that is different than a modification as described herein, or no modification (e.g., a wild type non-human animal). Non-human animals comprising a heterologous hexanucleotide repeat expansion sequence comprising a sequence set forth as SEQ ID NO:2, a variant thereof, SEQ ID NO: 4, a variant thereof, or SEQ ID NO:5, or a variant thereof, may exhibit a wildtype phenotype, e.g., may be used as a reference, or control, non-human animal in the methods described herein.

In various embodiments, a non-human animal is homozygous for the C9orf72 locus described herein. In various embodiments, the non-human animal is heterozygous for the C9orf72 locus described herein.

In various embodiments, a non-human animal described herein is a rodent; in some embodiments, a mouse; in some embodiments, a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of non-human animals, cells and methods provided herein are apparent in the detailed description of certain embodiments that follows. It should be understood, however, that the detailed description, while indicating certain embodiments, is given by way of illustration only, not limitation. Various changes and modifications within the scope of the invention will become apparent to those skilled in the art from the detailed description.

BRIEF DESCRIPTION OF THE DRAWINGS

The Drawings included herein, which is composed of the following Figures, is for illustration purposes only and not for limitation. The patent or application file contains at least one drawing executed in color. Copies of this patent or patent application publication with the color drawing(s) will be provided by the United States Patent and Trademark Office upon request and payment of the necessary fee.

In FIG. 1A, white filled boxes represent mouse exons, with white diagonally striped boxes representing non-coding mouse exons of the mouse C9orf72 locus. Horizontally striped boxes are non-coding exons of a human C9orf72 locus and the diamond represents the hexanucleotide repeat. A first targeting vector comprising a sequence set forth as SEQ ID NO:2 and a second targeting vector comprising a sequence set forth as SEQ ID NO:4 were generated. The first targeting vector includes from 5' to 3': a mouse homology arm 89 Kb upstream from RP23-434N2 of mouse the 3110043021Rik gene and comprising SEQ ID NO:6, a human sequence set forth as SEQ ID NO:8 which spans non-coding exons 1a and 1b of human C9orf72 and includes the intervening intron containing three repeats of the hexanucleotide sequence GGGGCC; a drug selection cassette that comprises a promoter from the human ubiquitin 1 gene (hUb 1) and the bacterial Em7 gene operably linked to a neomycin phosphotransferase resistance gene (neo-r) and is flanked by loxP sites), and a mouse homology arm 86 Kb downstream from RP23-434N2 of mouse the 3110043021Rik gene and comprising SEQ ID NO:7. The second targeting vector includes from 5' to 3': a mouse homology arm 89 Kb upstream from RP23-434N2 of mouse the 3110043021Rik gene and comprising SEQ ID NO:6; a human sequence set forth as SEQ ID NO:9 which spans non-coding exons 1a and 1b of human C9orf72 and includes the intervening intron containing 100 repeats of the hexanucleotide sequence GGGGCC; a drug selection cassette that comprises a promoter from the human ubiquitin 1 gene (hUb1) and the bacterial Em7 gene operably linked to a neomycin phosphotransferase resistance gene (neo-r) and is flanked by loxP sites); and a mouse homology arm 86 Kb downstream from RP23-434N2 of mouse the 3110043021Rik gene and comprising SEQ ID NO:7. Upon homologous recombination with the first or second targeting vector, a mouse genomic region of about 853 bp, including a portion of exon 1 and part of intron 1 of mouse 3110043021Rik is replaced with a sequence comprising the genomic sequence spanning exons 1a-1b of the human C9orf72 non-coding sequence. The resulting modified mouse C9orf72-HRE$_3$ loci before and after excision of the drug resistance cassette are depicted in FIG. 1B. The resulting modified mouse C9orf72-HRE$_{100}$ loci before and after excision of the drug resistance cassette are depicted in FIG. 1C.

Shown in FIG. 2A is the result of Southern blot analysis of genomic DNA isolated from control ES cell clones, ES cell clones targeted with a targeting vector comprising a heterologous repeat expansion sequence comprising three repeats of the hexanucleotide sequence (8026) and after excision of the drug cassette (8027 A-C4), or ES cell clones targeted with a targeting vector comprising a heterologous repeat expansion sequence comprising 100 repeats of the hexanucleotide sequence (8028) and after excision of the drug cassette (8029 A-A3, 8029 A-A6, 8029 B-A4, 8029 B-A10).

In FIG. 3, murine non-coding regions are represented by diagonally striped boxes, human non-coding exons are represented by horizontally striped boxes, and mouse coding exons are represented by white boxes. The sequences for the primers and probes depicted in FIG. 3 and described in Table 1 are provided in Table 5.

TABLE 1

| Analyses | Location of 5'-primer | Location of 3'-primer | Location of probe |
|---|---|---|---|
| A | Mouse exon 1a | Human exon 1a | Spans junction of mouse exon 1a and human exon 1a |
| B | Human exon 1a | Mouse exon 2 | Human intron 2 |
| G | Human Intron 2 | Human Intron 2 | Human Intron 2 |
| H | Human Intron 2 | Human Intron 2 | Human Intron 2 |
| D | Mouse Exon 5 | Mouse Exon 6 | Mouse Intron 6 |

Figure 3:
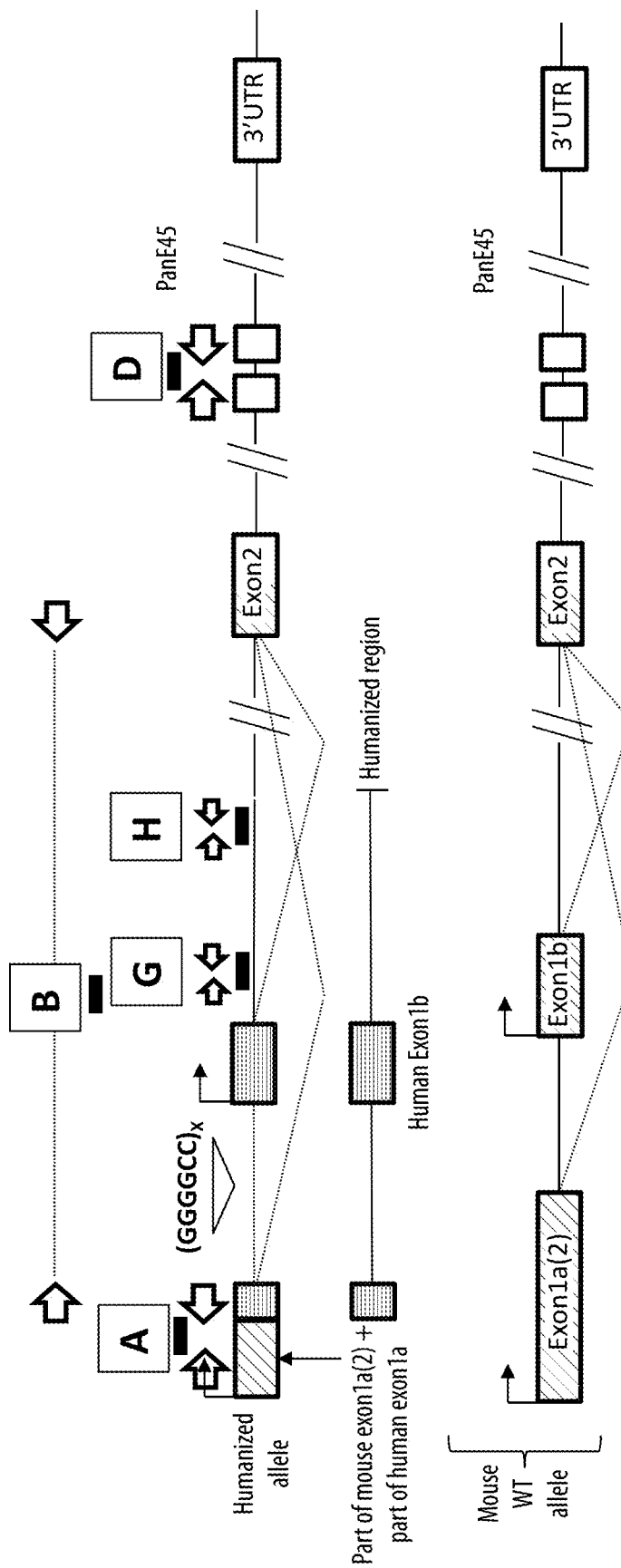
FIG. 3 shows a schematic illustration, not to scale, of the humanized C9orf72-HREx (where x≥1), the humanized region, and the wildtype (WT) C9orf72 mouse loci. Also shown in FIG. 3 are the approximate locations of 5'- and 3'-primers (white arrows) and probes (filled rectangles) used in the TAQMAN® qualitative PCR analyses A, B, G, H, and D described in Table 1 to quantify gene expression products from the modified C9orf72-HRE loci (A, B, G, H) or both the modified and wildtype C9orf72 loci (D).
Figure 4:
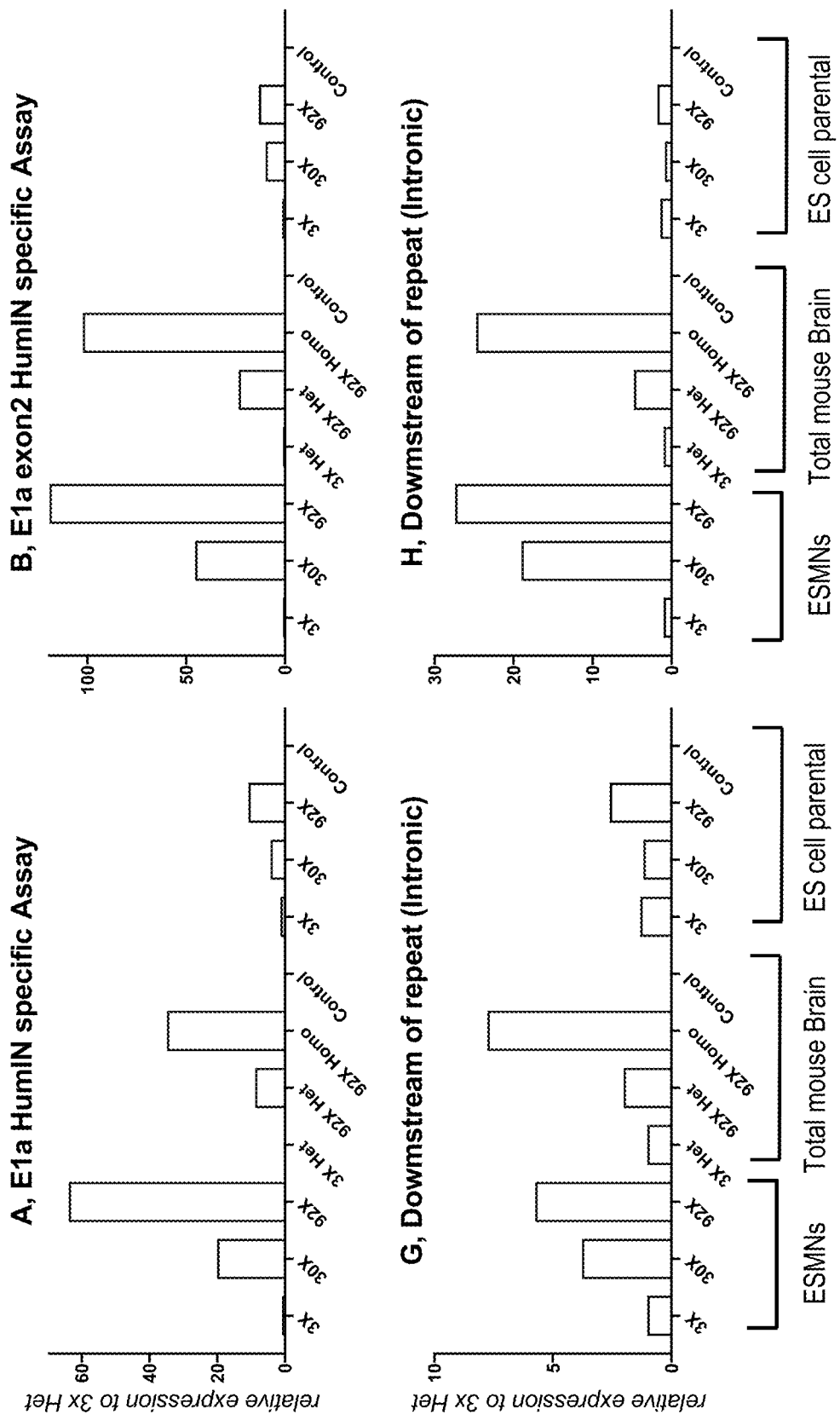

FIG. 4 provides bar graphs showing expression levels (as determined by the TAQMAN® qualitative PCR assays A, B, G, and H depicted in FIG. 3) of the C9orf72 locus (y-axis) by embryonic stem cell derived motor neurons (ESMNs), total brain tissue, or parental embryonic stem (ES) cells that are heterozygous (Het) or homozygous (Homo) for a wildtype C9orf72 locus (control) or a modified C9orf72 locus comprising three (3×), thirty (30×) or ninety-two (92×) repeats of the hexanucleotide sequence set forth as SEQ ID NO:1 relative to ESMNs, brain, or parental ESCs, respectively, that are heterozygous for a modified C9orf72 locus comprising three (3×) repeats of the hexanucleotide sequence set forth as SEQ ID NO:1. All ESMNs and parental ES cells were heterozygous for the modified C9orf72 loci, and all controls were homozygous for the wildtype C9orf72 locus.

Figure 5A:
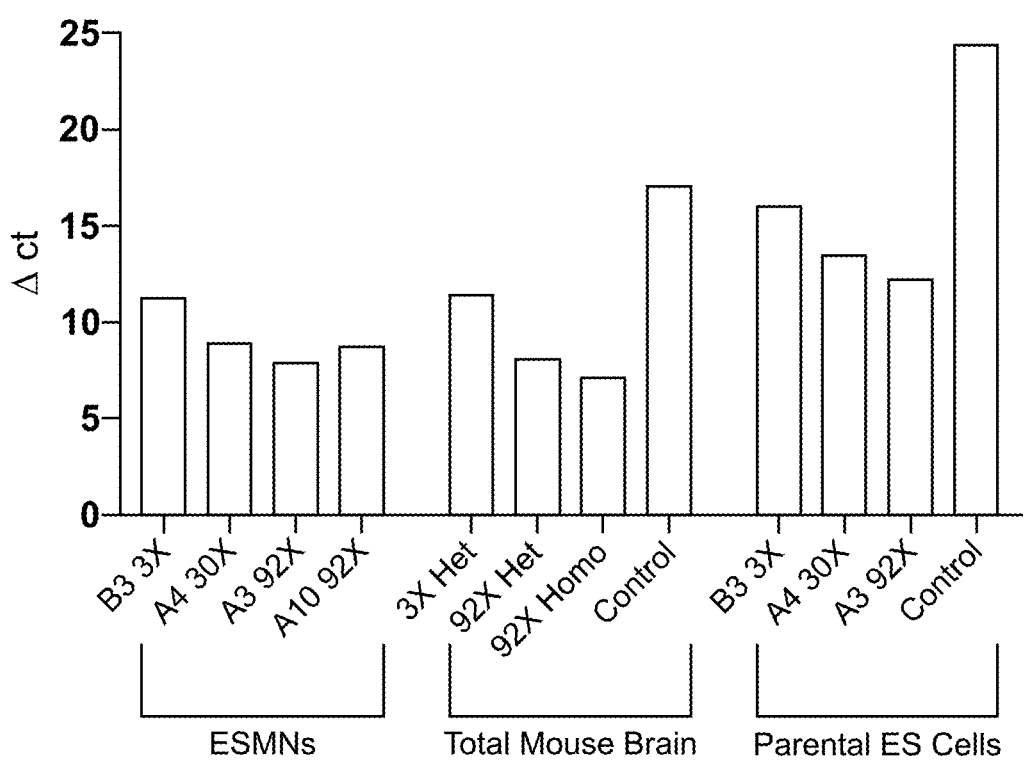
Figure 5B:
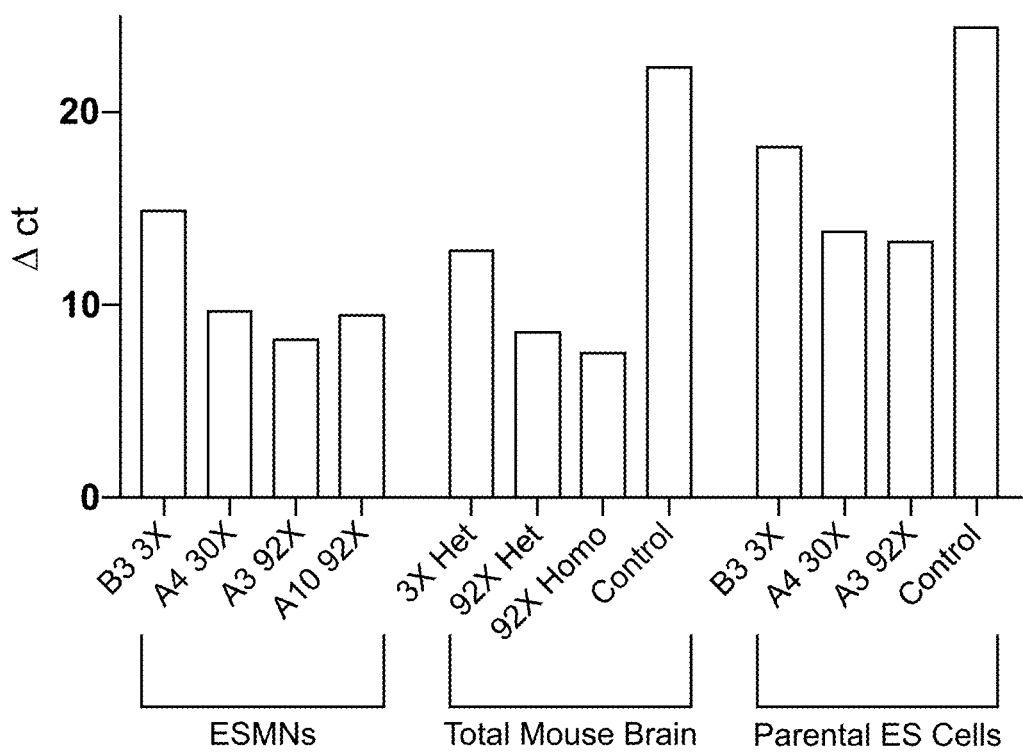
Figure 5C:
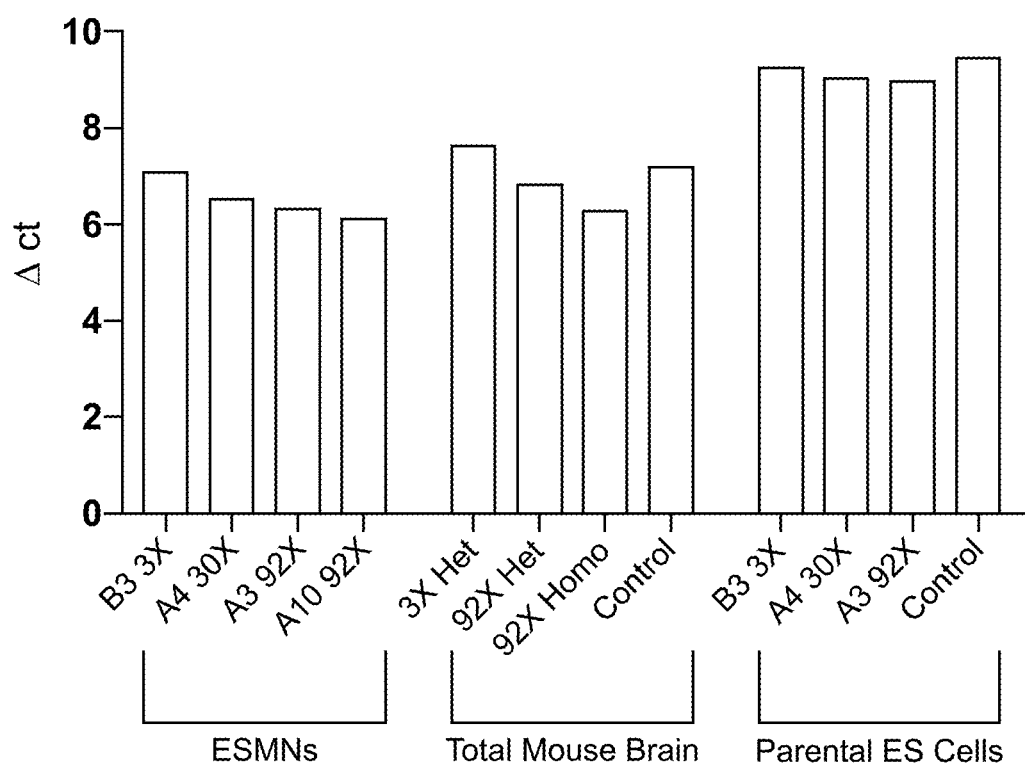

FIGS. 5A-5C provides bar graphs showing the differences in the count values (Δ ct; y-axis) of C9orf72 gene products (detected by the TAQMAN® qualitative PCR assay A (FIG. 5A), assay B (FIG. 5B), or assay D (FIG. 5C) as depicted in FIG. 3) by embryonic stem cell derived motor neurons (ESMNs), total mouse brain, or parental embryonic stem (ES) cells that are heterozygous (het) or homozygous (homo) for a wildtype C9orf72 locus (Controls) or a modified C9orf72 locus comprising three (3×), thirty (30×) or ninety-two (92×) repeats of the hexanucleotide sequence set forth as SEQ ID NO:1 and the count values of GAPDH gene products. All ESMNs and parental ES cells were heterozygous for the modified C9orf72 loci, and all controls were homozygous for the wildtype C9orf72 locus.

Figure 6:
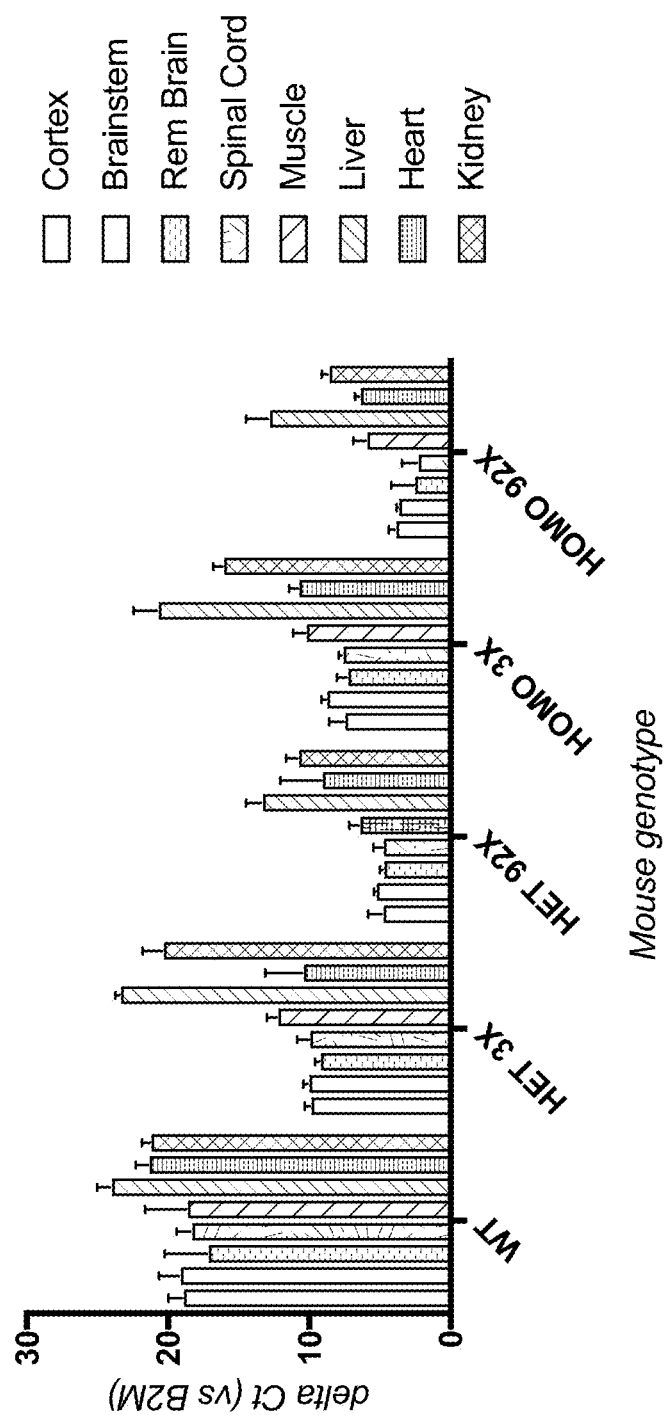

FIG. 6 provides bar graphs showing the differences in the count values (Δ ct; y-axis) of C9orf72 gene products (detected by the TAQMAN® qualitative PCR assay B as depicted in FIG. 3) in tissues isolated from the cortex, brainstem, remaining (rem) brain, spinal cord, muscle, liver, heart, or kidneys of mice heterozygous (het) or homozygous (homo) for a wildtype C9orf72 locus (WT) or a modified c9orf72 locus comprising three (3×) or ninety-two (92×) repeats of the hexanucleotide sequence set forth as SEQ ID NO:1 and the count values of β-microglobulin (B2M) gene products.

Figure 7:
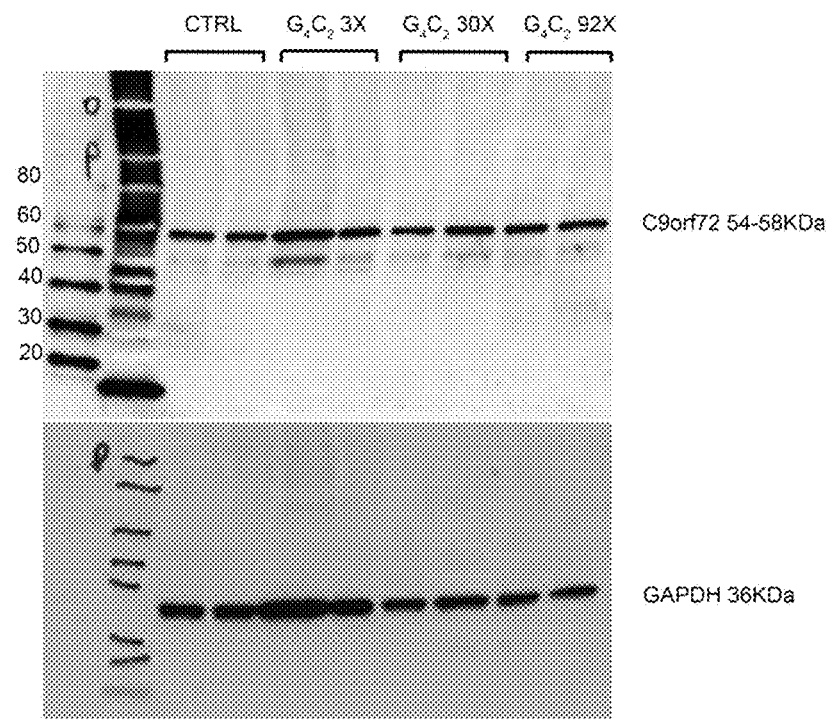
Figure 7:
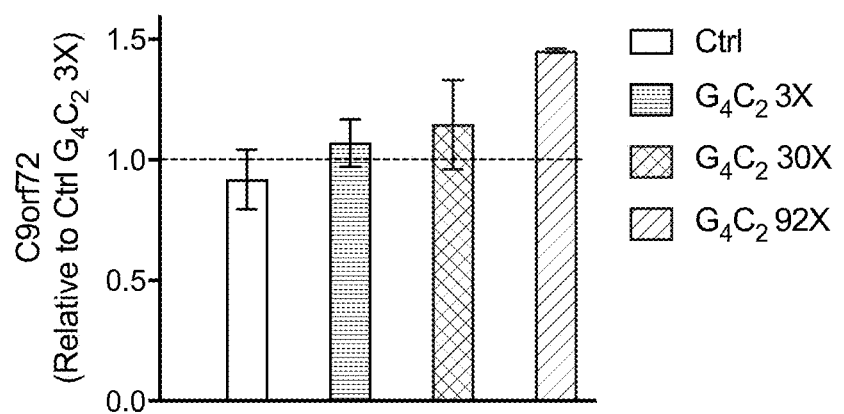

FIG. 7 shows Western blot images (top) from reducing SDS-PAGE analysis of lysates from embryonic stem cell—derived motor neurons (ESMNs) homozygous for a wildtype C9orf72 locus (CTRL) or heterozygous for a modified C9orf72 locus comprising three ($G_4C_2$3×), thirty ($G_4C_2$30×) or ninety-two ($G_4C_2$92×) repeats of the hexanucleotide sequence set forth as SEQ ID NO:1, blotted with anti-C9orf72 antibody (top) or anti-GAPDH antibody (bottom). Bar graphs (bottom panel) of the protein levels of C9orf72 of these samples normalized to protein levels of C9orf72 of ESMNs heterozygous for a modified C9orf72 locus comprising three repeats of the hexanucleotide sequence set forth as SEQ ID NO:1 are also provided, as are molecular weight markers.

Figure 8:
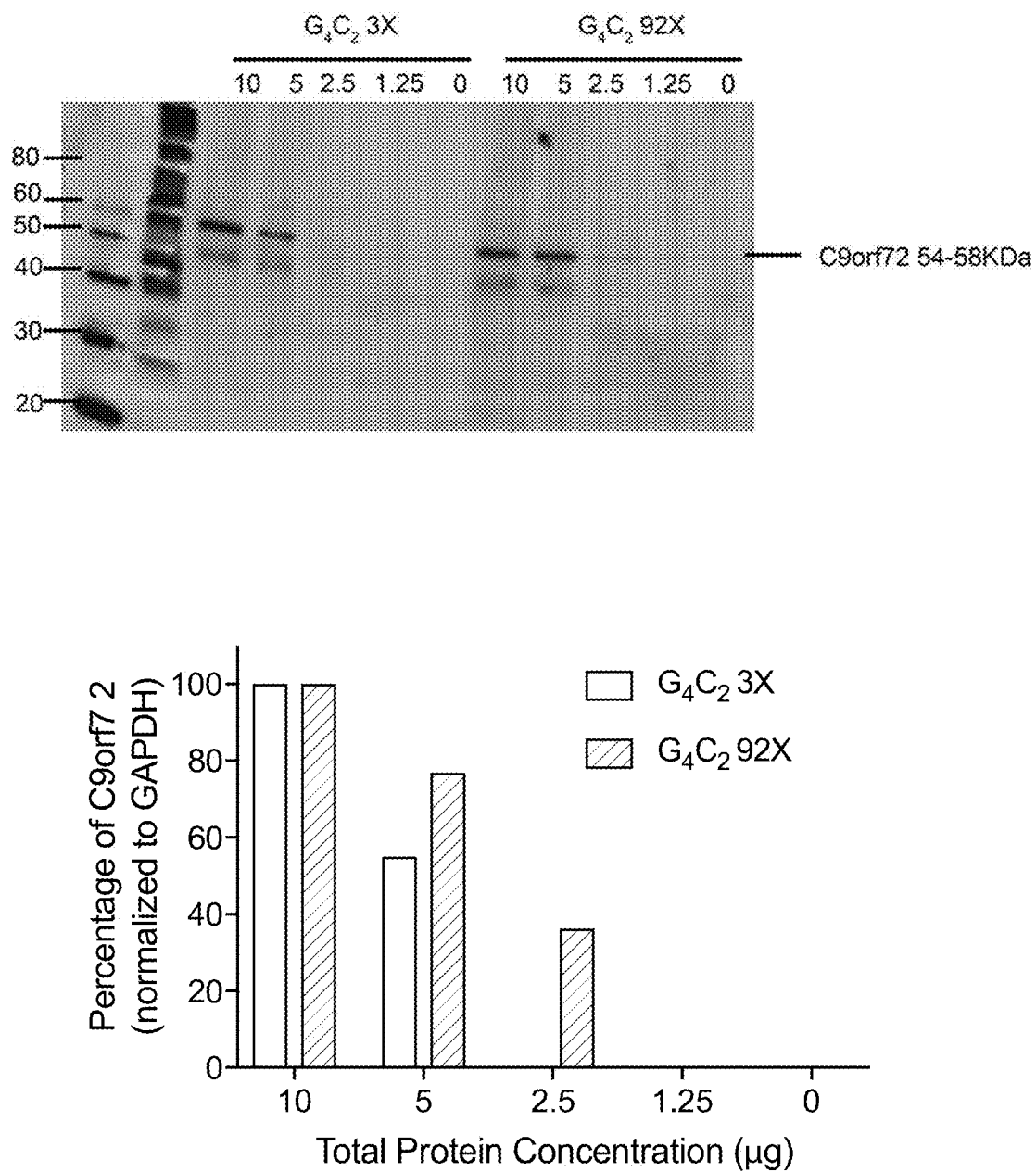

FIG. 8 shows a Western blot image (top) from reducing SDS-PAGE analysis of lysates of from embryonic stem cell-derived motor neurons (ESMNs) heterozygous for a modified C9orf72 locus comprising three ($G_4C_2$3×) or ninety-two ($G_4C_2$92×) repeats of the hexanucleotide sequence set forth as SEQ ID NO:1. Lysates containing 0 μg, 1.25 μg, 2.5 μg, 5 μg, or 10 μg total proteins are blotted with anti-C9orf72 antibody (shown) or anti-GAPDH antibody (data not shown). Bar graphs (bottom) of the protein levels of C9orf72 of these samples normalized to protein levels of GAPDH by these samples are also provided, as are molecular weight markers.

Figure 9A:
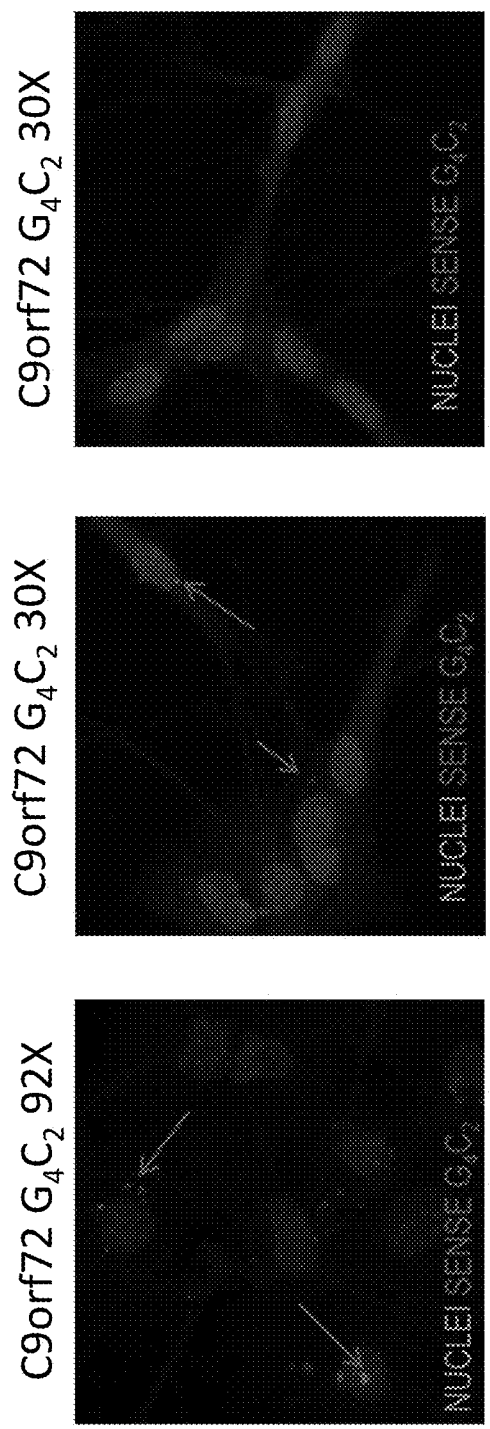
Figure 9B:
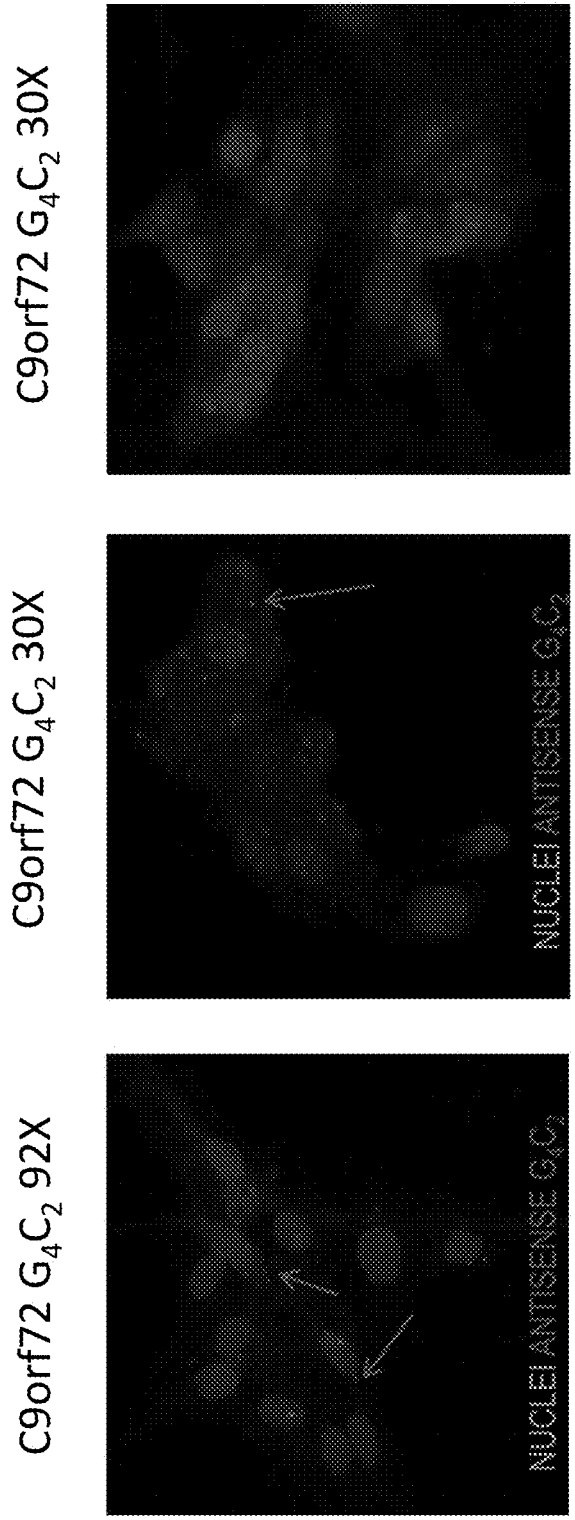

FIGS. 9A and 9B are images obtained from fluorescent in situ hybridization (FISH) of embryonic stem cell derived motor neurons (ESMNs) heterozygous for a C9orf72 locus modified to comprise three (C9orf72 $G_4C_2$ 3×), thirty (C9orf72 $G_4C_2$ 30×) or ninety-two (C9orf72 $G_4C_2$ 92×) repeats of the hexanucleotide sequence set forth as SEQ ID NO:1 stained with DNA (FIG. 9A) or LNA (FIG. 9B) probes, which images show the nuclear and cytoplasmic locations of sense (FIG. 9A) or antisense (FIG. 9B) transcripts of the hexanucleotide repeat sequence set forth in SEQ ID NO:1 in the ESMNs. Arrows point to exemplary stained RNA foci.

Figure 10:
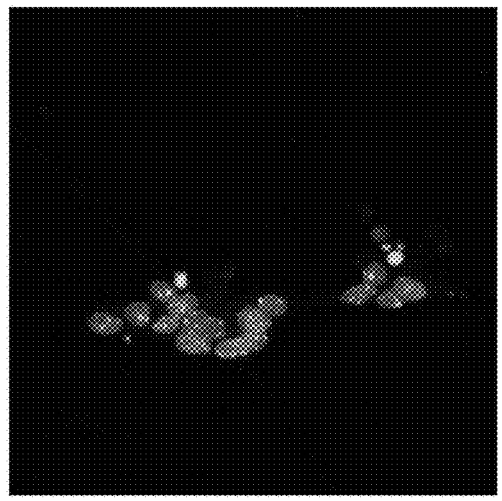
Figure 10:
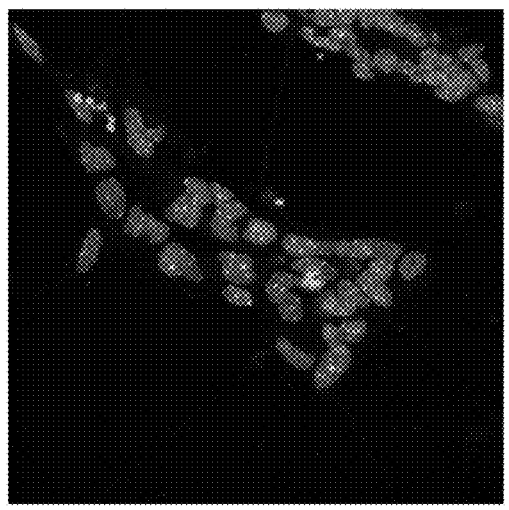
Figure 10:
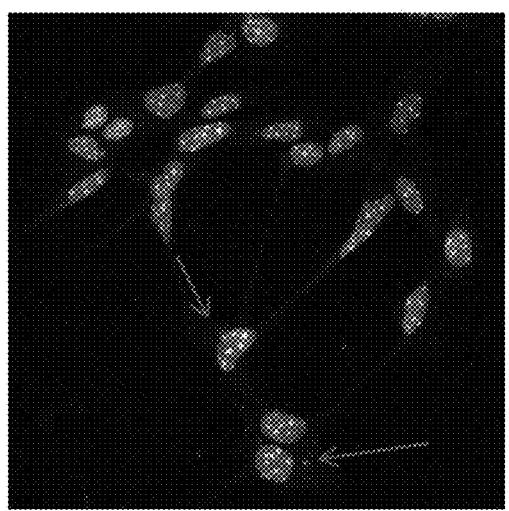

FIG. 10 provides images obtained from immunofluorescence of embryonic stem cell derived motor neurons (ESMNs) heterozygous for a C9orf72 locus modified to comprise three (C9orf72 $G_4C_2$ 3×) or ninety-two (C9orf72 $G_4C_2$ 92×) repeats of the hexanucleotide sequence set forth as SEQ ID NO:1, which images show the nuclear locations of dipeptide repeat proteins (polyGA) translated (through RAN translation, a non-AUG mechanism) from transcripts of the hexanucleotide repeat sequence set forth in SEQ ID NO:1 in the ESMNs. Arrows point to exemplary stained polyGA dipeptide repeat proteins.

Figure 11:
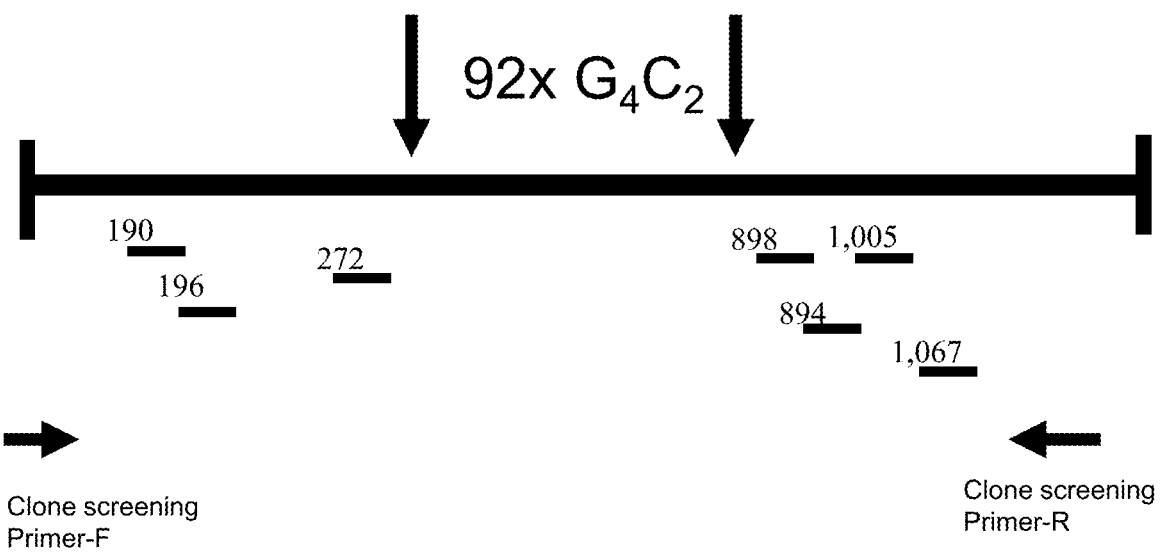

FIG. 11 shows a schematic illustration, not to scale, of about 1300 bp of a mouse C9ORF72 locus comprising a heterologous (human) hexanucleotide repeat expansion comprising about 92 repeats of the hexanucleotide sequence set forth as SEQ ID NO:1, and which may be used as a reference sequence to generate a CRISPR/Cas system for the deletion of the expansion sequence. Also depicted in FIG. 11 are the approximate locations of (1) the 92 repeats of the hexanucleotide sequence depicted by downward pointing arrows, (2) the starting positions (190, 196 and 274) of three sites upstream of the hexanucleotide repeat expansion sequence that may be targeted by gRNA respectively comprising the sequence set forth as SEQ ID NO:38, SEQ ID NO:39, and SEQ ID NO:40, (3) the starting positions (899, 905 1006 and 1068) of four sites downstream of the hexanucleotide repeat expansion sequence that may be targeted by gRNA respectively comprising the sequence set forth as SEQ ID NO:41, SEQ ID NO:42, SEQ ID NO:43 and SEQ ID NO:44, and (4) the approximate locations for forward (F-) and reverse (R-) primers that may be used to confirm the deletion in selected cell clones. The nucleic acid sequence of the reference sequence depicted in FIG. 11 is set forth as SEQ ID NO:45.

Figure 12:
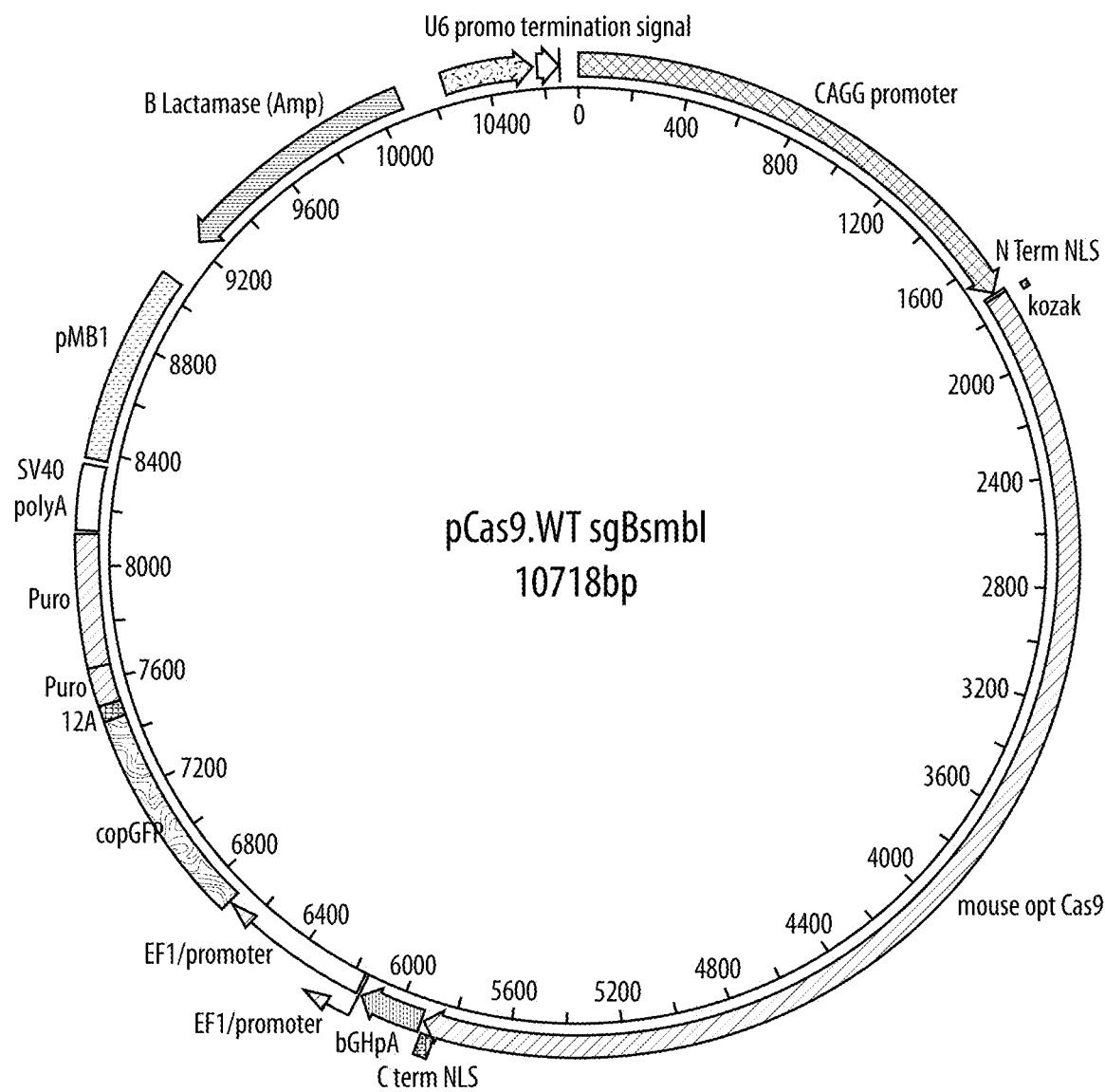

FIG. 12 shows an exemplary 10,718 bp expression construct that may be used in a CRISP/Cas system. The expression construct comprises a nucleic acid encoding a mouse Cas9 protein "mouse opt Cas9" fused with an N-terminal nuclear localization signal (NLS) and C-terminal nuclear localization signal, the expression of the fusion protein being under the control of a CAGG promoter. Upstream of the nucleic acid is a kozak sequence, and downstream of the nucleic acid is a bovine growth hormone polyadenylation (bGHpA) tail. Also shown as part of the expression construct are an EF1 promoter driving the expression of a nucleotide sequence encoding a green fluorescence protein (GFP) fused with a puromycin resistance gene operably linked to an SV40 polyadenylation (SV40 polyA) tail, an origin of replication site (pMB1), and a β lactamase gene providing ampicillin (Amp) resistance. The expression construct allows for the insertion of DNA encoding gRNA, e.g., a crRNA, between a U6 promoter and a termination signal. An expression construct has depicted in FIG. 4 may further comprise, downstream of the U6 promoter and upstream a termination signal, a tracrRNA encoding sequence. Such tracrRNA encoding sequence is placed such that it may be operably linked to the, e.g., crRNA, upon its insertion. In some embodiments, a tracrRNA encoding sequence comprises
GTTGGAACCATTCAAAACAGCATAGCAAGT-TAAAATAAGGCTAGTCCGTTATCA ACTT-GAAAAAGTGGCACCGAGTCGGTGC (SEQ ID NO:63);
GTTTTAGAGCTAGAAATAGCAAGT-TAAAATAAGGCTAGTCCGTTATCAACTTGA AAAAGTGGCACCGAGTCGGTGC (SEQ ID NO:64);
GTTTAAGAGCTATGCTGGAAACAGCATAGCAAGTT-TAAATAAGGCTAGTCCGTT ATCAACTT-GAAAAAGTGGCACCGAGTCGGTGC (SEQ ID NO:65), or portions thereof.

DEFINITIONS

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

"Administration" includes the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human or a rodent) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

"Amelioration" includes the prevention, reduction or palliation of a state, or improvement of the state of a subject. Amelioration includes, but does not require complete recovery or complete prevention of a disease, disorder or condition (e.g., radiation injury).

"Approximately", as applied to one or more values of interest, includes to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Biologically active" includes a characteristic of any agent that has activity in a biological system, in vitro or in vivo (e.g., in an organism). For instance, an agent that, when present in an organism, has a biological effect within that organism is considered to be biologically active. In particular embodiments, where a protein or polypeptide is biologically active, a portion of that protein or polypeptide that shares at least one biological activity of the protein or polypeptide is typically referred to as a "biologically active" portion.

"Comparable" includes two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conservative", when describing a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256: 1443-1445. In some embodiments, a substitution is a moderately conservative substitution wherein the substitution has a nonnegative value in the PAM250 log-likelihood matrix.

"Control" includes the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

"Disruption" includes the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product. In some such embodiments, a disruption may achieve assembly of a fusion protein. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

"Determining", "measuring", "evaluating", "assessing", "assaying" and "analyzing" includes any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

"Endogenous locus" or "endogenous gene"" includes a genetic locus found in a parent or reference organism prior to introduction of a disruption, deletion, replacement, alteration, or modification as described herein. In some embodiments, the endogenous locus has a sequence found in nature. In some embodiments, the endogenous locus is a wild type locus. In some embodiments, the reference organism is a wild type organism. In some embodiments, the reference organism is an engineered organism. In some embodiments, the reference organism is a laboratory-bred organism (whether wild type or engineered).

"Endogenous promoter" includes a promoter that is naturally associated, e.g., in a wild type organism, with an endogenous gene.

"Gene" includes a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity we note that, as used in the present application, the term "gene" generally refers to a portion of a nucleic acid that encodes a polypeptide; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

"Heterologous" includes an agent or entity from a different source. For example, when used in reference to a polypeptide, nucleic acid sequence, gene, or gene product present in a particular cell or organism, the term clarifies that the relevant polypeptide, nucleic acid sequence, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type). "Heterologous" also includes a polypeptide, nucleic acid sequence, gene or gene product that is normally present in a particular native cell or organism, but has been modified, for example, by mutation or placement under the control of non-naturally associated and, in some embodiments, non-endogenous regulatory elements (e.g., a promoter).

"Host cell" includes a cell into which a nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the phrase "host cell". In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *Escherichia coli, Bacillus* spp., *Streptomyces* spp., etc.), mycobacteria cells, fungal cells, yeast cells (e.g., *Saccharomyces cerevisiae, Schizosaccharomyces pombe, Pichia pastoris, Pichia methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

"Identity", in connection with a comparison of sequences, includes identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

"Improve", "increase", "eliminate", or "reduce" includes indicated values that are relative to a baseline measurement, such as a measurement in the same individual (or animal) prior to initiation of a treatment described herein, or a measurement in a control individual (or animal) or multiple control individuals (or animals) in the absence of the treatment described herein.

"Isolated" includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. In some embodiments, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

"Locus" or "Loci" includes a specific location(s) of a gene (or significant sequence), DNA sequence, polypeptide-encoding sequence, or position on a chromosome of the genome of an organism. For example, a "C9ORF72 locus" may refer to the specific location of a C9ORF72 gene, C9ORF72 DNA sequence, C9ORF72-encoding sequence, or C9ORF72 position on a chromosome of the genome of an organism that has been identified as to where such a sequence resides. A C9ORF72 locus may comprise a regulatory element of a C9ORF72 gene, including, but not limited to, an enhancer, a promoter, 5' and/or 3' UTR, or a combination thereof. Those of ordinary skill in the art will appreciate that chromosomes may, in some embodiments, contain hundreds or even thousands of genes and demonstrate physical co-localization of similar genetic loci when comparing between different species. Such genetic loci can be described as having shared synteny.

"Non-human animal" includes any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

"Nucleic acid" includes any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" includes one or more exons. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

"Operably linked" includes a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" includes polynucleotide sequences, which are necessary to affect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site and transcription termination sequence, while in eukaryotes typically such control sequences include promoters and transcription termination sequence. The term "control sequences" is intended to include components whose presence is essential for expression and processing, and can also include additional components whose presence is advantageous, for example, leader sequences and fusion partner sequences.

"Phenotype" includes a trait, or to a class or set of traits displayed by a cell or organism. In some embodiments, a particular phenotype may correlate with a particular allele or genotype. In some embodiments, a phenotype may be discrete; in some embodiments, a phenotype may be continuous.

"Physiological conditions" includes its art-understood meaning referencing conditions under which cells or organisms live and/or reproduce. In some embodiments, the term includes conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide" includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

"Prevent" or "prevention" in connection with the occurrence of a disease, disorder, and/or condition, includes reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Reference" includes a standard or control agent, animal, cohort, individual, population, sample, sequence or value against which an agent, animal, cohort, individual, population, sample, sequence or value of interest is compared. In some embodiments, a reference agent, animal, cohort, individual, population, sample, sequence or value is tested and/or determined substantially simultaneously with the testing or determination of the agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. A "reference" also includes a "reference animal". A "reference animal" may have a modification as described herein, a modification that is different as described herein or no modification (i.e., a wild type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

"Response" includes any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a neuron's response. Neuron or subject response may be measured according to a wide variety of criteria, including clinical criteria and objective criteria. Examination of the motor system of a subject may include examination of one or more of strength, tendon reflexes, superficial reflexes, muscle bulk, coordination, muscle tone, abnormal movements, station and gait. Techniques for assessing response include, but are not limited to, clinical examination, stretch flex (myotatic reflex), Hoffmann's reflex, and/or pressure tests. Methods and guidelines for assessing response to treatment are discussed in Brodal, A.: Neurological Anatomy in Relation to Clinical Medicine, ed. 2, New York, Oxford University Press, 1969; Medical Council of the U.K.: Aids to the Examination of the Peripheral Nervous System, Palo Alto, Calif., Pendragon House, 1978; Monrad-Krohn, G. H., Refsum, S.: The Clinical Examination of the Nervous System, ed. 12, London, H. K. Lewis & Co., 1964; and Wolf, J. K.: Segmental Neurology, A Guide to the Examination and Interpretation of Sensory and Motor Function, Baltimore, University Park Press, 1981. The exact response criteria can be selected in any appropriate manner, provided that when comparing groups of neurons and/or patients, the groups to be compared are assessed based on the same or comparable criteria for determining response rate. One of ordinary skill in the art will be able to select appropriate criteria.

"Risk", as will be understood from context, of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 and up to 100%. In some embodiments, risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0,1, 2, 3, 4, 5, 6, 7, 8, 9, 10, or more.

"Substantially" includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial homology" includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non polar" side chains. Substitution of one amino acid for another of the same type may often be considered a "homologous" substitution. Typical amino acid categorizations are summarized below.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |

-continued

| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof. In some embodiments, the relevant stretch is at least 10, 15, 20, 25, 30, 35, 40, 45, 50, or more residues.

"Substantial identity" includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

"Targeting vector," "targeting construct" or "nucleic acid construct" includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct as described herein further comprises a nucleic acid sequence or gene (e.g., a reporter gene or homologous or heterologous gene) of particular interest, a selectable marker, control and or regulatory sequences, and other nucleic acid sequences that encodes a recombinase or recombinogenic protein. In some embodiments, a targeting construct may comprise a gene of interest in whole or in part, wherein the gene of interest encodes a polypeptide, in whole or in part, that has a similar function as a protein encoded by an endogenous sequence. In some embodiments, a targeting construct may comprises a humanized gene of interest, in whole or in part, wherein the humanized gene of interest encodes a polypeptide, in whole or in part, that has a similar function as a polypeptide encoded by an endogenous sequence. In some embodiments, a targeting construct may comprise a reporter gene, in whole or in part, wherein the reporter gene encodes a polypeptide that is easily identified and/or measured using techniques known in the art.

"Transgenic animal", "transgenic non-human animal" or "Tg+" includes any non-naturally occurring non-human animal in which one or more of the cells of the non-human animal contain heterologous nucleic acid and/or gene encoding a polypeptide of interest, in whole or in part. In some embodiments, a heterologous nucleic acid and/or gene is introduced into the cell, directly or indirectly by introduction into a precursor cell, by way of deliberate genetic manipulation, such as by microinjection or by infection with a recombinant virus. The term genetic manipulation does not include classic breeding techniques, but rather is directed to introduction of recombinant DNA molecule(s). This molecule may be integrated within a chromosome, or it may be extrachromosomally replicating DNA. The term "Tg+" includes animals that are heterozygous or homozygous for a heterologous nucleic acid and/or gene, and/or animals that have single or multi-copies of a heterologous nucleic acid and/or gene.

"Treatment", "Treat" or "Treating" includes any administration of a substance (e.g., a therapeutic candidate) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

"Variant" includes an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, or 2% of the residues in the variant are substituted as compared with the parent. In some embodiments, a "variant" has 10, 9, 8, 7, 6, 5, 4, 3, 2, or 1 substituted residue(s) as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide. In some embodiments, a non-human animal will comprise a variant of a nucleic acid construct used for targeted insertion of a heterologous hexanucleotide expansion sequence. As non-limiting examples, such nucleic acid constructs may comprise a 5' first heterologous hexanucleotide flanking sequence, n repeats of the hexanucleotide sequence set forth as SEQ ID NO:1, a 3' second heterologous hexanucleotide flanking sequence, and optionally, a drug resistance reporter gene preferably flanked by recombinase recognition sequences. As shown in Example 1, an animal resulting from the targeted insertion may comprise in an endogenous locus a variant of the nucleic acid construct, e.g., wherein the variant comprises less than n repeats of the hexanucleotide sequence set forth as SEQ ID NO:1 and/or lacks the drug resistance gene, see, e.g., FIGS. 1B and 1C. Accordingly, a variant of a sequence included herein includes sequences essentially identical to the reference parent sequence, but lacking one or more repeats and/or drug resistance gene(s).

"Vector" includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operably linked genes are referred to herein as "expression vectors."

"Wild type" includes an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

Non-human animals are provided having an insertion of a heterologous hexanucleotide repeat expansion sequence in an endogenous C9ORF72 locus. In some embodiments, non-human animals described herein are heterozygous for a modified C9ORF72 locus as described herein. In some embodiments, non-human animals as described herein comprise a first modified C9orf72 locus and a second modified C9orf72 locus, wherein the first and second loci are different. In some embodiments, non-human animals described herein are homozygous for a modified C9ORF72 locus as described herein. In some embodiments, non-human animals described herein develop ALS- and/or FTD-like disease due to the presence of the heterologous hexanucleotide repeat expansion sequence.

Various aspects of the invention are described in detail in the following sections. The use of sections is not meant to limit the invention. Each section can apply to any aspect of the invention. In this application, the use of "or" means "and/or" unless stated otherwise.

C9ORF72

Amyotrophic lateral sclerosis (ALS), also referred to as Lou Gehrig's disease, is the most frequent adult-onset paralytic disorder, characterized by the loss of upper and/or lower motor neurons. ALS occurs in as many as 20,000 individuals across the United States with about 5,000 new cases occurring each year. Frontotemporal dementia (FTD), originally referred to as Pick's disease after physician Arnold Pick, is a group of disorders caused by progressive cell degeneration in the frontal or temporal lobes of the brain. FTD is reported to count for 10-15% of all dementia cases. A hexanucleotide repeat expansion sequence between (and optionally spanning) exons 1a and 1b, two non-coding exons, of the human C9ORF72 gene have been linked to both ALS and FTD (DeJesus-Hernandez, M. et al., 2011, Neuron 72:245-256; Renton, A. E. et al., 2011, Neuron 72:257-268; Majounie, E. et al., 2012, Lancet Neurol. 11:323-330; Waite, A. J. et al., 2014, Neurobiol. Aging 35:1779.e5-1779.e13). It is estimated that the GGGGCC (SEQ ID NO:1) hexanucleotide repeat expansion accounts for about 50% of familial and many non-familial ALS cases. It is present in about 25% of familial FTD cases and about 8% of sporadic.

Many pathological aspects related to the hexanucleotide repeat expansion sequence in C9ORF72 have been reported such as, for example, repeat length-dependent formation of RNA foci, sequestration of specific RNA-binding proteins, and accumulation and aggregation of dipeptide repeat proteins (e.g., reviewed in Stepto, A. et al., 2014, Acta Neuropathol. 127:377-389; see also Almeida, S. et al., 2013, Acta Neuropathol. 126:385-399; Bieniek, K. F. et al., 2014, JAMA Neurol. 71(6): 775-781; van Blitterswijk, M. et al., 2014, Mol. Neurodegen. 9:38, 10 pages). Knock-in mice that have been generated to contain a heterologous hexanucleotide repeat expansion sequence comprising 66 repeats of the hexanucleotide sequence (GGGGCC; SEQ ID NO:1) exhibit RNA foci and dipeptide protein aggregates in their neurons. These mice showed cortical neuron loss and exhibited behavior and motor deficits at 6 months of age (Chew, J. et al., 2015, Science May 14. Pii:aaa9344). However, the mechanism through which such repeat expansions cause disease, whether through a loss- or gain-of-function of toxicity, remains unclear. Additionally, the contribution of a lower number of repeats in the hexanucleotide repeat expansion sequence to ALS/FTD is also unknown.

Although C9ORF72 has been reported to regulate endosomal trafficking (Farg, M. A. et al., 2014, Human Mol. Gen. 23(13): 3579-3595), much of the cellular function of C9ORF72 remains unknown. Indeed, C9ORF72 is a gene that encodes an uncharacterized protein with unknown function. Despite the lack of understanding surrounding C9ORF72, several animal models, including engineered cell lines, for ALS and/or FTD have been developed (Roberson, E. D., 2012, Ann. Neurol. 72(6): 837-849; Panda, S. K. et al., 2013, Genetics 195:703-715; Suzuki, N. et al., 2013, Nature Neurosci. 16(12): 1725-1728; Xu, Z. et al., 2013, Proc. Nat. Acad. Sci. U.S.A. 110(19): 7778-7783; Hukema, R. K. et al., 2014, Acta Neuropath. Comm. 2:166, 4 pages). Another report using a transgenic mouse strain containing a heterologous hexanucleotide repeat expansion sequence comprising 80 GGGGCC repeats operably linked with a fluorescent reporter and controlled by a tetracycline responsive element without any surrounding C9orf72 sequences demonstrated neuronal cytoplasmic inclusions similar to those seen in ALS-FTD patients, which suggests that expanded repeats of the hexanucleotide GGGGCC sequence itself may be responsible for disease (Hukema, R. K. et al., 2014, Acta Neuropathol. Comm. 2: 166, 4 pages). These mice have been useful to establish an initial C9orf72 expression profile in cells of the CNS and provide some understanding of the mechanism of action associated with the repeat expansion; however, construct design can influence the phenotype of the resulting transgenic animal (see, e.g., Muller, U., 1999, Mech. Develop. 81:3-21). For example, a transgenic mouse strain containing an inducible GGGGCC repeat (Hukema, 2014, supra) was designed without human flanking sequence presumably due to the fact that such surrounding sequence was thought to affect translation of repeat sequences. Thus, such in vivo systems exploiting C9ORF72-mediated biology for therapeutic applications are incomplete.

C9ORF72 and Hexanucleotide Repeat Expansion Sequences

Figure 1A:
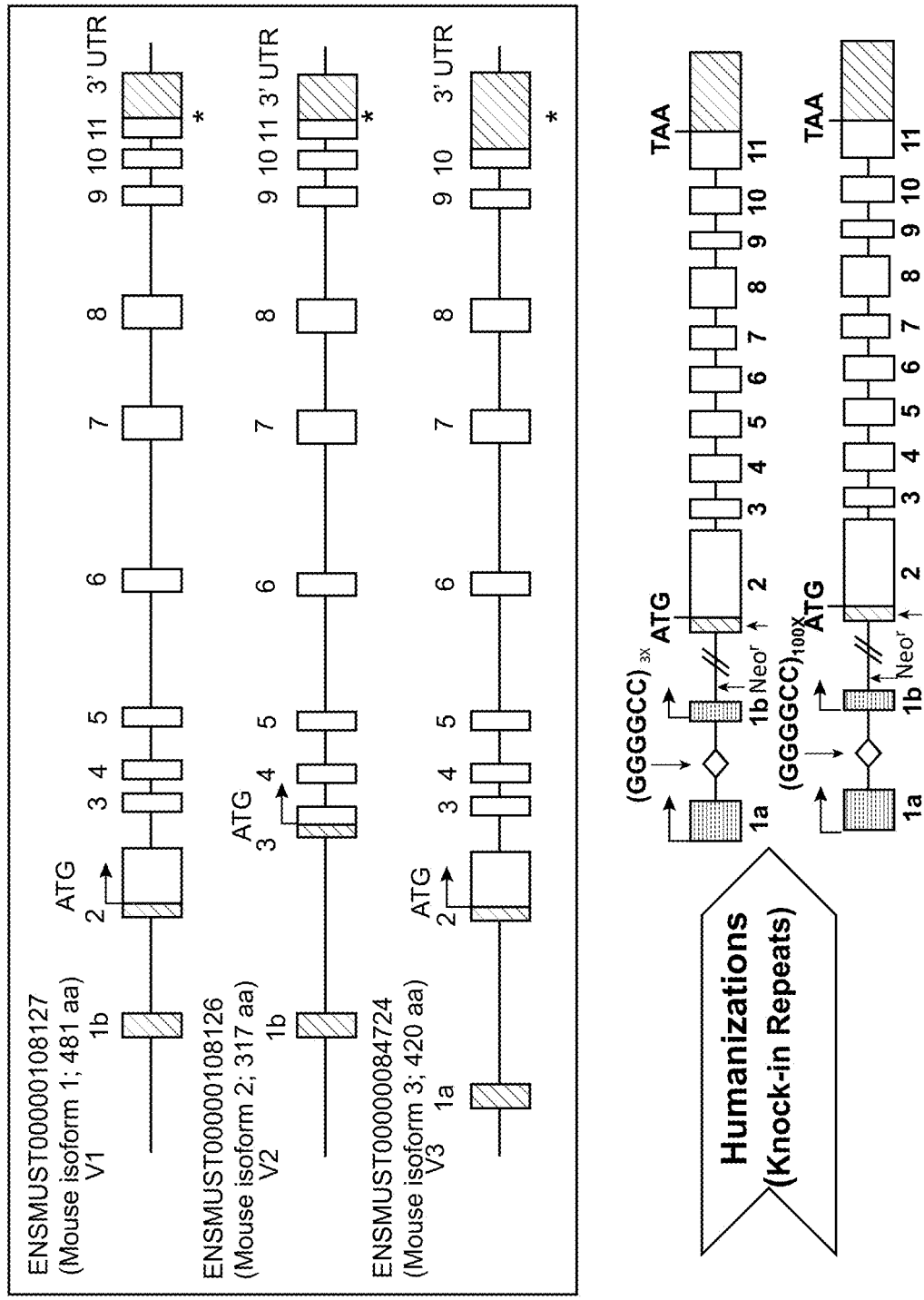
FIG. 1A shows a schematic illustration, not to scale, of the three reported mouse C9orf72 transcript isoforms (V1, V2 and V3) in the top box and a schematic illustration, not to scale, of a targeting strategy for insertion of one of two human heterologous hexanucleotide repeat expansion sequences spanning exons 1a and 1b of the human C9orf72 gene and comprising 3 or 100 repeats into an endogenous mouse C9orf72 locus.

Mouse C9ORF72 transcript variants have been reported in the art (e.g., Koppers et al., Ann Neurol (2015); 78: 426-438; Atkinson et al., Acta Neuropathologica Communications (2015) 3: 59), and are also depicted in FIG. 1A. The genomic information for the three reported mouse C9ORF72 transcript variants is also available at the Ensembl web site under designations of ENSMUST00000108127 (V1), ENSMUST00000108126 (V2), and ENSMUST00000084724 (V3). Exemplary non-human (e.g., rodent) C9ORF72 mRNA and amino acid sequences are set forth in Table 2. For mRNA sequences, bold font contained within parentheses indicates coding sequence and consecutive exons, where indicated, are separated by alternating lower and upper case letters. For amino acid sequences, mature polypeptide sequences, where indicated, are in bold font.

Human C9ORF72 transcript variants are known in the art. One human C9ORF72 transcript variant lacks multiple exons in the central and 3' coding regions, and its 3' terminal exon extends beyond a splice site that is used in variant 3 (see below), which results in a novel 3' untranslated region (UTR) as compared to variant 3. This variant encodes a significantly shorter polypeptide and its C-terminal amino acid is distinct as compared to that which is encoded by two other variants. The mRNA and amino acid sequences of this variant can be found at GenBank accession numbers NM_145005.6 and NP_659442.2, respectively, and are hereby incorporated by reference. The sequences of NM_145005.6 and NP_659442.2 are respectively set forth as SEQ ID NO:10 and SEQ ID NO:11. A second human C9ORF72 transcript variant (2) differs in the 5' untranslated region (UTR) compared to variant 3. The mRNA and amino acid sequences of this variant can be found at GenBank accession numbers NM_018325.4 and NP_060795.1, respectively, and are hereby incorporated by reference. The sequences of NM_018325.4 and NP_060795.1 are respectively set forth as SEQ ID NO:12 and SEQ ID NO:13. A third human C9ORF72 transcript variant (3) contains the longest sequence among three reported variants and encodes the longer isoform. The mRNA and amino acid sequences of this variant can be found at GenBank accession numbers NM_001256054.2 and NP_001242983.1, respectively, and are hereby incorporated by reference. The sequences of NM_001256054.2 and NP_001242983.1 are respectively set forth as SEQ ID NO:14 and SEQ ID NO:15. Variants 2 and 3 encode the same protein.

A hexanucleotide repeat expansion sequence is generally a nucleotide sequence comprising at least one instance, e.g., one repeat, of the hexanucleotide sequence GGGGCC set forth as SEQ ID NO:1. For purposes of insertion into an endogenous non-human C9orf72 locus, a heterologous hexanucleotide repeat expansion sequence comprises at least one instance (repeat) and preferably more than one instance (repeat) of the hexanucleotide sequence set forth as SEQ ID NO:1 and may be identical to, or substantially identical to a genomic nucleic acid sequence spanning (and optionally including) non-coding exons 1a and 1b of a human 'chromosome 9 open reading frame 72' (C9orf72), or a portion thereof. Non-limiting examples of heterologous hexanucleotide expansion sequences include the sequences set forth as SEQ ID NO:1, SEQ ID NO:2 (comprising three repeats of the GGGGCC hexanucleotide sequence) and SEQ ID NO:3 (comprising 100 repeats of the GGGGCC hexanucleotide sequence).

TABLE 2

Mus musculus C9orf72 mRNA
(NM_001081343; SEQ ID NO: 16)
gtgtccggggcggggcggtcccggggcggggcccggagcgggctgcggtt gcggtccctgcgccggcggtgaaggcgcagcagcggcgagtggCTATTGC

AAGCGTTCGGATAATGTGAGACCTGGAATGCAGTGAGACCTGGGATGCAG

GG(ATGTCGACTATCTGCCCCCCACCATCTCCTGCTGTTGCCAAGACAGA

GATTGCTTTAAGTGGTGAATCACCCTTGTTGGCGGCTACCTTTGCTTACT

GGGATAATATTCTTGGTCCTAGAGTAAGGCATATTTGGGCTCCAAAGACA

GACCAAGTGCTTCTCAGTGATGGAGAAATAACTTTTCTTGCCAACCACAC

TCTAAATGGAGAAATTCTTCGAAATGCAGAGAGTGGGGCTATAGATGTAA

AATTTTTTGTCTTATCTGAAAAAGGGGTAATTATTGTTTCATTAATCTTC

GACGGAAACTGGAATGGAGATCGGAGCACTTATGGACTATCAATTATACT

GCCGCAGACAGAGCTGAGCTTCTACCTCCCACTTCACAGAGTGTGTGTTG

ACAGGCTAACACACATTATTCGAAAAGGAAGAATATGGATGCATAAGgaa agacaagaaaatgtccagaaaattgtcttggaaggcacagagaggatgga agatcagGGTCAGAGTATCATTCCCATGCTTACTGGGGAAGTCATTCCTG

TAATGGAGCTGCTTGCATCTATGAAATCCCACAGTGTTCCTGAAGACATT

GATatagctgatacagtgctcaatgatgatgacattggtgacagctgtca cgaaggctttcttctcaaTGCCATCAGCTCACACCTGCAGACCTGTGGCT GTTCCGTTGTAGTTGGCAGCAGTGCAGAGAAAGTAAATAAGatagtaaga acgctgtgccttttctgacaccagcagagaggaaatgctccaggctgtg tgaagcagaatcgtcctttaagtacgaatcgggactctttgtgcaaggct tgctaaagGATGCAACAGGCAGTTTTGTCCTACCCTTCCGGCAAGTTATG

TATGCCCCGTACCCCACCACGCACATTGATGTGGATGTCAACACTGTCAA

GCAGATGCCACCGTGTCATGAACATATTTATAATCAACGCAGATACATGA

GGTCAGAGCTGACAGCCTTCTGGAGGGCAACTTCAGAAGAGGACATGGCG

CAGGACACCATCATCTACACAGATGAGAGCTTCACTCCTGATTTgaatat

TABLE 2-continued tttccaagatgtcttacacagagacactctagtgaaagccttcctggatc
agGTCTTCCATTTGAAGCCTGGCCTGTCTCTCAGGAGTACTTTCCTTGCA
CAGTTCCTCCTCATTCTTCACAGAAAAGCCTTGACACTAATCAAGTACAT
CGAGGATGATACgcagaagggaaaaagccctttaagtctcttcggaacc
tgaagatagatcttgatttaacagcagagggcgatcttaacataataatg
gctctagctgagaaaattaagccaggcctacactctttcatctttgggag
acctttctacactagtgtacaagaacgtgatgttctaatgacctttga)
ccgtgtggtttgctgtgtctgtctcttcacagtcacacctgctgttacag
tgtctcagcagtgtgtgggcacatccttcctcccgagtcctgctgcagga
cagggtacactacacttgtcagtagaagtctgtacctgatgtcaggtgca
tcgttacagtgaatgactcttcctagaatagatgtactcttttagggcct
tatgtttacaattatcctaagtactattgctgtctttaaagatatgaat
gatgaatatacacttgaccataactgctgattggtttttgttttgttt
tgtttgttttcttggaaacttatgattcctggtttacatgtaccacactg
aaaccctcgttagctttacagataaagtgtgagttgacttcctgcccctc
tgtgttctggtatgtccgattacttctgccacagctaaacattagagc
atttaaagtttgcagttcctcagaaaggaacttagtctgactacagatta
gttcttgagagaagacactgatagggcagagctgtaggtgaaatcagttg
ttagcccttcctttatagacgtagtccttcagattcggtctgtacagaaa
tgccgaggggtcatgcatgggccctgagtatcgtgacctgtgacaagttt
tttgttggtttattgtagttctgtcaaagaaagtggcatttgttttttata
attgttgccaacttttaaggttaattttcattattttttgagccgaattaa
aatgcgcacctcctgtgcctttcccaatcttggaaaatataatttcttgg
cagagggtcagatttcagggcccagtcactttcatctgaccacccttgc
acggctgccgtgtgcctggcttagattagaagtccttgttaagtatgtca
gagtacattcgctgataagatcttttgaagagcagggaagcgtcttgcctc
tttcctttggtttctgcctgtactctggtgtttccgtgtcacctgcatc
ataggaacagcagagaaatctgacccagtgctatttttctaggtgctact
atggcaaactcaagtggtctgtttctgttcctgtaacgttcgactatctc
gctagctgtgaagtactgattagtggagttctgtgcaacagcagtgtagg
agtatacacaaacacaaatgtgtttctatttaaaactgtggacttagc
ataaaaaggagaatatatttatttttacaaaagggataaaaatgggcc
ccgttcctcacccaccagatttagcgagaaaaagctttctattctgaaag
gtcacggtggctttggcattacaaatcagaacaacacacactgaccatga
tggcttgtgaactaactgcaaggcactccgtcatggtaagcgagtaggtc
ccacctcctagtgtgccgctcattgctttacacagtagaatcttatttga
gtgctaattgttgtctttgctgctttactgtgttgttatagaaatgaa
gctgtacagtgaataagttattgaagcatgtgtaaacactgttatatatc
ttttctcctagatggggaattttgaataaaatacctttgaaattctgtgt

*Mus musculus* C9orf72 amino acid
(NP_001074812; SEQ ID NO: 17)
MSTICPPPSPAVAKTEIALSGESPLLAATFAYWDNILGPRVRHIWAPKTD
QVLLSDGEITFLANHTLNGEILRNAESGAIDVKFFVLSEKGVIIVSLIFD
GNWNGDRSTYGLSIILPQTELSFYLPLHRVCVDRLTHIIRKGRIWMHKER
QENVQKIVLEGTERMEDQGQSIIPMLTGEVIPVMELLASMKSHSVPEDID
IADTVLNDDDIGDSCHEGFLLNAISSHLQTCGCSVVVGSSAEKVNKIVRT
LCLFLTPAERKCSRLCEAESSFKYESGLFVQGLLKDATGSFVLPFRQVMY
APYPTTHIDVDVNTVKQMPPCHEHIYNQRRYMRSELTAFWRATSEEDMAQ
DTIIYTDESFTPDLNIFQDVLHRDTLVKAFLDQVFHLKPGLSLRSTFLAQ
FLLILHRKALTLIKYIEDDTQKGKKPFKSLRNLKIDLDLTAEGDLNIIMA
LAEKIKPGLHSFIFGRPFYTSVQERDVLMTF

*Rattus norvegicus* C9orf72 mRNA
(NM_001007702; SEQ ID NO: 18)
CGTTTGTAGTGTCAGCCATCCCAATTGCCTGTTCCTTCTCTGTGGGAGTG
GTGTCTAGACAGTCCAGGCAGGGTATGCTAGGCAGGTGCGTTTTGGTTGC
CTCAGATCGCAACTTGACTCCATAACGGTGACCAAAGACAAAAGAAGGAA
ACCAGATTAAAAAGAACCGGACACAGACCCCTGCAGAATCTGGAGCGGCC
GTGGTTGGGGCGGGGCTACGACGGGGCGGACTCGGGGGCGTGGGAGGGC
GGGGCCGGGGCGGGGCCCGGAGCCGGCTGCGGTTGCGGTCCCTGCGCCGG
CGGTGAAGGCGCAGCGGCGGCGAGTGGCTATTGCAAGCGTTTGGATAATG
TGAGACCTGGGATGCAGGG(ATGTCGACTATCTGCCCCCCACCATCTCCT
GCTGTTGCCAAGACAGAGATTGCTTTAAGTGGTGAATCACCCTTGTTGGC
GGCTACCTTTGCTTACTGGGATAATATTCTTGGTCCTAGAGTAAGGCACA
TTTGGGCTCCAAAGACAGACCAAGTACTCCTCAGTGATGGAGAAATCACT
TTTCTTGCCAACCACACTCTGAATGGAGAAATTCTTCGGAATGCGGAGAG
TGGGGCAATAGATGTAAAGTTTTTTGTCTTATCTGAAAAGGGCGTCATTA
TTGTTTCATTAATCTTCGACGGGAACTGGAACGGAGATCGGAGCACTTAC
GGACTATCAATTATACTGCCGCAGACGGAGCTGAGTTTCTACCTCCCACT
GCACAGAGTGTGTGTTGACAGGCTAACGCACATCATTCGAAAAGGAAGGA
TATGGATGCACAAGGAAAGACAAGAAAATGTCCAGAAAATTGTCTTGGAA
GGCACCGAGAGGATGGAAGATCAGGGTCAGAGTATCATCCCTATGCTTAC
TGGGGAGGTCATCCCTGTGATGGAGCTGCTTGCGTCTATGAGATCACACA
GTGTTCCTGAAGACCTCGATATAGCTGATACAGTACTCAATGATGATGAC
ATTGGTGACAGCTGTCATGAAGGCTTTCTTCTCAATGCCATCAGCTCACA
TCTGCAGACCTGCGGCTGTTCTGTGGTGGTAGGCAGCAGTGCAGAGAAAG
TAAATAAGATAGTAAGAACACTGTGCCTTTTTCTGACACCAGCAGAGAGG
AAGTGCTCCAGGCTGTGTGAAGCCGAATCGTCCTTTAAATACGAATCTGG
ACTCTTTGTACAAGGCTTGCTAAAGGATGCGACTGGCAGTTTTGTACTAC
CTTTCCGGCAAGTTATGTATGCCCCTTATCCCACCACACACATCGATGTG
GATGTCAACACTGTCAAGCAGATGCCACCGTGTCATGAACATATTTATAA
TCAACGCAGATACATGAGGTCAGAGCTGACAGCCTTCTGGAGGGCAACTT
CAGAAGAGGACATGGCTCAGGACACCATCATCTACACAGATGAGAGCTTC TABLE 2-continued

ACTCCTGATTTGAATATTTTCCAAGATGTCTTACACAGAGACACTCTAGT

GAAAGCCTTTCTGGATCAGGTCTTCCATTTGAAGCCTGGCCTGTCTCTCA

GGAGTACTTTCCTTGCACAGTTCCTCCTCATTCTTCACAGAAAAGCCTTG

ACACTAATCAAGTACATAGAGGATGACACGCAGAAGGGGAAAAAGCCCTT

TAAGTCTCTTCGGAACCTGAAGATAGATCTTGATTTAACAGCAGAGGGCG

ACCTTAACATAATAATGGCTCTAGCTGAGAAAATTAAGCCAGGCCTACAC

TCTTTCATCTTCGGGAGACCTTTCTACACTAGTGTCCAAGAACGTGATGT

TCTAATGACTTTTTAA)ACATGTGGTTTGCTCCGTGTGTCTCATGACAGT

CACACTTGCTGTTACAGTGTCTCAGCGCTTTGGACACATCCTTCCTCCAG

GGTCCTGCCGCAGGACACGTTACACTACACTTGTCAGTAGAGGTCTGTAC

CAGATGTCAGGTACATCGTTGTAGTGAATGTCTCTTTTCCTAGACTAGAT

GTACCCTCGTAGGGACTTATGTTTACAACCCTCCTAAGTACTAGTGCTGT

CTTGTAAGGATACGAATGAAGGGATGTAAACTTCACCACAACTGCTGGTT

GGTTTTGTTGTTTTTGTTTTTTGAAACTTATAATTCATGGTTTACATGCA

TCACACTGAAACCCTAGTTAGCTTTTTACAGGTAAGCTGTGAGTTGACTG

CCTGTCCCTGTGTTCTCTGGCCTGTACGATCTGTGGCGTGTAGGATCACT

TTTGCAACAACTAAAAACTAAAGCACTTTGTTTGCAGTTCTACAGAAAGC

AACTTAGTCTGTCTGCAGATTCGTTTTTGAAAGAAGACATGAGAAAGCGG

AGTTTTAGGTGAAGTCAGTTGTTGGATCTTCCTTTATAGACTTAGTCCTT

TAGATGTGGTCTGTATAGACATGCCCAACCATCATGCATGGGCACTGAAT

ATCGTGAACTGTGGTATGCTTTTTGTTGGTTTATTGTACTTCTGTCAAAG

AAAGTGGCATTGGTTTTTATAATTGTTGCCAAGTTTTAAGGTTAATTTTC

ATTATTTTTGAGCCAAATTAAAATGTGCACCTCCTGTGCCTTTCCCAATC

TTGGAAAATATAATTTCTTGGCAGAAGGTCAGATTTCAGGGCCCAGTCAC

TTTCGTCTGACTTCCCTTTGCACAGTCCGCCATGGGCCTGGCTTAGAAGT

TCTTGTAAACTATGCCAGAGAGTACATTCGCTGATAAAATCTTCTTTGCA

GAGCAGGAGAGCTTCTTGCCTCTTTCCTTTCATTTCTGCCTGGACTTTGG

TGTTCTCCACGTTCCCTGCATCCTAAGGACAGCAGGAGAACTCTGACCCC

AGTGCTATTTCTCTAGGTGCTATTGTGGCAAACTCAAGCGGTCCGTCTCT

GTCCCTGTAACGTTCGTACCTTGCTGGCTGTGAAGTACTGACTGGTAAAG

CTCCGTGCTACAGCAGTGTAGGGTATACACAAACACAAGTAAGTGTTTTA

TTTAAAACTGTGGACTTAGCATAAAAAGGGAGACTATATTTATTTTTTAC

AAAAGGGATAAAAATGGAACCCTTTCCTCACCCACCAGATTTAGTCAGAA

AAAAACATTCTATTCTGAAAGGTCACAGTGGTTTTGACATGACACATCAG

AACAACGCACACTGTCCATGATGGCTTATGAACTCCAAGTCACTCCATCA

TGGTAAATGGGTAGATCCCTCCTTCTAGTGTGCCACACCATTGCTTCCCA

CAGTAGAATCTTATTTAAGTGCTAAGTGTTGTCTCTGCTGGTTTACTCTG

TTGTTTTAGAGAATGTAAGTTGTATAGTGAATAAGTTATTGAAGCATGTG

TAAACACTGTTATACATCTTTTCTCCTAGATGGGAATTTGGAATAAAAT

ACCTTTAAAATTCAAAAAAAAAAAAAAAAAAAAAAA

TABLE 2-continued

Rattus norvegicus C9orf72 amino acid
(NP_001007703; SEQ ID NO: 19)
MSTICPPPSPAVAKTEIALSGESPLLAATFAYWDNILGPRVRHIWAPKTD

QVLLSDGEITFLANHTLNGEILRNAESGAIDVKFFVLSEKGVIIVSLIFD

GNWNGDRSTYGLSIILPQTELSFYLPLHRVCVDRLTHIIRKGRIWMHKER

QENVQKIVLEGTERMEDQGQSIIPMLTGEVIPVMELLASMRSHSVPEDLD

IADTVLNDDDIGDSCHEGFLLNAISSHLQTCGCSVVVGSSAEKVNKIVRT

LCLFLTPAERKCSRLCEAESSFKYESGLFVQGLLKDATGSFVLPFRQVMY

APYPTTHIDVDVNTVKQMPPCHEHIYNQRRYMRSELTAFWRATSEEDMAQ

DTIIYTDESFTPDLNIFQDVLHRDTLVKAFLDQVFHLKPGLSLRSTFLAQ

FLLILHRKALTLIKYIEDDTQKGKKPFKSLRNLKIDLDLTAEGDLNIIMA

LAEKIKPGLHSFIFGRPFYTSVQERDVLMTF

C9ORF72 Targeting Vectors and Production of Non-Human Animals Having a Heterologous Hexanucleotide Repeat Expansion Sequence Inserted in a C9ORF72 Locus Provided herein are targeting vectors or targeting constructs for the production of non-human animals having a heterologous hexanucleotide expansion sequence inserted into an endogenous C9ORF72 locus as described herein.

A. Large Targeting Vectors

In cells other than one-cell stage embryos, a targeting vector that is a "large targeting vector" or "LTVEC" can be used, which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to a locus of the cell that is not targetable using a conventional method or that can be targeted only incorrectly or only with significantly low efficiency in the absence of a nick or double-strand break induced by a nuclease agent (e.g., a Cas protein).

A targeting vector includes homology arms. If the targeting vector also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the genomic region of interest, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. A corresponding region of homology between the homology arm and the corresponding target sequence can be of any length that is sufficient to promote homologous recombination. The homology arms can be symmetrical (each about the same size in length), or they can be asymmetrical (one longer than the other).

The homology arms can correspond to a locus that is native to a cell (e.g., the targeted locus). Alternatively, for example, they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; and 7,105,348; and in WO 2002/036789, each of which is herein incorporated by reference in its entirety for all purposes. LTVECs can be in linear form or in circular form.

LTVECs can be of any length and are typically at least 10 kb in length. For example, an LTVEC can be from about 50 kb to about 500 kb, from about 50 kb to about 75 kb, from about 75 kb to about 100 kb, from about 100 kb to about 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb, from about 275 kb to about 300 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR.

The sum total of the 5' homology arm and the 3' homology arm in an LTVEC is typically at least 10 kb. As an example, the 5' homology arm can range from about 5 kb to about 150 kb and/or the 3' homology arm can range from about 5 kb to about 150 kb. Each homology arm can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can be, for example, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, or from about 350 kb to about 400 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, or at least 400 kb.

LTVECs can comprise nucleic acid inserts having nucleic acid sequences larger than those typically used by other approaches intended to perform homologous recombination in cells. For example, an LTVEC can comprise a nucleic acid insert ranging from about 1 kb to about 5 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 450 kb, from about 450 kb to about 500 kb, or greater. Alternatively, the nucleic acid insert can be at least 1 kb, at least 5 kb, at least 10 kb, at least 20 kb, at least 30 kb, at least 40 kb, at least 60 kb, at least 80 kb, at least 100 kb, at least 150 kb, at least 200 kb, at least 250 kb, at least 300 kb, at least 350 kb, at least 400 kb, at least 450 kb, or at least 500 kb.

B. Construction of Large Targeting Vectors

Many of the techniques used to construct targeting vectors described herein are standard molecular biology techniques well known to the skilled artisan (see, e.g., Sambrook, J., E. F. Fritsch and T. Maniatis. Molecular Cloning: A Laboratory Manual, Second Edition, Vols. 1, 2, and 3, 1989; Current Protocols in, Molecular Biology, Eds. Ausubel et al., Greene Publ. Assoc., Wiley Interscience, NY). Any methods known in the art for constructing large targeting vectors can be used.

In one example, the method for constructing a large targeting vector (LTVEC) comprises: (a) obtaining a large genomic DNA clone containing the gene/genes or chromosomal locus/loci of interest; and (b) appending homology boxes 1 and 2 to a modification cassette to generate the LTVEC. Optionally, such methods can further comprise verifying that each LTVEC has been engineered correctly. Optionally, such methods can further comprise purification, preparation, and linearization of LTVEC DNA for introduction into eukaryotic cells. Such methods are further described in US 2004/0018626, US 2013/0309670, and WO 2013/163394, each of which is herein incorporated by reference in its entirety for all purposes.

Genes or loci of interest can be selected based on specific criteria, such as detailed structural or functional data, or they can be selected in the absence of such detailed information as potential genes or gene fragments become predicted through the efforts of the various genome sequencing projects. It is not necessary to know the complete sequence and gene structure of a gene or locus of interest to produce LTVECs. The only sequence information that is required is approximately 80-100 nucleotides so as to obtain the genomic clone of interest as well as to generate the homology boxes used in making the LTVEC and to make probes for use in quantitative modification-of-allele (MOA) assays.

Once a gene or locus of interest has been selected, a large genomic clone containing this gene or locus can be obtained. This clone can be obtained in any one of several ways including, but not limited to, screening suitable DNA libraries (e.g., BAC, PAC, YAC, or cosmid) by standard hybridization or PCR techniques, or by any other methods familiar to the skilled artisan.

Homology boxes mark the sites of bacterial homologous recombination that are used to generate LTVECs from large cloned genomic fragments. Homology boxes are short segments of DNA, generally double-stranded and at least 40 nucleotides in length, that are homologous to regions within the large cloned genomic fragment flanking the region to be modified. The homology boxes are appended to the modification cassette so that following homologous recombination in bacteria, the modification cassette replaces the region to be modified. The technique of creating a targeting vector using bacterial homologous recombination can be performed in a variety of systems (see, e.g., Yang et al. (1997) *Nat. Biotechnol.* 15:859-865, Muyrers et al. (1999) *Nucleic Acids Res.* 27:1555-1557; Angrand et al. (1999) *Nucleic Acids Res.* 27:e16; Narayanan et al. (1999) *Gene Ther.* 6:442-447; Yu, et al. (2000) *Proc. Natl. Acad. Sci. U.S.A.* 97:5978-5983, each of which is herein incorporated by reference in its entirety for all purposes). One example of such a technology is ET cloning (see, e.g., Zhang et al. (1998) *Nat. Genet.* 20:123-128; Narayanan et al. (1999) *Gene Ther.* 6: 442-447, each of which is herein incorporated by reference in its entirety for all purposes) and variations of this technology (see, e.g., Yu et al. (2000) *Proc. Natl. Acad. Sci. U.S.A.* 97:5978-5983, herein incorporated by reference in its entirety for all purposes). ET refers to the recE and recT proteins that carry out the homologous recombination reaction. RecE is an exonuclease that trims one strand of linear double-stranded DNA 5' to 3', thus leaving behind a linear double-stranded fragment with a 3' single-stranded overhang. This single-stranded overhang is coated by recT protein, which has single-stranded DNA (ssDNA) binding activity. ET cloning is performed using *E. coli* that transiently express the *E. coli* gene products of recE and recT and the bacteriophage lambda (λ) protein λgam. The λgam protein is protects the donor DNA fragment from degradation by the recBC exonuclease system and it is preferred for efficient ET cloning in recBC+ hosts such as the frequently used *E. coli* strain DH10b.

LTVECs can also be generated by DNA assembly methods, such as in vitro DNA assembly methods including Gibson DNA assembly or modifications of Gibson DNA assembly. See, e.g., US 2015/0376628, US 2016/0115486, WO 2015/200334, and US 2010/0035768, each of which is incorporated by reference in its entirety for all purposes.

Traditional methods of assembling nucleic acids employ time consuming steps of conventional enzymatic digestion with restriction enzymes, cloning of the nucleic acids, and ligating nucleic acids together. These methods are made more difficult when large fragments or vectors are being assembled together. However, the malleable target specificity of nucleases (e.g., guide RNAs and Cas9 nucleases) can be taken advantage of to convert nucleic acids into a form suitable for use in rapid assembly reactions. See, e.g., US 2015/0376628, US 2016/0115486, and WO 2015/200334, each of which is incorporated by reference in its entirety for all purposes.

Any DNA molecules of interest having overlapping sequences can be assembled by such methods, including DNAs which are naturally occurring, cloned DNA molecules, synthetically generated DNAs, and so forth. Assembling two nucleic acids includes any method of joining strands of two nucleic acids. For example, assembly includes joining digested nucleic acids such that strands from each nucleic acid anneal to the other and extension, in which each strand serves as a template for extension of the other.

Any in vitro or in vivo DNA assembly methods or rapid combinatorial methods can be used to assemble the nucleic acids. For example, a first and a second nucleic acid having overlapping ends can be combined with a ligase, exonuclease, DNA polymerase, and nucleotides and incubated at a constant temperature, such as at 50° C. Specifically, a T5 exonuclease could be used to remove nucleotides from the 5' ends of dsDNA producing complementary overhangs. The complementary single-stranded DNA overhangs can then be annealed, DNA polymerase used for gap filling, and Taq DNA ligase used to seal the resulting nicks at 50° C. Thus, two nucleic acids sharing overlapping end sequences can be joined into a covalently sealed molecule in a one-step isothermal reaction. See, e.g., Gibson et al. (2009) *Nature Methods* 6(5): 343-345, herein incorporated by reference in its entirety for all purposes.

Site-directed nuclease agents (e.g., guide RNA-directed Cas proteins) allow rapid and efficient combination of nucleic acids by selecting and manipulating the end sequences generated by their endonuclease activity. For example, DNA assembly methods can combine a first polynucleotide with a nuclease agent (e.g., a gRNA-Cas complex) specific for a desired target site and an exonuclease. The target site can be chosen such that when the nuclease cleaves the nucleic acid, the resulting ends created by the cleavage have regions complementary to the ends of a second nucleic acid to be assembled with the first nucleic acid (e.g., overlapping ends). These complementary ends can then be assembled to yield a single assembled nucleic acid. Because the nuclease agent (e.g., gRNA-Cas complex) is specific for an individual target site, the method allows for modification of nucleic acids in a precise site-directed manner. By selecting a nuclease agent (e.g., a gRNA-Cas complex) specific for a target site such that, on cleavage, produces end sequences complementary to those of a second nucleic acid, isothermal assembly can be used to assemble the resulting digested nucleic acid. Thus, by selecting nucleic acids and nuclease agents (e.g., gRNA-Cas complexes) that result in overlapping end sequences, nucleic acids can be assembled by rapid combinatorial methods to produce the final assembled nucleic acid in a fast and efficient manner. Alternatively, nucleic acids not having complementary ends can be assembled with joiner oligos designed to have complementary ends to each nucleic acid. By using the joiner oligos, two or more nucleic acids can be seamlessly assembled, thereby reducing unnecessary sequences in the resulting assembled nucleic acid.

Verification that the LTVEC has been engineered correctly can then be undertaken. For example, diagnostic PCR can be used to verify the novel junctions created by the introduction of the donor fragment into the gene or chromosomal locus of interest. Alternatively or additionally, diagnostic restriction enzyme digestion can be done to make sure that only the desired modifications have been introduced into the LTVEC during the bacterial homologous recombination process. Alternatively or additionally, direct sequencing of the LTVEC can be done, particularly the regions spanning the site of the modification to verify the novel junctions created by the introduction of the donor fragment into the gene or chromosomal locus of interest.

After any purification and further preparation of the LTVEC DNA for introduction into eukaryotic cells, the LTVEC is preferably linearized in a manner that leaves the modified endogenous gene or chromosomal locus DNA flanked with long homology arms. This can be accomplished by linearizing the LTVEC, preferably in the vector backbone, with any suitable restriction enzyme that digests only rarely. Examples of suitable restriction enzymes include NotI, PacI, SfiI, SrfI, SwaI, FseI, and so forth. The choice of restriction enzyme may be determined experimentally (i.e., by testing several different candidate rare cutters) or, if the sequence of the LTVEC is known, by analyzing the sequence and choosing a suitable restriction enzyme based on the analysis.

C. C9orf72-HRE Nucleic Acid Constructs

DNA sequences can be used to prepare LTVECs for knock-in animals (e.g., an C9ORF72-HRE). Typically, a polynucleotide molecule (e.g., an insert nucleic acid) comprising a hexanucleotide expansion sequence and/or a selectable marker is inserted into a vector, preferably a DNA vector, in order to replicate the polynucleotide molecule in a suitable host cell.

A polynucleotide molecule (or insert nucleic acid) comprises a segment of DNA that one desires to integrate into a target locus. In some embodiments, an insert nucleic acid comprises one or more polynucleotides of interest. In some embodiments, an insert nucleic acid comprises one or more expression cassettes. In some certain embodiments, an expression cassette comprises a polynucleotide of interest, a polynucleotide encoding a selection marker and/or a reporter gene along with, in some certain embodiments, various regulatory components that influence expression. Virtually any polynucleotide of interest may be contained within an insert nucleic acid and thereby integrated at a target genomic locus. Methods disclosed herein, provide for at least 1, 2, 3, 4, 5, 6 or more polynucleotides of interest to be integrated into a targeted C9ORF72 genomic locus.

In some embodiments, a polynucleotide of interest contained in an insert nucleic acid encodes a reporter. In some embodiments, a polynucleotide of interest encodes a selectable marker.

In some embodiments, a polynucleotide of interest is flanked by or comprises site-specific recombination sites (e.g., loxP, Frt, etc.). In some certain embodiments, site-specific recombination sites flank a DNA segment that encodes a reporter and/or a DNA segment that encodes a selectable marker. Exemplary polynucleotides of interest, including selection markers and reporter genes that can be included within insert nucleic acids are described herein.

Various methods employed in preparation of plasmids, DNA constructs and/or targeting vectors and transformation of host organisms are known in the art. For other suitable expression systems for both prokaryotic and eukaryotic cells, as well as general recombinant procedures, see Molecular Cloning: A Laboratory Manual, 2nd Ed., ed. by Sambrook, J. et al., Cold Spring Harbor Laboratory Press: 1989.

As described above, exemplary non-human (e.g., rodent) C9ORF72 nucleic acid and amino acid sequences for use in constructing targeting vectors for knock-in animals are provided in Table 2. Other non-human C9ORF72 sequences can also be found in the GenBank database. C9ORF72 targeting vectors as disclosed herein comprise a heterologous hexanucleotide repeat expansion sequence, and optionally one or more sequences encoding a reporter gene and/or a selectable marker, flanked by sequences that are identical or substantially homologous to flanking sequences of a target region (also referred to as "homology arms") for insertion into the genome of a transgenic non-human animal.

To give but one example, an insertion start point may be set upstream (5'), within, or downstream (3') of a first exon, e.g., a first non-coding exon, to allow an insert nucleic acid to be operably linked to an endogenous regulatory sequence (e.g., a promoter). A targeting strategy for making a targeted insertion of a heterologous hexanucleotide repeat expansion sequence is provided in FIG. 1B and FIG. 1C. The drug selection cassette is flanked by loxP (LP) recombinase recognition sites that enable Cre-mediated excision of the drug selection cassette. This allows for, among other things, excision of the selection cassette. Thus, prior to phenotypic analysis the drug selection cassette may be removed leaving only the heterologous hexanucleotide repeat expansion sequence, and in some embodiments, one copy of the recombinase recognition site.

Figure 1B:
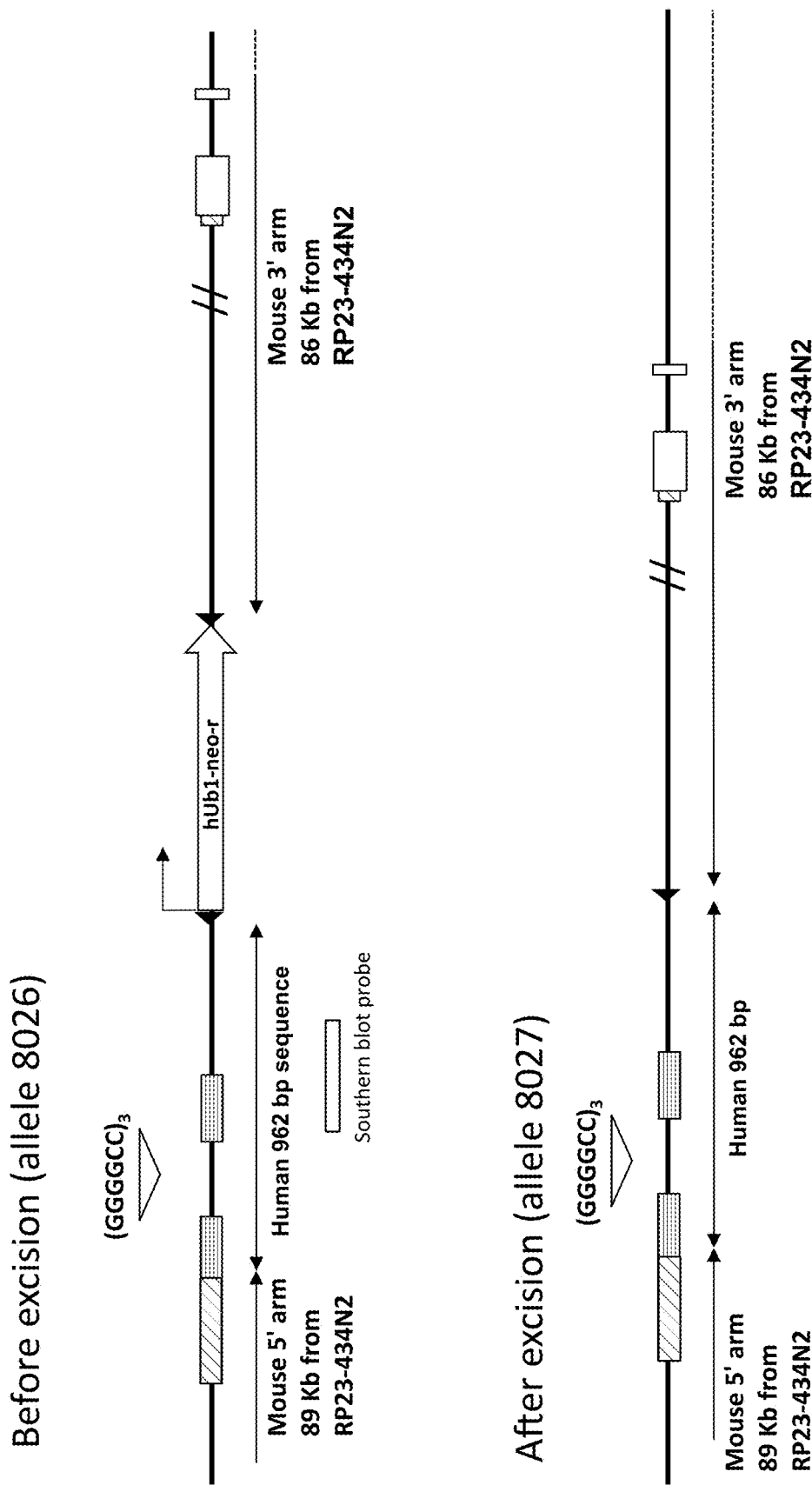
In FIGS. 1B and 1C, murine non-coding regions are represented by diagonally striped boxes, human non-coding exons are represented by horizontally striped boxes, and mouse coding exons are represented by white boxes. Also shown in the top panels of FIGS. 1B and 1C is an approximate location of a probe (vertical white rectangle) used for Southern blot analysis (SEQ ID NO:29).
Figure 1C:
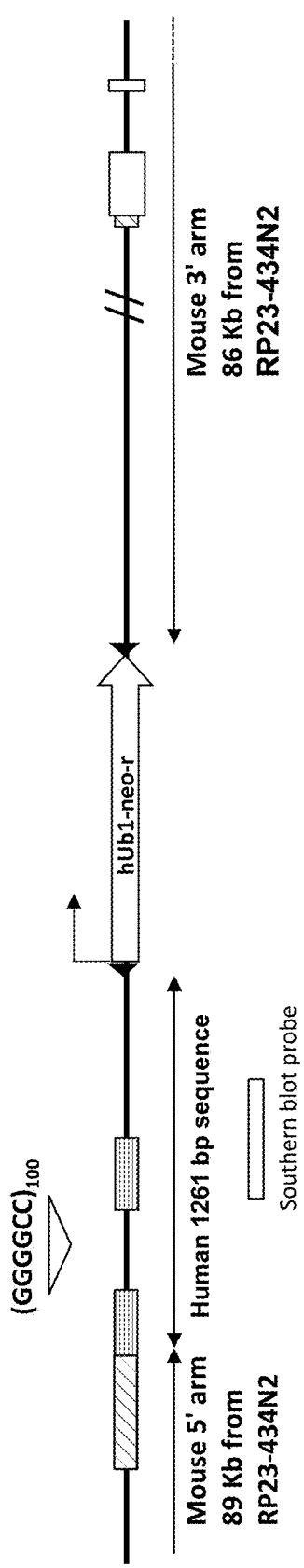
Figure 1C:
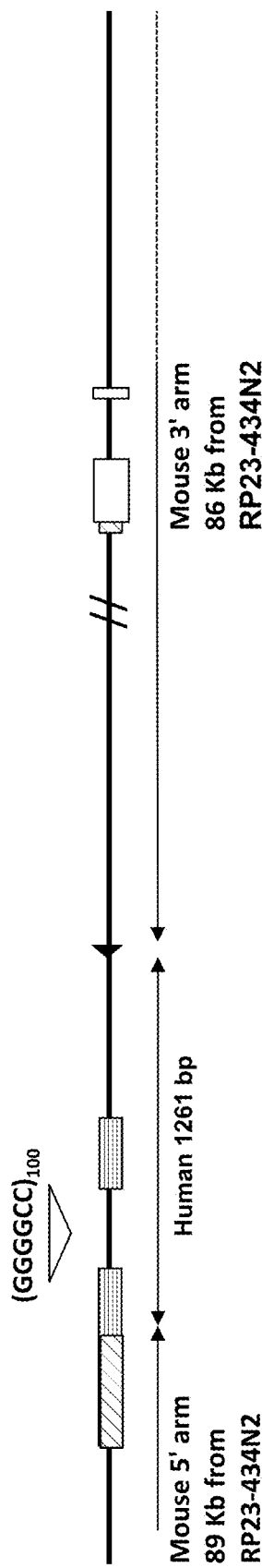

Disclosed herein are nucleic acid constructs useful for the modified mouse C9orf72 alleles depicted in FIGS. 1B and 1C, wherein the nucleic acid constructs comprise the sequences set forth in SEQ ID NO:8 and SEQ ID NO:9. SEQ ID NO:8 comprises from 5' to 3': a 5' homology arm (SEQ ID NO:20), a 962 human bp sequence spanning and including part of exon 1a and all of exon 1b of a human C9orf72 gene (SEQ ID NO:2), a floxed neomycin resistance cassette containing the neomycin resistance gene under the control of a human ubiquitin 1 and/or Em7 promoter (SEQ ID NO:21), and a 3' homology arm (SEQ ID NO:22). SEQ ID NO:9 comprises from 5' to 3': a 5' homology arm (SEQ ID NO:23), a 1261 human bp sequence spanning and including part exon 1a and all of exon 1b of a human C9orf72 gene (SEQ ID NO:3), a floxed neomycin resistance cassette containing the neomycin resistance gene under the control of a human ubiquitin 1 and/or Em7 promoter (SEQ ID NO:24), and a 3' homology arm (SEQ ID NO:25).

As described herein, insertion of heterologous hexanucleotide repeat expansion sequence into an endogenous C9orf72 locus can comprise a replacement of or an insertion/addition to the C9orf72 locus or a portion thereof with an insert nucleic acid. In some embodiments, an insert nucleic acid comprises a reporter gene. In some certain embodiments, a reporter gene is positioned in operable linkage with an endogenous C9orf72 promoter. Such a modification allows for the expression of a reporter gene driven by an endogenous C9orf72 promoter. Alternatively, a reporter gene is not placed in operable linkage with an endogenous C9orf72 promoter.

A variety of reporter genes (or detectable moieties) can be used in targeting vectors described herein. Exemplary reporter genes include, for example, β-galactosidase (encoded lacZ gene), Green Fluorescent Protein (GFP), enhanced Green Fluorescent Protein (eGFP), MmGFP, blue fluorescent protein (BFP), enhanced blue fluorescent protein (eBFP), mPlum, mCherry, tdTomato, mStrawberry, J-Red, DsRed, mOrange, mKO, mCitrine, Venus, YPet, yellow fluorescent protein (YFP), enhanced yellow fluorescent protein (eYFP), Emerald, CyPet, cyan fluorescent protein (CFP), Cerulean, T-Sapphire, luciferase, alkaline phosphatase, or a combination thereof. The methods described herein demonstrate the construction of targeting vectors that employ the use of a lacZ reporter gene that encodes β-galactosidase, however, persons of skill upon reading this disclosure will understand that non-human animals described herein can be generated in the absence of a reporter gene or with any reporter gene known in the art.

Where appropriate, the coding region of the genetic material or polynucleotide sequence(s) encoding a reporter polypeptide, in whole or in part, may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a reporter polypeptide (e.g. lacZ), in whole or in part, may include an altered sequence to optimize codon usage for a particular cell type (e.g., a rodent cell). For example, the codons of the reporter gene to be inserted into the genome of a non-human animal (e.g., a rodent) may be optimized for expression in a cell of the non-human animal. Such a sequence may be described as a codon-optimized sequence.

Compositions and methods for making non-human animals that comprises an insertion of heterologous hexanucleotide repeat expansion sequence disruption in an endogenous C9ORF72 locus as described herein are provided, including compositions and methods for making non-human animals that express the heterologous hexanucleotide repeat expansion sequence, e.g., from a C9ORF72 promoter, e.g., an endogenous mouse promoter, and a C9ORF72 regulatory sequence, e.g., a human regulatory, e.g., found in exons 1a and 1b. In some embodiments, compositions and methods for making non-human animals that express a heterologous hexanucleotide repeat expansion sequence from an endogenous promoter and an endogenous regulatory sequence are also provided. Methods include inserting a targeting vector, as described herein, encoding a heterologous hexanucleotide repeat expansion sequence into the genome of a non-human animal so that a non-coding sequence of a C9ORF72 locus is deleted, in whole or in part. In some embodiments, a non-human animal described herein comprises an endogenous C9ORF72 locus that comprises a targeting vector as described herein.

Targeting vectors described herein may be introduced into ES cells and screened for ES clones harboring a disruption in a C9orf72 locus as described in Frendewey, D., et al., 2010, Methods Enzymol. 476:295-307. A variety of host embryos can be employed in the methods and compositions disclosed herein. For example, the pluripotent and/or totipotent cells having the targeted genetic modification can be introduced into a pre-morula stage embryo (e.g., an 8-cell stage embryo) from a corresponding organism. See, e.g., U.S. Pat. Nos. 7,576,259, 7,659,442, 7,294,754, and US 2008/0078000 A1, all of which are incorporated by reference herein in their entireties. In other cases, the donor ES cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo, an uncompacted morula stage embryo, or a compacted morula stage embryo.

In some embodiments, the VELOCIMOUSE® method (Poueymirou, W. T. et al., 2007, Nat. Biotechnol. 25:91-99) may be applied to inject positive ES cells into an 8-cell embryo to generate fully ES cell-derived F0 generation heterozygous mice ready for lacZ expression profiling or breeding to homozygosity. Exemplary methods for generating non-human animals having a disruption in a C9orf72 locus are provided in Example 1.

Methods for generating transgenic non-human animals, including knockouts and knock-ins, are well known in the art (see, e.g., Gene Targeting: A Practical Approach, Joyner, ed., Oxford University Press, Inc. (2000)). For example, generation of transgenic rodents may optionally involve disruption of the genetic loci of an endogenous rodent gene and introduction of a reporter gene into the rodent genome, in some embodiments, at the same location as the endogenous rodent gene.

A schematic illustration (not to scale) of the genomic organization of a mouse C9orf72 is provided in FIG. 1A (top box). An exemplary targeting strategy for replacement of a non-coding sequence of an endogenous murine C9orf72 locus with a heterologous hexanucleotide repeat expansion sequence is also provided in FIG. 1A (bottom box). As illustrated, genomic DNA spanning between exon 1 and the ATG start codon, or a portion thereof, is replaced with a heterologous hexanucleotide repeat expansion sequence and a drug selection cassette flanked by site-specific recombinase recognition sites. The targeting vector used in this strategy may optionally include a recombinase-encoding sequence that is operably linked to a promoter that is developmentally regulated such that the recombinase is expressed in undifferentiated cells. Exemplary developmentally regulated promoters that can be included in targeting vectors described herein are provided in Table 3. Additional suitable promoters that can be used in targeting vectors described herein include those described in U.S. Pat. Nos. 8,697,851, 8,518,392 and 8,354,389; all of which are herein incorporated by reference). Upon homologous recombination, the non-coding sequence, e.g., approximately 800-1000 bp spanning from exon 1 (or within exon 1) to exon 2, of the endogenous murine C9orf72 locus is replaced by the sequence contained in the targeting vector. The drug selection cassette may be removed, e.g., optionally in a development-dependent manner such that progeny derived from mice whose germ line cells containing a disruption in a C9orf72 locus described above will shed the selectable marker from differentiated cells during development (see U.S. Pat. Nos. 8,697,851, 8,518,392 and 8,354,389, all of which are herein incorporated by reference).

TABLE 3

Prot promoter (SEQ ID NO: 26)
CCAGTAGCAGCACCCACGTCCACCTTCTGTCTAGTAATGTCCAACACCTC
CCTCAGTCCAAACACTGCTCTGCATCCATGTGGCTCCCATTTATACCTGA
AGCACTTGATGGGGCCTCAATGTTTTACTAGAGCCCACCCCCCTGCAACT
CTGAGACCCTCTGGATTTGTCTGTCAGTGCCTCACTGGGGCGTTGGATAA
TTTCTTAAAAGGTCAAGTTCCCTCAGCAGCATTCTCTGAGCAGTCTGAAG
ATGTGTGCTTTTCACAGTTCAAATCCATGTGGCTGTTTCACCCACCTGCC
TGGCCTTGGGTTATCTATCAGGACCTAGCCTAGAAGCAGGTGTGTGGCAC
TTAACACCTAAGCTGAGTGACTAACTGAACACTCAAGTGGATGCCATCTT
TGTCACTTCTTGACTGTGACACAAGCAACTCCTGATGCCAAAGCCCTGCC
CACCCCTCTCATGCCCATATTTGGACATGGTACAGGTCCTCACTGGCCAT
GGTCTGTGAGGTCCTGGTCCTCTTTGACTTCATAATTCCTAGGGGCCACT
AGTATCTATAAGAGGAAGAGGGTGCTGGCTCCCAGGCCACAGCCCACAAA
ATTCCACCTGCTCACAGGTTGGCTGGCTCGACCCAGGTGGTGTCCCCTGC
TCTGAGCCAGCTCCCGGCCAAGCCAGCACC Blimp1 promoter 1kb (SEQ ID NO: 27)
TGCCATCATCACAGGATGTCCTTCCTTCTCCAGAAGACAGACTGGGGCTG
AAGGAAAAGCCGGCCAGGCTCAGAACGAGCCCCACTAATTACTGCCTCCA
ACAGCTTTCCACTCACTGCCCCCAGCCCAACATCCCCTTTTTAACTGGGA
AGCATTCCTACTCTCCATTGTACGCACACGCTCGGAAGCCTGGCTGTGGG
TTTGGGCATGAGAGGCAGGGACAACAAAACCAGTATATATGATTATAACT
TTTTCCTGTTTCCCTATTTCCAAATGGTCGAAAGGAGGAAGTTAGGTCTA
CCTAAGCTGAATGTATTCAGTTAGCAGGAGAAATGAAATCCTATACGTTT
AATACTAGAGGAGAACCGCCTTAGAATATTTATTTCATTGGCAATGACTC
CAGGACTACACAGCGAAATTGTATTGCATGTGCTGCCAAAATACTTTAGC
TCTTTCCTTCGAAGTACGTCGGATCCTGTAATTGAGACACCGAGTTTAGG
TGACTAGGGTTTTCTTTTGAGGAGGAGTCCCCCACCCCGCCCCGCTCTGC
CGCGACAGGAAGCTAGCGATCCGGAGGACTTAGAATACAATCGTAGTGTG
GGTAAACATGGAGGGCAAGCGCCTGCAAAGGGAAGTAAGAAGATTCCCAG
TCCTTGTTGAAATCCATTTGCAAACAGAGGAAGCTGCCGCGGGTCGCAGT
CGGTGGGGGAAGCCCTGAACCCCACGCTGCACGGCTGGGCTGGCCAGGT
GCGGCCACGCCCCATCGCGGCGGCTGGTAGGAGTGAATCAGACCGTCAG
TATTGGTAAAGAAGTCTGCGGCAGGGCAGGGAGGGGGAAGAGTAGTCAGT
CGCTCGCTCACTCGCTCGCTCGCACAGACACTGCTGCAGTGACACTCGGC
CCTCCAGTGTCGCGGAGACGCAAGAGCAGCGCGCAGCACCTGTCCGCCCG
GAGCGAGCCCGCCCGCGGCCGTAGAAAGGAGGGACCGCCGAGGTGCGC
GTCAGTACTGCTCAGCCCGGCAGGGACGCGGGAGGATGTGGACTGGGTGG
AC Blimp1 promoter 2kb (SEQ ID NO: 28)
GTGGTGCTGACTCAGCATCGGTTAATAAACCCTCTGCAGGAGGCTGGATT
TCTTTTGTTTAATTATCACTTGGACCTTTCTGAGAACTCTTAAGAATTGT
TCATTCGGGTTTTTTTGTTTTGTTTTGGTTTGGTTTTTTTGGGTTTTTTT
TTTTTTTTTTTTTTGGTTTTTGGAGACAGGGTTTCTCTGTATATAGCCC
TGGCACAAGAGCAAGCTAACAGCCTGTTTCTTCTTGGTGCTAGCGCCCCC
TCTGGCAGAAAATGAAATAACAGGTGGACCTACAACCCCCCCCCCCCCCC
CCAGTGTATTCTACTCTTGTCCCCGGTATAAATTTGATTGTTCCGAACTA
CATAAATTGTAGAAGGATTTTTTAGATGCACATATCATTTTCTGTGATAC
CTTCCACACACCCCTCCCCCCCAAAAAAATTTTTCTGGGAAAGTTTCTTG
AAAGGAAAACAGAAGAACAAGCCTGTCTTTATGATTGAGTTGGGCTTTTG
TTTTGCTGTGTTTCATTTCTTCCTGTAAACAAATACTCAAATGTCCACTT
CATTGTATGACTAAGTTGGTATCATTAGGTTGGGTCTGGGTGTGTGAATG
TGGGTGTGGATCTGGATGTGGGTGGGTGTGTATGCCCCGTGTGTTTAGAA
TACTAGAAAAGATACCACATCGTAAACTTTTGGGAGAGATGATTTTTAAA
AATGGGGGTGGGGGTGAGGGGAACCTGCGATGAGGCAAGCAAGATAAGGG
GAAGCTTGAGTTTCTGTGATCTAAAAAGTCGCTGTGATGGGATGCTGGC
TATAAATGGGCCCTTAGCAGCATTGTTTCTGTGAATTGGAGGATCCCTGC
TGAAGGCAAAAGACCATTGAAGGAAGTACCGCATCTGGTTTGTTTTGTAA
TGAGAAGCAGGAATGCAAGGTCCACGCTCTTAATAATAAACAAACAGGAC
ATTGTATGCCATCATCACAGGATGTCCTTCCTTCTCCAGAAGACAGACTG
GGGCTGAAGGAAAAGCCGGCCAGGCTCAGAACGAGCCCCACTAATTACTG
CCTCCAACAGCTTTCCACTCACTGCCCCCAGCCCAACATCCCCTTTTTAA
CTGGGAAGCATTCCTACTCTCCATTGTACGCACACGCTCGGAAGCCTGGC
TGTGGGTTTGGGCATGAGAGGCAGGGACAACAAAACCAGTATATATGATT
ATAACTTTTTCCTGTTTCCCTATTTCCAAATGGTCGAAAGGAGGAAGTTA
GGTCTACCTAAGCTGAATGTATTCAGTTAGCAGGAGAAATGAAATCCTAT
ACGTTTAATACTAGAGGAGAACCGCCTTAGAATATTTATTTCATTGGCAA
TGACTCCAGGACTACACAGCGAAATTGTATTGCATGTGCTGCCAAAATAC
TTTAGCTCTTTCCTTCGAAGTACGTCGGATCCTGTAATTGAGACACCGAG
TTTAGGTGACTAGGGTTTTCTTTTGAGGAGGAGTCCCCCACCCCGCCCCG
CTCTGCCGCGACAGGAAGCTAGCGATCCGGAGGACTTAGAATACAATCGT
AGTGTGGGTAAACATGGAGGGCAAGCGCCTGCAAAGGGAAGTAAGAAGAT
TCCCAGTCCTTGTTGAAATCCATTTGCAAACAGAGGAAGCTGCCGCGGGT
CGCAGTCGGTGGGGGAAGCCCTGAACCCCACGCTGCACGGCTGGGCTGG
CCAGGTGCGGCCACGCCCCATCGCGGCGGCTGGTAGGAGTGAATCAGAC
CGTCAGTATTGGTAAAGAAGTCTGCGGCAGGGCAGGGAGGGGGAAGAGTA
GTCAGTCGCTCGCTCACTCGCTCGCTCGCACAGACACTGCTGCAGTGACA
CTCGGCCCTCCAGTGTCGCGGAGACGCAAGAGCAGCGCGCAGCACCTGTC
CGCCCGGAGCGAGCCCGGCCCGCGGCCGTAGAAAGGAGGGACCGCCGAG
GTGCGCGTCAGTACTGCTCAGCCCGGCAGGGACGCGGGAGGATGTGGACT
GGGTGGAC D. Introduction of LTVEC into Cells LTVEC DNA can be introduced into eukaryotic cells using any standard methodology. "Introducing" includes presenting to the cell the nucleic acid in such a manner that the sequence gains access to the interior of the cell. The introducing can be accomplished by any means.

The methods provided herein do not depend on a particular method for introducing a nucleic acid into the cell, only that the nucleic acid gains access to the interior of a least one cell. Methods for introducing nucleic acids into various cell types are known in the art and include, for example, stable transfection methods, transient transfection methods, and virus-mediated methods.

Transfection protocols as well as protocols for introducing nucleic acids into cells may vary. Non-limiting transfection methods include chemical-based transfection methods using liposomes; nanoparticles; calcium phosphate (see, e.g., Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97, each of which is herein incorporated by reference in its entirety); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (see, e.g., Bertram (2006) *Current Pharmaceutical Biotechnology* 7,277-285, herein incorporated by reference in its entirety). Viral methods can also be used for transfection.

Introduction of nucleic acids into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids into a cell (e.g., a one-cell stage embryo) can also be accomplished by microinjection. In one-cell stage embryos, microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a protein or a DNA encoding a DNA encoding a Cas protein is preferably into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a nuclease agent protein is injected into the cytoplasm, the protein preferably comprises a nuclear localization signal to ensure delivery to the nucleus/pronucleus. Methods for carrying out microinjection are well known. See, e.g., Nagy et al., 2003, Manipulating the Mouse Embryo. Cold Spring Harbor, New York: Cold Spring Harbor Laboratory Press); Meyer et al. (2010) *Proc. Natl. Acad. Sci. U.S.A.* 107:15022-15026, and Meyer et al. (2012) *Proc. Natl. Acad. Sci. USA* 109:9354-9359, each of which is herein incorporated by reference in its entirety.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery.

The introduction of nucleic acids into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Screening for and Identifying Cells with Targeted Genetic Modifications

Cells in which the LTVEC has been introduced successfully can be selected by exposure to selection agents, depending on whether a selectable marker gene that has been engineered into the LTVEC. As a non-limiting example, if the selectable marker is the neomycin phosphotransferase (neo) gene (see, e.g., Beck et al. (1982) *Gene* 19:327-336, herein incorporated by reference in its entirety for all purposes), then cells that have taken up the LTVEC can be selected in G418-containing media; cells that do not have the LTVEC will die whereas cells that have taken up the LTVEC will survive (see, e.g., Santerre, et al. (1984) *Gene* 30:147-156, herein incorporated by reference in its entirety for all purposes). Such selection markers can, for example, impart resistance to an antibiotic such as G418, hygromycin, blasticidin, neomycin, or puromycin. Such selection markers include neomycin phosphotransferase (neo$^r$), hygromycin B phosphotransferase (hyg$^r$), puromycin-N-acetyltransferase (puro$^r$), and blasticidin S deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hypoxanthine-guanine phosphoribosyltransferase (HGPRT) or herpes simplex virus thymidine kinase (HSV-TK).

The methods disclosed herein can further comprise identifying a cell having a modified genome. Various methods can be used to identify cells having a targeted genetic modification, such as a deletion or an insertion. Such methods can comprise identifying one cell having the targeted genetic modification at a target locus.

Conventional assays for screening for targeted modifications, such as long-range PCR, Sanger sequencing, or Southern blotting, link the inserted targeting vector to the targeted locus. For example, for a long-range PCR assay, one primer can recognize a sequence within the inserted DNA while the other recognizes a genomic region of interest sequence beyond the ends of the targeting vector's homology arms. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/

0178879 and Frendewey et al. (2010) *Methods Enzymol.* 476:295-307, each of which is herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

The screening step can also comprise arm-specific assays, which are assays used to distinguish between correct targeted insertions of a nucleic acid insert into a target genomic locus from random transgenic insertions of the nucleic acid insert into genomic locations outside of the target genomic locus. Arm-specific assays determine copy numbers of a DNA template in LTVEC homology arms. See, e.g., US 2016/0177339, WO 2016/100819, US 2016/0145646, and WO 2016/081923, each of which is herein incorporated by reference in its entirety for all purposes. It can be useful augment standard LOA and GOA assays to verify correct targeting by LTVECs. For example, LOA and GOA assays alone may not distinguish correctly targeted cell clones from clones in which a deletion of the target genomic locus coincides with random integration of a LTVEC elsewhere in the genome. Because the selection pressure in the targeted cell is based on the selection cassette, random transgenic integration of the LTVEC elsewhere in the genome will generally include the selection cassette and adjacent regions of the LTVEC but may exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, in some cases the 3' homology arm but not the 5' homology arm will be transgenically integrated with the selection cassette. Alternatively, if the selection cassette adjacent to the 5' homology arm, in some cases the 5' homology arm but not the 3' homology arm will be transgenically integrated with the selection cassette. As an example, if LOA and GOA assays are used to assess targeted integration of the LTVEC, and the GOA assay utilizes probes against the selection cassette or any other unique (non-arm) region of the LTVEC, a heterozygous deletion at the target genomic locus combined with a random transgenic integration of the LTVEC will give the same readout as a heterozygous targeted integration of the LTVEC at the target genomic locus. To verify correct targeting by the LTVEC, arm-specific assays can be used in conjunction with LOA and/or GOA assays.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next generation sequencing (NGS) can also be used for screening, particularly in one-cell stage embryos that have been modified. Next-generation sequencing can also be referred to as "NGS" or "massively parallel sequencing" or "high throughput sequencing." Such NGS can be used as a screening tool in addition to the MOA assays and retention assays to define the exact nature of the targeted genetic modification and to detect mosaicism. Mosaicism refers to the presence of two or more populations of cells with different genotypes in one individual who has developed from a single fertilized egg (i.e., zygote). In the methods disclosed herein, it is not necessary to screen for targeted clones using selection markers. For example, the MOA and NGS assays described herein can be relied on without using selection cassettes.

F. Methods of Making Genetically Modified Non-Human Animals

Genetically modified non-human animals can be generated employing the various methods disclosed herein. Any convenient method or protocol for producing a genetically modified organism, including the methods described herein, is suitable for producing such a genetically modified non-human animal. Such methods starting with genetically modifying a pluripotent cell such as an embryonic stem (ES) cell generally comprise: (1) modifying the genome of a pluripotent cell that is not a one-cell stage embryo using the methods described herein; (2) identifying or selecting the genetically modified pluripotent cell; (3) introducing the genetically modified pluripotent cell into a host embryo; and (4) implanting and gestating the host embryo comprising the genetically modified pluripotent cell in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be, for example, an ES cell (e.g., a rodent ES cell, a mouse ES cell, or a rat ES cell) as discussed elsewhere herein. See, e.g., U.S. Pat. No. 7,294,754, herein incorporated by reference in its entirety for all purposes.

Alternatively, such methods starting with genetically modifying a one-cell stage embryo generally comprise: (1) modifying the genome of a one-cell stage embryo using the methods described herein; (2) identifying or selecting the genetically modified embryo; and (3) implanting and gestating the genetically modified embryo in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of a non-human animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal that comprise the targeted genetic modification. It is recognized that depending on the method used to generate the F0 animal, the number of cells within the F0 animal that have the targeted genetic modification will vary. The introduction of the donor ES cells into a pre-morula stage embryo from a corresponding organism (e.g., an 8-cell stage mouse embryo) via, for example, the VELOCIMOUSE® method allows for a greater percentage of the cell population of the F0 animal to comprise cells having the targeted genetic modification. See, e.g., US 2014/0331340, US 2008/0078001, US 2008/0028479, US 2006/0085866, and WO 2006/044962, each of which is herein incorporated by reference in its entirety for all purposes. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted genetic modification. In addition, at least one or more of the germ cells of the F0 animal can have the targeted genetic modification.

A genetically modified founder non-human animal can be identified based upon the absence of endogenous genomic C9ORF72 sequences in its genome that are replaced with the heterologous hexanucleotide repeat expansion sequence and/or the presence (and/or expression) of the heterologous hexanucleotide repeat expansion sequence, drug resistance gene and/or reporter in tissues or cells of the non-human animal. A transgenic founder non-human animal can then be used to breed additional non-human animals carrying the heterologous hexanucleotide repeat expansion sequence thereby creating a series of non-human animals each carrying one or more copies of a C9ORF72 locus as described herein.

Transgenic non-human animals may also be produced to contain selected systems that allow for regulated or directed expression of the transgene. Exemplary systems include the Cre/loxP recombinase system of bacteriophage P1 (see, e.g., Lakso, M. et al., 1992, Proc. Natl. Acad. Sci. USA 89:6232-6236) and the FLP/Frt recombinase system of *S. cerevisiae* (O'Gorman, S. et al, 1991, Science 251:1351-1355). Such animals can be provided through the construction of "double" transgenic animals, e.g., by mating two transgenic animals, one containing a transgene encoding the heterologous hexanucleotide repeat expansion sequence and the other containing a transgene encoding a recombinase (e.g., a Cre recombinase).

Although embodiments employing an insertion of a heterologous hexanucleotide repeat expansion sequence in an endogenous C9ORF72 locus in a mouse are extensively discussed herein, other non-human animals that comprise a disruption in a C9ORF72 locus are also provided. Such non-human animals include any of those which can be genetically modified to replace a non-coding sequence of a C9ORF72 locus as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Briefly, methods for nuclear transfer include steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes may be matured in a variety of medium known to persons of skill in the art prior to enucleation.

Enucleation of the oocyte can be performed in a variety of ways known to persons of skill in the art. Insertion of a donor cell or nucleus into an enucleated oocyte to form a reconstituted cell is typically achieved by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium known to persons of skill in the art and then transferred to the womb of an animal. See, e.g., U.S. Patent Application Publication No. 2008-0092249 A1, WO 1999/005266 A2, U.S. Patent Application Publication No. 2004-0177390 A1, WO 2008/017234 A1, and U.S. Pat. No. 7,612,250, each of which is herein incorporated by reference.

Methods for modifying a non-human animal genome (e.g., a pig, cow, rodent, chicken, etc.) include, e.g., employing a zinc finger nuclease (ZFN) or a transcription activator-like effector nuclease (TALEN) to modify a genome to include an insertion of a heterologous hexanucleotide repeat expansion sequence in a C9ORF72 locus as described herein.

In some embodiments, a non-human animal described herein is a mammal. In some embodiments, a non-human animal described herein is a small mammal, e.g., of the superfamily Dipodoidea or Muroidea. In some embodiments, a genetically modified animal described herein is a rodent. In some embodiments, a rodent described herein is selected from a mouse, a rat, and a hamster. In some embodiments, a rodent described herein is selected from the superfamily Muroidea. In some embodiments, a genetically modified animal described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent described herein is selected from a true mouse or rat (family Muridae), a gerbil, a spiny mouse, and a crested rat. In some certain embodiments, a genetically modified mouse described herein is from a member of the family Muridae. In some embodiment, a non-human animal described herein is a rodent. In some certain embodiments, a rodent described herein is selected from a mouse and a rat. In some embodiments, a non-human animal described herein is a mouse.

In some embodiments, a non-human animal described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5): 1024-1028, 1030, 1032). In some certain embodiments, a genetically modified mouse described herein is a mix of an aforementioned 129 strain and an aforementioned C57BL/6 strain. In some certain embodiments, a mouse described herein is a mix of aforementioned 129 strains, or a mix of aforementioned BL/6 strains. In some certain embodiments, a 129 strain of the mix as described herein is a 129S6 (129/SvEvTac) strain. In some embodiments, a mouse described herein is a BALB strain, e.g., BALB/c strain. In some embodiments, a mouse described herein is a mix of a BALB strain and another aforementioned strain.

In some embodiments, a non-human animal described herein is a rat. In some certain embodiments, a rat described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat are the DA.2B rat ES cell line and the DA.2C rat ES cell line. In some cases, the rat pluripotent and/or totipotent cells are from an inbred rat strain. See, e.g., U.S. 2014/0235933 A1, filed on Feb. 20, 2014, and herein incorporated by reference in its entirety.

Non-human animals are provided that comprise an insertion of a heterologous hexanucleotide repeat expansion sequence in an endogenous C9ORF72 locus. In some embodiments, insertion of a heterologous hexanucleotide repeat expansion sequence is not pathogenic. In some embodiments, insertion of a heterologous hexanucleotide repeat expansion sequence results in one or more phenotypes as described herein, e.g., a phenoytpe associated with ALS and/or FTD. Insertion of a heterologous hexanucleotide repeat expansion sequence may be measured directly, e.g., by determining the approximate number of instance, e.g., repeats, of the hexanucleotide sequence set forth as SEQ ID NO:1 in the heterologous hexanucleotide repeat expansion sequence, e.g., by Southern Blot or polymerase chain reaction genotyping reactions.

Methods Employing Non-human Animals Having An Insertion of a Heterologous Hexanucleotide Repeat Expansion Sequence in an Endogenous C9ORF72 Locus Non-human animals as described herein provide improved animal models for neurodegenerative diseases, disorders and conditions. In particular, non-human animals as described herein provide improved animal models that translate to human diseases such as, for example, ALS and/or FTD, characterized by upper motor neuron symptoms and/or non-motor neuron loss.

Non-human animals as described herein provide an improved in vivo system and source of biological materials (e.g., cells) that comprise and/or express the inserted pathogenic heterologous hexanucleotide repeat expansion sequence in an endogenous C9ORF72 locus that are useful for a variety of assays. In various embodiments, non-human animals described herein may be used to develop therapeutics that treat, prevent and/or inhibit one or more symptoms associated with expression and/or activity of a pathogenic heterologous hexanucleotide repeat expansion. In various embodiments, non-human animals described herein are used to identify, screen and/or develop candidate therapeutics (e.g., antibodies, gRNAs (comprising CRISPR RNA and tracRNA) and siRNA, etc.) that bind a pathogenic heterologous hexanucleotide repeat expansion sequence or expression product thereof, e.g., resulting from RAN translation. In various embodiments, non-human animals described herein are used to screen and develop candidate therapeutics (e.g., antibodies, gRNAs (comprising CRISPR RNA and tracRNA) and siRNA, etc.) that block activity of a pathogenic heterologous hexanucleotide repeat expansion sequence or expression product thereof, e.g., resulting from RAN translation. In various embodiments, non-human animals described herein are used to determine the binding profile of antagonists and/or agonists of a pathogenic heterologous hexanucleotide repeat expansion sequence or expression product thereof (transcript), e.g., resulting from RAN translation, of a non-human animal as described herein. In some embodiments, non-human animals described herein are used to determine the epitope or epitopes of one or more candidate therapeutic antibodies that bind a pathogenic heterologous hexanucleotide repeat expansion sequence or expression product thereof, e.g., resulting from RAN translation.

In various embodiments, non-human animals described herein are used to determine the pharmacokinetic profiles of a drug targeting a pathogenic heterologous hexanucleotide repeat expansion sequence or expression product thereof, e.g., resulting from RAN translation. In various embodiments, one or more non-human animals described herein and one or more control or reference non-human animals are each exposed to one or more candidate drugs targeting a pathogenic heterologous hexanucleotide repeat expansion sequence or expression product thereof, e.g., resulting from RAN translation, at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered drugs targeting a pathogenic heterologous hexanucleotide repeat expansion sequence or expression product thereof, e.g., resulting from RAN translation, using samples obtained from non-human animals as described herein including, but not limited to, total IgG, anti-therapeutic antibody response, agglutination, etc.

In various embodiments, non-human animals as described herein are used to measure the therapeutic effect of blocking, modulating, and/or inhibiting activity of a pathogenic heterologous hexanucleotide repeat expansion sequence or expression product thereof, e.g., resulting from Repeat-associated non-AUG (RAN) translation, and the effect on gene expression as a result of cellular changes. In various embodiments, a non-human animal as described herein or cells isolated therefrom are exposed to a drug targeting a pathogenic heterologous hexanucleotide repeat expansion sequence or expression product thereof, e.g., resulting from RAN translation, of the non-human animal and, after a subsequent period of time, analyzed for effects on processes (or interactions) dependent on the pathogenic heterologous hexanucleotide repeat expansion sequence or expression product thereof, e.g., resulting from RAN translation, for example, formation of RNA foci, protein aggregation from RAN translation products, motor neuron and/or non-motor neuron function, etc.

Cells from non-human animals as described herein can be isolated and used on an ad hoc basis, or can be maintained in culture for many generations. In various embodiments, cells from a non-human animal as described herein are immortalized (e.g., via use of a virus) and maintained in culture indefinitely (e.g., in serial cultures).

Non-human animals described herein provide an in vivo system for assessing the pharmacokinetic properties and/or efficacy of a drug (e.g., a drug targeting a pathogenic heterologous hexanucleotide repeat expansion sequence or expression product thereof, e.g., resulting from RAN translation). In various embodiments, a drug may be delivered or administered to one or more non-human animals, cells derived therefrom or having the same genetic modifications thereof, as described herein, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, but not limited to, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs are monitored in or through the use of non-human animals described herein.

In some embodiments, performing an assay includes determining the effect on the phenotype and/or genotype of the non-human animal to which the drug is administered. In some embodiments, performing an assay includes determining lot-to-lot variability for a drug. In some embodiments, performing an assay includes determining the differences between the effects of a drug administered to a non-human animal described herein and a reference non-human animal. In various embodiments, reference non-human animals may have a modification as described herein, e.g., insertion of a non-pathogenic heterologous hexanucleotide repeat expansion sequence or no modification (i.e., a wild type non-human animal).

Exemplary parameters that may be measured in non-human animals (or in and/or using cells isolated therefrom) for assessing the pharmacokinetic properties of a drug include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity, and the like. In various embodiments, non-human animals described herein are used to determine a pharmaceutically effective dose of a drug (e.g., a drug targeting a pathogenic heterologous hexanucleotide repeat expansion sequence or expression product thereof, e.g., resulting from RAN translation).

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1

Insertion of a Heterologous Hexanucleotide Repeat Expansion Sequence in a Non-human Embryonic Stem Cell at an Endogenous Non-human C9ORF72 Locus This example illustrates a targeted insertion of a heterologous hexanucleotide repeat expansion sequence into an embryonic stem cell at a C9orf72 locus of a non-human animal, particularly rodent. In particular, this example specifically describes the replacement of a part of a non-coding sequence of a mouse C9orf72 locus with a heterologous human hexanucleotide repeat expansion sequence placed in operable linkage with an mouse C9orf72 promoter and/or human regulatory elements, e.g., those that may be found in exons 1a and/or 1b of the human C9orf72 gene. The C9orf72-HRE targeting vector for inserting a heterologous hexanucleotide repeat expansion sequence in an endogenous mouse C9orf72 locus was made as previously described (see, e.g., U.S. Pat. No. 6,586,251; Valenzuela et al., 2003, Nature Biotech. 21(6): 652-659; and Adams, N. C. and N. W. Gale, in Mammalian and Avian Transgenesis—New Approaches, ed. Lois, S. P. a. C., Springer Verlag, Berlin Heidelberg, 2006). The resulting modified C9orf72 locus is depicted in FIG. 1A, bottom box.

Briefly, targeting vectors comprising a sequence set forth in SEQ ID NO:8 or SEQ ID NO:9 were generated using bacterial artificial chromosome (BAC) clones from a mouse RP23 BAC library (Adams, D. J. et al., 2005, Genomics 86:753-758) and introduced into F1 hybrid (129S6SvEvTac/C57BL6NTac) embryonic stem (ES) cells followed by culturing in selection medium containing G418. Drug-resistant colonies were picked 10 days after electroporation and screened for correct targeting as previously described (Valenzuela et al., supra; Frendewey, D. et al., 2010, Methods Enzymol. 476:295-307). Targeted ES cells are analyzed to determine the approximate size of hexanucleotide repeat expansions present in targeted mouse ES cell clones by Southern blot analysis and/or amplification of the C9orf72-HRE locus.

Specifically, Southern blot analysis was performed to determine the approximate size of hexanucleotide repeat expansions present in targeted C9ORF72 transgenic mouse ES cells. Genomic DNA was extracted from targeted mouse ES clones grown in single wells of a gelatin-coated 96 well plate. Once ES cell clones reached 100% confluence, cells were washed twice with 1×PBS and lysed overnight at 37° C. in 50 uL of lysis buffer (1M Tris pH 8.5, 0.5M EDTA, 20% SDS, 5M NaCl, and 1 mg/mL proteinase K). DNA was precipitated with the addition of 125 uL of ice cold 200 proof ethanol to each well, followed by an overnight incubation at 4° C. Precipitated DNA was washed twice with 70% ethanol, air dried, and resuspended in 30 uL 0.5× TE pH 8.0.

Extracted genomic DNAs (gDNA) were digested with HindII and ScaI overnight at 37° C. and size separated on a 1% agarose gel. Post-electrophoresis agarose gels were denatured (1M NaCl, 5% NaOH) and neutralized (1.5M NaCl, 0.5M Tris pH 7.5). Digested gDNAs were then transferred to Hybond-N membranes (Amersham) via overnight capillary transfer.

Figure 2A:
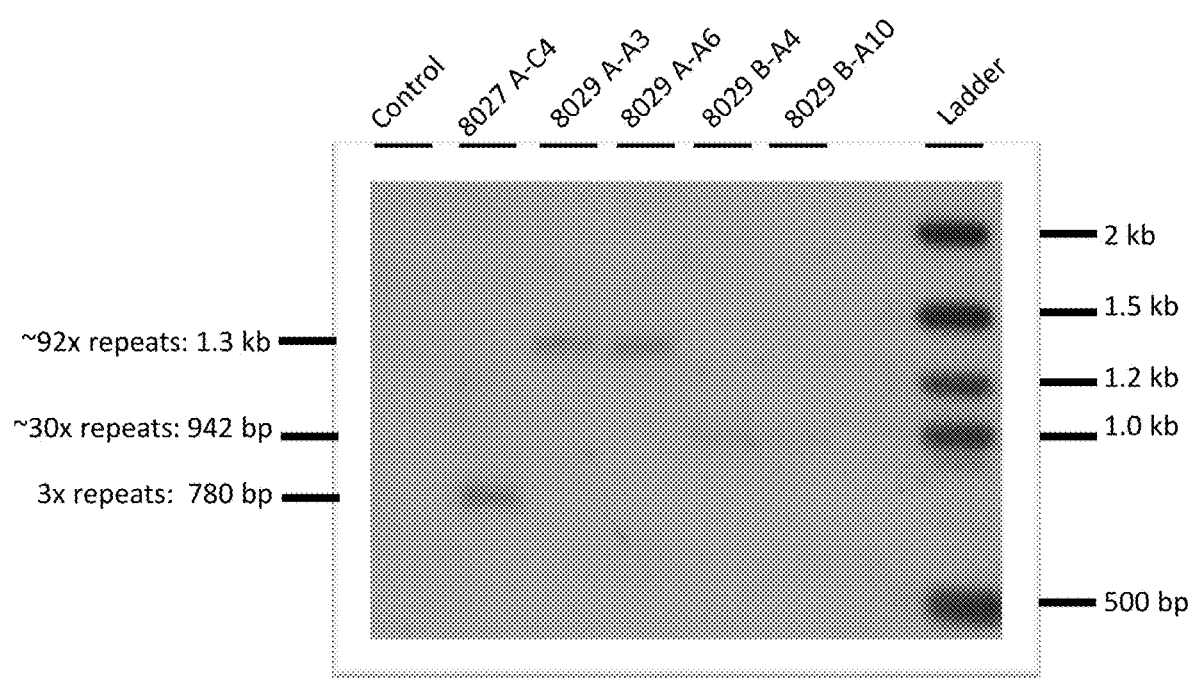
FIG. 2B shows the genotypic results of genotyping samples (n=6) including a control ES cell clone, the 8027 A-C4 clone, the 8029 A-A3 clone, the 8029 A-A6 clone, the 8029 B-A4 clone, the 8029 B-A10 clone, and controls (n=7) obtained from human samples containing three hexanucleotide repeat expansion sequences.

A probe corresponding to a 252 bp XmaI fragment (see FIG. 2A) contained within the humanized targeting vector (5'-CCGGGGCGGGGCTGCGGTTGCGGTGCCTGCGCCCGCGGCGGCG

GAGGCGCAGGCGGTGGCGAGTGGGTGAGTGAGGAGGCGGCATCCTGGCGG

GTGGCTGTTTGGGGTTCGGCTGCCGGGAAGAGGCGCGGGTAGAAGCGGGG

GCTCTCCTCAGAGCTCGACGCATTTTTACTTTCCCTCTCATTTCTCTGAC

CGAAGCTGGGTGTCGGGCTTTCGCCTCTAGCGACTGGTGGAATTGCCTGC

ATCCGGGCC-3'; SEQ ID NO: 29)

was labeled with $^{32}$P using Prime-It II Random Primer Labeling Kit (Agilent). Denatured probe was diluted in ExpressHyb Hybridization Solution (Takara) and incubated with prepared membranes overnight at 65° C. Autoradiography film was exposed to the probed blots for 72 hours.

Figure 2B:
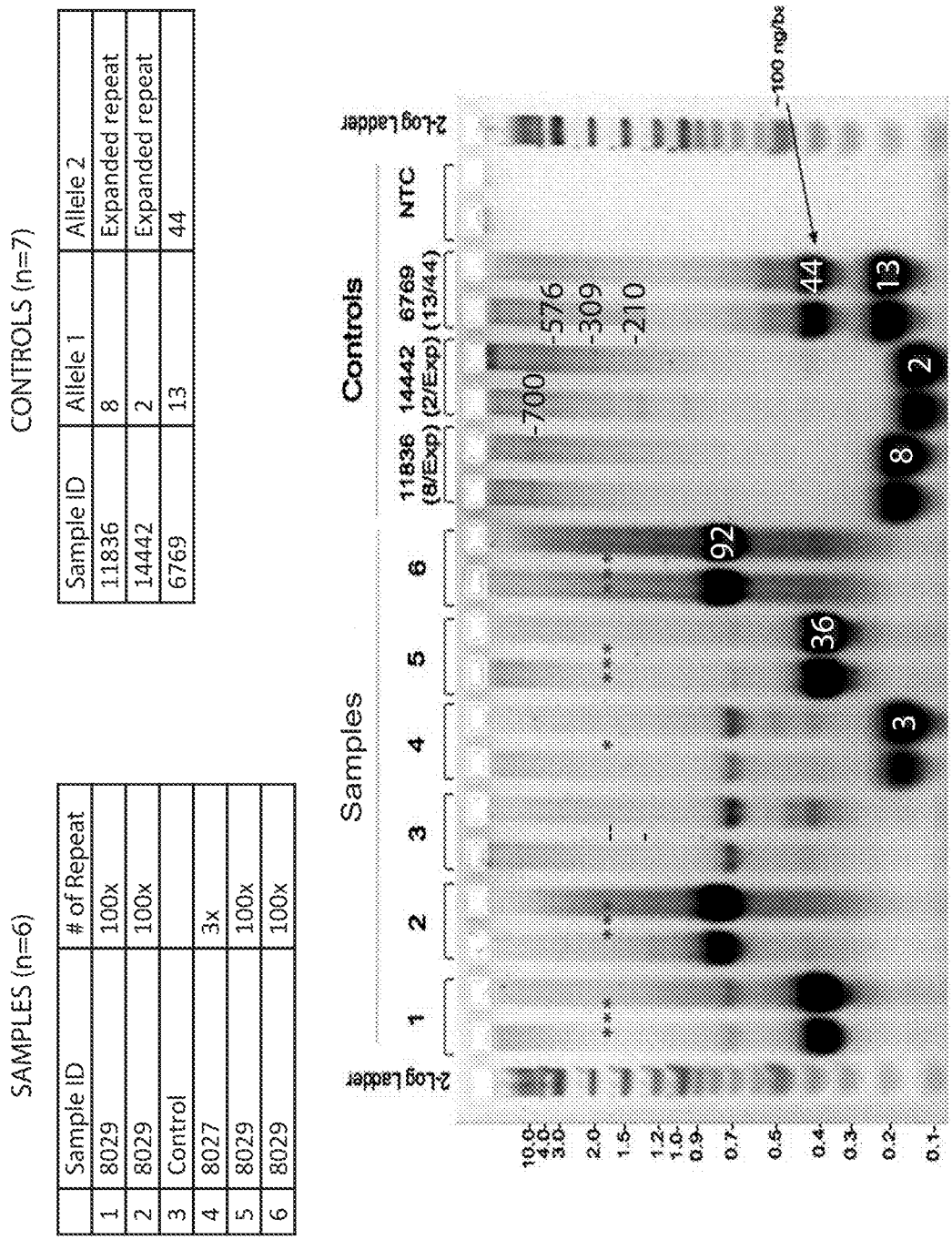

As shown in FIG. 2B, an ES cell clone (8027 A-C4) comprising an inserted non-pathogenic heterologous hexanucleotide repeat expansion sequence comprising three repeats of the hexanucleotide sequence set forth as SEQ ID NO:1 is obtained after introduction of the C9orf72-HRE-3 targeting vector comprising a sequence set forth as SEQ ID NO:4 and excision of the drug resistance cassette. After introduction of the C9orf72-HRE-100 targeting vector comprising a sequence set forth as SEQ ID NO:6, at least two ES cell clones (8029 A-A3 and 8029 A-A6) comprising an inserted heterologous hexanucleotide repeat expansion sequence, which is a variant of the sequence set forth as SEQ ID NO:7 and comprises about 92 repeats of the hexanucleotide sequence set forth as SEQ ID NO:1, were obtained. Also at least two ES cell clones (8029 B-A6 and 8029 B-A4) comprising an inserted heterologous hexanucleotide repeat expansion sequence, which is a variant of the sequence set forth as SEQ ID NO:7 and comprises about 30 repeats of the hexanucleotide sequence set forth as SEQ ID NO:1, were obtained after introduction of the C9orf72-HRE-100 targeting vector (8028) and excision of the drug resistance cassette.

AmplideX PCR/CE C9ORF72 Kit (Asuragen) was also used according to manufacturer's instructions to confirm the number of instances of the hexanucleotide sequence set forth as SEQ ID NO:1 in heterologous hexanucleotide repeat expansion sequence inserted into the endogenous C9orf72 ES cell clones described. Purified mESC genomic total DNA from a 3× repeat clone (8027 A-C4), 2 individual 92× repeat clones (8029 A-A3, 8029 A-A6), and 2 individual 30× repeat clones (8029 B-A4, 8029 B-A10) was used as input DNA. F1H4 mESC genomic total DNA served as negative control, and Coriell Cell Repository purified human blood cell genomic DNA from patients with known C9ORF72 hexanucleotide expanded repeat alleles (samples ND11836 (HRE genotype: 8/expanded), ND14442 (2/expanded), ND6769 (13/44)) served as positive controls (Coriell Institute for Medical Research). PCR using the primers in Table 4 was performed on a ABI 9700 thermal cycler (Thermo Fisher). Amplicons were sized by capillary electrophoresis on a ABI 3500xL GeneScan using POP-7 polymer (Thermo Fisher) and NuSieve agarose gels (Lonza). 2-log DNA ladder (New England BioLabs) molecular weight marker was loaded on agarose gels for comparison, and bands were visualized with SYBR Gold Nucleic Acid Stain (Thermo Fisher).

TABLE 4

| Primer name | Sequence (SEQ ID NO:) |
|---|---|
| 2-Primer Fwd | TGCGCCTCCGCCGCCGCGGGCGCAGGCACCGCAACCGCA (SEQ ID NO: 30) |
| 2-Primer Rev | CGCAGCCTGTAGCAAGCTCTGGAACTCAGGAGTCG (SEQ ID NO: 31) |
| 3-Primer Fwd | ATGCAGGCAATTCCACCAGTCGCTAGAGGCGAAAGC (SEQ ID NO: 32) |
| 3-Primer Rev | TAACCAGAAGAAAACAAGGAGGGAAACAACCGCAGCCTGT (SEQ ID NO: 33) |

FIG. 2B confirms the presence of 3 repeats of the hexanucleotide sequence set forth as SEQ ID NO:1 within the heterologous hexanucleotide repeat expansion sequence inserted into the endogenous C9orf72 locus of mouse ES cell clone 8027 A-C4, about 30 repeats of the hexanucleotide sequence set forth as SEQ ID NO:1 within the heterologous hexanucleotide repeat expansion sequences inserted into the endogenous C9orf72 locus of mouse ES cell clones 8029 B-A9 and 8029 B-A10, and about 92 repeats of the hexanucleotide sequence set forth as SEQ ID NO:1 within the heterologous hexanucleotide repeat expansion sequences at the endogenous C9orf72 locus of mouse ES cell clones 8029 A-A3 and 8029 A-A6.

Example 2

Generation of Embryonic Stem Cell Derived Motor Neurons and Non-human Animals Comprising a Heterologous Hexanucleotide Repeat Expansion Sequence at an Endogenous Mouse C9ORF72 Locus Embryonic Stem Cell Derived Motor Neurons Parental embryonic stem cells (ESCs) homozygous for a wildtype C9orf72 locus (control) or heterozygous for a C9orf72 locus genetically modified with about 3 repeats (C9orf72HRE$_3^{+/-}$), 30 repeats (C9orf72HRE$_{30}^{+/-}$), or 92 repeats ((C9orf72HRE$_{92}^{+/-}$) of the hexanucleotide sequence set forth as SEQ ID NO:1 were cultured in embryonic stem cell medium (ESM; DMEM+15% Fetal bovine serum+Penicillin/Streptomyocin+Glutamine+Non-essential amino acids+nucleosides+β-mercaptoethanol+Sodium pyruvate+LIF) for 2 days, during which the medium was changed daily. ES medium was replaced with 7 ml of ADFNK medium (Advanced DMEM/F12+Neurobasal medium+10% Knockout serum+Penicillin/Streptomyocin+Glutamine+β-mercaptoethanol) 1 hour before trypsinization. ADFNK medium was aspirated and ESC were trypsinized with 0.05% trypsin—EDTA. Pelleted cells were resuspended in 12ml of ADFNK and grown for two days in suspension. Cells were cultured for a further 4 days in ADFNK supplemented with retinoic acid (RA) and smoothened agonist to obtain motor neurons (ESMNs). Dissociated motor neurons were plated and matured in embryonic stem cell-derived motor neuron medium (ESMN; Neurobasal medium+2% Horse serum+B27+Glutamine+Penicillin/Streptomyocin+β-mercaptoethanol+10 ng/ml GDNF, BDNF, CNTF).

Non-human Animals

The VELOCIMOUSE® method (DeChiara, T. M. et al., 2010, Methods Enzymol. 476:285-294; Dechiara, T. M., 2009, Methods Mol. Biol. 530:311-324; Poueymirou et al., 2007, Nat. Biotechnol. 25:91-99) was used, in which targeted ES cells were injected into uncompacted 8-cell stage Swiss Webster embryos, to produce healthy fully ES cell-derived F0 generation mice heterozygous for the C9orf72-HRE (3× or 100×) insertion. F0 generation heterozygous male were crossed with C57B16/NTac females to generate F1 heterozygotes that were intercrossed to produce F2 generation C9orf72-HRE$^{+/+}$, C9orf72-HRE$^{+/-}$ and wild type mice for molecular and phenotypic analyses.

Example 3

Analysis of Motor Neurons or Brain Tissues having a Heterologous Hexanucleotide Repeat Expansion Sequence in an Endogenous C9orf72 Locus Recently, Liu et al. (2017) *Cell Chem. Biol.* 24:141-148 used quantitative polymerase chain reaction (qPCR) and digital droplet polymerase chain reaction (ddPCR) to quantify the copy number of sense and antisense RNA transcripts from the C9orf72 locus expressed by human fibroblast cell lines, or human astrocytes and motor neurons derived from induced pluripotent stem cells (iPSCs), isolated from patients suffering from ALS. Liu et al. (2017), supra, detected significantly higher numbers of sense intronic, antisense, and sense C9orf72 transcripts in patient-derived fibroblasts compared to fibroblasts derived from healthy patients. On average, three to four copies of C9orf72 intronic and antisense transcripts, and about 15-20 copies of C9orf72 sense mRNA transcripts, were detected per patient-derived fibroblast. Liu et al. (2017) supra. Liu et al. (2017) et al., supra, show that, in contrast, one or less intronic and antisense transcripts, and 5-10 copies of C9orf72 sense mRNA transcripts, were detected in non-disease fibroblast cell lines. Similarly to the fibroblasts, expression of intronic, antisense, and sense C9orf72 transcripts was higher in patient-derived astrocytes and neuronal cells compared to healthy-control derived astrocytes and neuronal cells. Liu et al. (2017) et al., supra. By calculating the percentage of cells that contain RNA foci, the average number of foci per cell, and the distribution of different numbers of foci among cells, and in determining the number of C9orf72 transcripts in disease- or healthy- derived cells, Liu et al. (2017) et al., supra, suggested that the each foci seen in disease-derived cell is a single mutant C9orf72 intronic or antisense transcript, and further, that small numbers of RNA molecules may have a sizable impact on disease.

In this example, the stability of the size of the hexanucleotide repeat in a breeding colony was confirmed in F2 animals using AmplideX PCR/CE C9ORF72 Kit (Asuragen)

as described above (data not shown). Additionally, RNA transcripts in mouse embryonic stem cell derived motor neurons (ESMNs), brain tissues, and parental embryonic stem cells comprising a wildtype C9orf72 locus (control) or a genetically modified C9orf72 locus that comprises three, thirty, or ninety-two repeats of the hexanucleotide sequence set forth in SEQ ID NO:1 were examined. RNA foci and dipeptide repeat protein levels were also evaluated in ESMNs derived from parental embryonic stem cells comprising a wildtype C9orf72 locus (control) or a genetically modified C9orf72 locus that comprises three, thirty, or ninety-two repeats of the hexanucleotide sequence set forth in SEQ ID NO:1.

Materials and Methods

Quantitative Polymerase Chain Reaction

Total RNA from each sample was extracted and reverse transcribed using primers that flank various regions, and probes that detect those regions of the modified C9orf72-HRE locus. Detectable regions include those that span the junction of mouse and human sequences, only human sequences, or only mouse sequences. QPCR of GAPDH or β2-microglobulin was performed using probes and primers of readily available kits.

Specifically, RNA was isolated from embryonic stem cell-derived motor neurons (ESMN), parental embryonic stem (ES) cells, or total brains isolated from mice comprising a wildtype (WT) C9orf72 locus (control) or a genetically modified C9orf72 locus comprising 3, 30 or 92 repeats of the hexanucleotide sequence set forth as SEQ ID NO:1

Total RNA was isolated using Direct-zol RNA Miniprep plus kit according to the manufacturer's protocol (Zymo Research). About 1 μg total RNA was t treated with DNase I (ThermoFisher) at 25° C. for 15 min. EDTA was added and the mixture incubated at 65° C. for 10 min. Reverse transcription (RT) reactions were performed with a Maxima H Minus First Strand cDNA Synthesis Kit with dsDNase (ThermoFisher). After DNase I treatment, 10 μL of RT mixture containing RT buffer, random hexamer primers, dNTPs, Maxima H minus enzyme mix was added to make final volume of 20 μL. The RT reaction mixture was incubated at 25° C. for 10 min, then at 50° C. for 15 min, and then 5 min at 85° C. to inactivate the enzyme. The cDNA mix was diluted with water to make 100 μL final volume.

After reverse transcription, the PCR reaction solution was reconstituted to a final volume of 8 μL containing 3 μL cDNA and 5 μL of PCR mixture, probe and gene specific primers. Unless otherwise noted final primer and probe concentrations were 0.5 μM and 0.25 μM respectively. qPCR was performed on a ViiA™ 7 Real-Time PCR Detection System (ThermoFisher). PCR reactions were done in quadruplicates at 95° C. 10 min and 95° C. 3 s, 60° C. 30 s for 45 cycles in an optical 384-well plate. The sequences of the primers and probes and SEQ ID NO used in each analysis (A, B, F, G, H) are provided in Table 5.

TABLE 5

Analysis A

Forward Primer CATCCCAATTGCCCTTTCC (SEQ ID NO: 66)

Reverse Primer CCCACACCTGCTCTTGCTAGA (SEQ ID NO: 67)

Probe TCTAGGTGGAAAGTGGG (SEQ ID NO: 68)

TABLE 5-continued

Analysis B

Forward Primer GAGCAGGTGTGGGTTTAGGA (SEQ ID NO: 69)

Reverse Primer CCAGGTCTCACTGCATTCCA (SEQ ID NO: 70)

Probe ATTGCAAGCGTTCGGATAATGTGAGA (SEQ ID NO: 71)

Analysis D

Forward Primer GCTGTCACGAAGGCTTTCTTC (SEQ ID NO: 72)

Reverse Primer GCACTGCTGCCAACTACAAC (SEQ ID NO: 73)

Probe TCAATGCCATCAGCTCACACCTGC (SEQ ID NO: 74)

Analysis G

Forward Primer AAGAGGCGCGGGTAGAA (SEQ ID NO: 75)

Reverse Primer CAGCTTCGGTCAGAGAAATGAG (SEQ ID NO: 76)

Probe CTCTCCTCAGAGCTCGACGCATTT (SEQ ID NO: 77)

Analysis H

Forward Primer CTGCACAATTTCAGCCCAAG (SEQ ID NO: 78)

Reverse Primer CAGGTCATGTCCCACAGAAT (SEQ ID NO: 79)

Probe CATATGAGGGCAGCAATGCAAGTC (SEQ ID NO: 80)

Western Blot Analysis

Differentiated embryoid bodies (EBs) were collected and homogenized in SDS sample buffer (2% SDS, 10% glycerol, 5% βmercaptoethanol, 60 mM TrisHCl, pH 6.8, bromophenol blue). Protein extracts were quantified using the RC DC protein assay (BioRad). Extracts (10 μg) were run on a 4-20% SDS-PAGE gel (ThermoFisher) and transferred onto nitrocellulose membrane using an iBLOT transfer unit (ThermoFisher). Immunoblots were probed with primary antibodies against C9orf72 and GAPDH (Millipore). Bound antibody was detected by incubation with secondary antibodies conjugated to horseradish peroxidase (Abcam) followed by chemiluminescence using a SuperSignal West Pico chemiluminescent substrate (Thermo Scientific). Signal was detected by autoradiography using Full Speed Blue sensitive medical X-Ray film (Ewen Parker XRay Corporation). Relative protein levels were calculated using ImageJ.

Fluorescent in situ Hybridization (FISH) and Immunofluorescence (IF) for the Detection of RNA and Translation Products Fluorescent in situ hybridization (FISH) and immunofluorescence were respectively used to determine the location of RNA transcribed from the hexanucleotide repeat sequence set forth as SEQ ID NO:1, as well as dipeptide repeat proteins translated therefrom, in embryonic stem cell-derived motor neurons (ESMNs) generated as described in Example 3. Briefly, ESMNs were grown in four-well chamber slide (Lab-Tek II chamber slide system, ThermoFisher Scientific) and fixed with 4% PFA (Electron Microscopy Sciences) in PBS. Cells were then permeabilized with diethyl pyrocarbonate (DEPC) PBS/0.2% Triton X-100 (Fisher Scientific, catalog #BP151) and washed with DEPC-PBS, blocked and stained with LNA or DNA oligonucleotides for the detection of RNA transcription products, or anti-polyGA antibody for the detection of RAN translation products, as described below. After staining, slides were subsequently incubated with an appropriate fluorescent dye, mounted with Fluoromount G (Southern Biotech) and visualized using confocal microscopy.

Detection of Sense or Antisense RNA Transcription Products

Slides were pre-hybridized with buffer consisting of 50% formamide (IBI Scientific, catalog #IB72020), DEPC 2× SSC [300 mM sodium chloride, 30 mM sodium citrate (pH 7.0)], 10% (w/v) dextran sulfate (Sigma-Aldrich, catalog #D8960), and DEPC 50 mM sodium phosphate (pH 7.0) for 30 min at 66° C. (for LNA probes) or 55° C. (for DNA probes). The hybridization buffer was then drained off, and 400 µl of 40 nM LNA probe mix or 200 ng/ml of DNA probe mix in hybridization buffer was added to each of the slides and incubated in the dark for 3 hours at 66° C. (for LNA probes) or 55° C. (for DNA probes). Slides incubated with LNA probes were rinsed once in DEPC 2× SSC/0.1% Tween 20 (Fisher Scientific, catalog no. BP337) at room temperature and in DEPC 0.1× SSC three times at 65° C. Slides incubated with DNA probes washed three times with 40% formamide in 2× SSC and briefly washed one time in PBS. Slides were subsequently incubated with 1 µg/mL DAPI (Molecular Probes Inc.).

The sequences and SEQ ID NOs: of the LNA and DNA oligonucleotide probes used in this example, as well as the hybridization conditions of the probes, are provided in Table 6 below.

shows that, similar to the neuronal tissues isolated from the mice comprising 3 or 92 repeats of the heterologous hexanucleotide sequence set forth as SEQ ID NO:1 at the endogenous C9orf72 locus and ESMNs comprising the same, C9orf72 expression was also enhanced in non-neuronal tissues, e.g., muscle and heart, in mice comprising 3 or 92 repeats of the heterologous hexanucleotide sequence set forth as SEQ ID NO:1 at the endogenous C9orf72 locus. Furthermore, the enhancement was specific for the humanized C9orf72 allele; no enhanced expression of the mouse C9orf72 allele, which does not contain the repeat sequence, was seen in heterozygous mice (data not shown).

Preliminary calculations indicate that ESMNs or brain cells with thirty or ninety-two repeats of the hexanucleotide sequence set forth as SEQ ID NO:1 have approximately 17 copies of a C9orf72 mRNA per cell, consistent with the findings of Liu et al. (2017) supra. An increased number of repeats of a hexanucleotide sequence set forth in SEQ ID NO:1 is also directly correlated with an increase in C9orf72 protein levels, (FIGS. 7 and 8), nuclear and cytoplasmic accumulation of sense and antisense C9orf72 RNA foci (FIGS. 9A and 9B), and dipeptide repeat proteins (FIG. 10). The data shown herein indicate that increased number of repeats of a hexanucleotide sequence set forth in SEQ ID NO:1 at the C9orf72 locus results in cells exhibiting a molecular phenotype (e.g., increased transcription, accumulation of RNA foci, and/or increased dipeptide repeat proteins) similar to human cells isolated from patients diag-

TABLE 6

| Probe | Sequence (SEQ ID NO:) | Hybridization method |
|---|---|---|
| LNA sense $G_4C_2$ RNA | TYE563-CCCCGGCCCCGGCCCC (SEQ ID NO: 81) | 66° C. hybridization and washes in 0.1 X SSC |
| LNA antisense $G_4C_2$ RNA | TYE563-GGGGCCGGGGCCGGGG GGCCCC (SEQ ID NO: 82) | 66° C. hybridization and washes in 0.1 X SSC |
| DNA sense $G_4C_2$ RNA | CCCCGGCCCCGGCCCCGG-Cy3 (SEQ ID NO: 83) | 55° C. hybridization and washes in 2 X SSC |
| DNA antisense $G_4C_2$ RNA | GGGGCCGGGGCCGGGGC-Cy3 (SEQ ID NO: 84) | 55° C. hybridization and washes in 2 X SSC |

Detection of Dipeptide Repeat Protein Products

After permeabilization, slides were blocked with 5% normal donkey serum diluted in Tris buffered saline (pH 7.4) with 0.2% Triton ×100 (TBS-T). Slides were incubated overnight at 4° C. with primary antibodies against poly-GA (Millipore) diluted in TBS-T with 5% normal donkey. After washing 3 time with TBS-T, slides were incubated with species specific secondary antibodies coupled to Alexa 488 or 555 (1:1000 in TBS-T, ThermoFisher) and DAPI (1 µg/ml) (Molecular Probes Inc.) for 1 hr at room temperature. After washing 3 times with TBS-T slides were mounted with Fluoromount G (Southern Biotech) and visualized using confocal microscopy.

Results

As shown in FIGS. 4, 5 and 6, ESMNs, total brain and neuronal tissues from mice comprising the hexanucleotide repeat expansion sequence set forth as SEQ ID NO:1 at the C9orf72 locus showed increased expression of the C9orf72 mRNA transcripts. Such increase appears to be correlated with the number of the hexanucleotide repeats present between exons 1a and 1b of the C9orf72 locus. FIG. 6 also nosed with ALS, and supports the use of the non-human animals disclosed herein as a disease model for neurodegenerative disease.

Example 4

Behavioral Analysis of Non-human Animals having a Heterologous Hexanucleotide Repeat Expansion Sequence in an Endogenous C9orf72 Locus This example describes behavioral analysis of non-human animals (e.g., rodents) described herein for ALS-like symptoms such as, for example, decreased body weight and/or significant motor abnormalities resulting from an insertion of a heterologous hexanucleotide repeat expansion sequence in an endogenous rodent (e.g., mouse) C9orf72 locus as described in Example 1.

Phenotypic studies of mice having an a pathogenic heterologous hexanucleotide repeat expansion sequence inserted into an endogenous C9orf72 locus as described above, and/or control mice, e.g., wildtype mice or mice having an a non-pathogenic heterologous hexanucleotide repeat expansion sequence inserted into an endogenous C9orf72 locus as described above, is performed at 8, 18, 37 (female) and 57-60 weeks (male). Body weight is measured on a bi-weekly basis, and body composition is analyzed by µCT scan (Dynamic 60). Standard 24 scan is used to visualize mass of the cervical region of the spine. All animal procedures were conducted in compliance with protocols approved by the Regeneron Pharmaceuticals Institutional Animal Care and Use Committee.

Assessment of overall motor function is performed using blinded subjective scoring assays. Analysis of motor impairment is conducted using rotarod, open field locomotor, and catwalk testing. Motor impairment score is measure using the system developed by the ALS Therapy Development Institute (ALSTDI, Gill A. et al., 2009, PLoS One 4:e6489). During catwalk testing, subjects walk across an illuminated glass platform while a video camera records from below. Gait related parameters such as stride pattern, individual paw swing speed, stance duration, and pressure are reported for each animal. This test is used to phenotype mice and evaluate novel chemical entities for their effect on motor performance. CatWalk XT is a system for quantitative assessment of footfalls and gait in rats and mice. It is used to evaluate the locomotor ability of rodents in almost any kind of experimental model of central nervous, peripheral nervous, muscular, or skeletal abnormality.

CatWalk Gait Analysis: Animals are placed at the beginning of the runway of Noldus CatWalk XT 10, with the open end in front of them. Mice spontaneously run to the end of the runway to attempt to escape. The camera records and the software of the system measures the footprints. The footprints are analyzed for abnormalities in paw placement.

Open Field Test: Mice are placed in the Kinder Scientific open field system and evaluated for 60 minutes. The apparatus uses infrared beams and computer software to calculate fine movements, X+Y ambulation, distance traveled, number of rearing events, time spent rearing, and immobility time.

Rotorod: The rotorod test (IITC Life Science, Woodland Hills, Calif.) measures the latency for a mouse to fall from a rotating beam. The rotorod is set to the experimental regime that starts at 1 rpm and accelerates up to 15 rpm over 180 seconds. Then, the animals' latency to fall following the incremental regime is recorded. The average and maximum of the three longest durations of time that the animals stay on the beam without falling off are used to evaluate falling latency. Animals that manage to stay on the beam longer than 180 seconds are deemed to be asymptomatic.

Upper motor neuron impairment presents as spasticity (i.e., rigidity), increased reflexes, tremor, bradykinesia, and Babinski signs. Lower motor neuron impairment presents as muscle weakness, wasting, clasping, curling and dragging of feet, and fasciculations. Bulbar impairment presents as difficulty swallowing, slurring and tongue fasciculations. Overall motor function is also assessed starting at 32 weeks up to 60 weeks of age as percent of living animals at a given week. Mice are weighed weekly and assessment of overall motor function is performed using blinded subjective scoring assays (as described above). Weekly or bi-monthly clinical neurological exams are performed on the two groups of mice looking at their motor impairment, tremor and rigidity of their hind limb muscles. For motor impairment, a blinded neurological scoring scale from of zero (no symptoms) to four (mouse cannot right themselves within 30 seconds of being placed on their side) is used as shown in Table 7.

TABLE 7

ALS-TDI neurological scoring system

| | |
|---|---|
| Score of 0: | Full extension of hind legs away from lateral midline when mouse is suspended by its tail, and mouse can hold this for two seconds, suspended two to three times. |
| Score of 1: | Collapse or partial collapse of leg extension towards lateral midline (weakness) or trembling of hind legs during tail suspension. |
| Score of 2: | Toes curl under at least twice during walking of 12 inches, or any part of foot is dragging along cage bottom/table. |
| Score of 3: | Rigid paralysis or minimal joint movement, foot not being used for generating forward motion. |
| Score of 4: | Mouse cannot right itself within 30 seconds after being placed on either side. |

For tremor and rigidity, a scoring system with a scale from zero (no symptoms) to three (severe) is used. Table 8 sets forth the scoring methodology related to motor impairment, tremor and rigidity of animals during testing.

TABLE 8

| | 0 | 1 | 2 | 3 |
|---|---|---|---|---|
| Motor impairment | no phenotype | clasping | clasping & dragging | Paralysis |
| Tremor | none | mild | moderate | Severe |
| Rigidity | none | mild | moderate | Severe |

In another experiment mice are examined using a grip strength test. Briefly, the grip strength measures the neuromuscular function as maximal muscle strength of forelimbs, and is assessed by the grasping applied by a mouse on a grid that is connected to a sensor. All grip strength values obtained are normalized against mouse body weight.

In another experiment, the lumbar portion of spinal cords from control mice and mice comprising a pathogenic heterologous hexanucleotide repeat expansion sequence inserted into an endogenous C9orf72 locus at around 60 weeks old are collected for histopathological analysis. The total number of motor neurons in the spinal cords, and mean cell body area of motor neurons are observed in both test and control cohorts.

The thermal nociception of control mice, and test mice comprising an insertion of a pathogenic heterologous hexanucleotide repeat expansion sequence at 20 weeks of age is tested by placing animals on a metal surface maintained at 48° C., 52° C. or 55° C. (IITC, Woodland Hills, Calif.). Latency to respond, defined as the time elapsed until the animal licked of flicked a hind paw, to the heat stimulus is measured. Mice remain on the plate until they performed either of two nocifensive behaviors: hindpaw licking or hindpaw shaking.

Example 5

Deletion of a Heterologous Hexanucleotide Repeat Expansion Sequence from an endogenous non-human C9ORF72 locus in a non-human embryonic stem cell using a CRISPR/Cas9 system Potential guide RNA (gRNA) sequences for a reference hexanucleotide repeat expansion sequence (comprising at least one, at least about three, at least about five, at least about fifteen, at least about twenty, at least about thirty, at least about forty, at least about fifty, at least about 60 at least about 70, at least about 80, or at least about 90, preferably contiguous, repeats of the hexanucleotide sequence set forth as SEQ ID NO:1) are analyzed and scored. DNA encoding potentially effective gRNA (e.g., crRNA and/or tracRNA) is synthesized and placed into an expression construct, which may also comprise a nucleic acid encoding a Cas protein. See, e.g., FIG. 12. ES cells comprising the reference hexanucleotide repeat expansion sequence are transfected with the expression construct (s) comprising the DNA encoding the gRNA and/or Cas protein, and a drug resistance gene. Drug—resistant clones are obtained by serial dilution, expanded for analysis and frozen. DNA from each drug-resistant ES cell clone is isolated and analyzed by PCR and visualization on an agarose gel. PCR products of a correct size are extracted and further sequenced to confirm deletion of the targeted hexanucleotide repeat expansion sequence.

FIG. 11 provides a not to scale depiction of a non-limiting exemplary reference hexanucleotide repeat expansion sequence, e.g., as found in 8029 A-A6 ES cells generated in Example 1, e.g., having a sequence as set forth as SEQ ID NO:45, and the positions of which that were more likely to be successfully targeted by gRNA. The DNA sequences encoding crRNA that target the positions depicted in FIG. 11, an exemplary sequence for which is provided as SEQ ID NO:45, and the SEQ ID NO: of each are provided in Table 9. Notably, the sequences set forth as SEQ ID NOs:46-50 contain an initial guanine not found in the reference hexanucleotide repeat expansion sequence set forth as SEQ ID NO: 45 for optimal expression with a U6 promoter.

TABLE 9

Designed gRNA sequences

| Position in SEQ ID NO: 45 | crRNA encoding sequence (SEQ ID NO:) |
|---|---|
| 190 | GCTACTTGCTCTCACAGTACT (SEQ ID ON: 46) |
| 196 | GCTCTCACAGTACTCGCTGA (SEQ ID NO: 39) |

TABLE 9-continued

Designed gRNA sequences

| Position in SEQ ID NO: 45 | crRNA encoding sequence (SEQ ID NO:) |
|---|---|
| 274 | GCCGCAGCCTGTAGCAAGCTC (SEQ ID NO: 47) |
| 899 | GCGGCCGCTAGCGCGATCGCG (SEQ ID NO: 48) |
| 905 | GCTAGCGCGATCGCGGGGCG (SEQ ID NO: 49) |
| 1006 | GTGGCGAGTGGGTGAGTGAGG (SEQ ID NO: 50) |
| 1068 | GGAAGAGGCGCGGGTAGAAG (SEQ ID NO: 44) |

DNA encoding the crRNA as set forth in Table 9 were made (Integrated DNA Technologies) and inserted into an expression construct in operable linkage with DNA encoding tracrRNA (e.g., DNA comprising the sequence set forth as SEQ ID NO: 63). Successful ligation of the crRNA encoding sequences, was confirmed by polymerase chain reaction with the vector screening primers set forth in Table 10, and the sequences of the gRNA (crRNA and tracrRNA) encoding sequences were confirmed with sequence analysis using the vector sequencing primers, also set forth in Table 10. Expression constructs comprising the correct gRNA encoding sequences under the control of a U6 promoter, a nucleic acid encoding a cas9 protein, and a puromycin resistance gene, FIG. 12, were amplified and purified.

TABLE 10

| Vector Screening forward primer Position 190 gRNA | ACACCGCTCTCACAGTACTCGCTGAG (SEQ ID NO: 51) |
|---|---|
| Vector Screening forward primer Position 196 gRNA | ACACCGCCGCAGCCTGTAGCAAGCTCG (SEQ ID NO: 52) |
| Vector Screening forward primer Position 274 gRNA | ACACCGAGTACTGTGAGAGCAAGTAGG (SEQ ID NO: 53) |
| Vector Screening forward primer Position 899 gRNA | ACACCGACGCCCCGCGATCGCGCTAGG (SEQ ID NO: 54) |
| Vector Screening forward primer Position 905 gRNA | ACACCGCGGCCGCTAGCGCGATCGCGG (SEQ ID NO: 55) |
| Vector Screening forward primer Position 1006 gRNA | ACACCGTGGCGAGTGGGTGAGTGAGGG (SEQ ID NO: 56) |
| Vector Screening forward primer Position 1068 gRNA | ACACCGGAAGAGGCGCGGGTAGAAGG (SEQ ID NO: 57) |
| Vector Screening reverse primer All gRNA | GACGCGTTAATGCCAACTTT (SEQ ID NO: 58) |
| Vector sequencing forward primer | GAGGGCCTATTTCCCATGAT (SEQ ID NO: 59) |
| Vector sequencing reverse primer | GACGCGTTAATGCCAACTTT (SEQ ID NO: 60) |

TABLE 10-continued

| | |
|---|---|
| Clone screening forward primer | GAACTTACGGAGTCCCACGA (SEQ ID NO: 61) |
| Clone screening reverse primer | GGAGACAGCTCGGGTACTGA (SEQ ID NO: 62) |

8029 A-A6 clones as obtained in Example 1 and comprising a hexanucleotide repeat expansion sequence comprising about 92 repeats of the hexanucleotide sequence set forth as SEQ ID NO: 1 (e.g., a reference sequence set forth as SEQ ID NO: 45) were transfected with different combinations of the crRNA set forth in Table 9 (plus tracrRNA sequence), a puromycin resistance gene, and a CRISPR/Cas9 endonuclease gene. In one combination, ES cells were transfected with a CRISPR/Cas9 system targeting sequences starting at positions 190, 196, 274, 899, 905, 1006, and 1068 of SEQ ID NO: 45 (e.g., the expression construct(s) comprising a nucleic acid encoding cas9 protein and/or gRNA inserts having the sequences set forth as SEQ ID NOs: 39, 44 and 46-50. In a second combination, ES cells were transfected a CRISPR/Cas9 system targeting positions 196, 1006 and 1067 of SEQ ID NO: 45 (e.g., the expression construct(s) comprising a nucleic acid encoding cas9 protein and/or DNA encoding gRNA inserts comprising the sequence set forth as SEQ ID NOs: 39, 50 and 44, respectively). In a third combination, ES cells were transfected with gRNA inserts targeting positions 196, 272 and 1005 and 1067 of SEQ ID NO: 45 (e.g., the expression construct(s) comprising a nucleic acid encoding cas9 protein and/or gRNA inserts comprising a sequence set forth as SEQ ID NO: 39, 47, 50 and 44, respectively).

Puromycin-resistant ES clones were obtained by serial dilution, cultured in media (500 ml KO DMEM media, 95ml Heat Inactivated FBS, 12mL L-Glutamine, 6mL Penn-Step, 6mL Non-Essential Amino Acids, 1.2mL B-mercaptoethonal), expanded for analysis, and frozen. DNA from each clone was isolated using the DNAase Blood and Tissue Kit according to the manufacturer's protocol (Qiagen) and analyzed by PCR using the clone screening forward and reverse screening primers set forth in Table 10. PCR products were visualized by agarose gel electrophoresis, and PCR products of a correct size were extracted and further sequenced to confirm deletion of the targeted hexanucleotide repeat expansion sequence.

Of one-hundred sixty (160) clones, one hundred clones were tested and eleven (11) demonstrated a deletion of the hexanucleotide repeat expansion sequence, e.g. as demonstrated an amplified PCR product between 300 and 700 base pairs (data not shown). Sequence analysis confirmed deletion of the hexanucleotide repeat expansion sequence (data not shown). Of the three combinations tested, a CRISPR/Cas system targeting the combination of positions 196, 1005 and 1067 of SEQ ID NO: 45 proved most efficient in deleting the hexanucleotide repeat expansion sequence; this combination resulted in ten of the eleven positive clones. A CRISPR/Cas system targeting the combination of positions 196, 272. 1005 and 1067 of SEQ ID NO: 45 provided one clone.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

We claim:

1. A rodent comprising a hexanucleotide repeat expansion sequence at an endogenous C9orf72 locus, wherein the hexanucleotide repeat expansion sequence
   (i) comprises at least one repeat of the hexanucleotide sequence set forth as SEQ ID NO: 1,
   (ii) is in operable linkage to an endogenous C9orf72 regulatory sequence, and
   (iii) is expressed from an endogenous C9orf72 promoter.

2. The rodent of claim 1, wherein the hexanucleotide repeat expansion sequence comprises at least at thirty repeats of the hexanucleotide sequence set forth as SEQ ID NO:1.

3. The rodent of claim 1, wherein the hexanucleotide repeat expansion comprises at least 90 repeats of the hexanucleotide sequence set forth as SEQ ID NO:1.

4. The rodent of claim 1, wherein the rodent exhibits (i) increased expression of C9orf72 transcripts compared to a control rodent comprising a wildtype C9orf72 locus, (ii) an increased number of RNA foci compared to a control rodent comprising a wildtype C9orf72 locus, (iii) an increased level of dipeptide repeat proteins compared to a control rodent comprising a wildtype C9orf72 locus, or (iv) any combination of (i)-(iii).

5. The rodent of claim 1, wherein the hexanucleotide repeat expansion sequence comprises from 5' to 3': a first hexanucleotide flanking sequence, contiguous repeats of the hexanucleotide sequence set forth as SEQ ID NO: 1, and a second hexanucleotide flanking sequence,
   wherein at least a portion of the non-coding sequence encompassing exon 1 and the ATG start codon of the endogenous C9orf72 locus is replaced with the hexanucleotide repeat expansion sequence.

6. The rodent of claim 5, wherein the first hexanucleotide flanking sequence comprises the sequence set forth as SEQ ID NO: 36 and the second hexanucleotide flanking sequence comprises the sequence set forth as SEQ ID NO: 37.

7. The rodent of claim 5, wherein the hexanucleotide repeat expansion sequence comprises a sequence set forth as SEQ ID NO: 2, SEQ ID NO:3, or variants thereof.

8. The rodent of claim 1, wherein the rodent is a rat or a mouse.

9. The rodent of claim 8, wherein the rodent is a mouse, wherein the endogenous C9orf72 locus comprises from 5' to 3':
   (i) a mouse C9orf72 sequence comprising the sequence set forth as SEQ ID NO:20 or SEQ ID NO:23,
   (ii) a heterologous repeat expansion sequence comprising a sequence set forth as SEQ ID NO:2, SEQ ID NO:3, or variants thereof,
   (iii) a mouse C9orf72 sequence comprising the sequence set forth as SEQ ID NO:22 or SEQ ID NO:25, and (iv) mouse C9orf72 coding exons, and
wherein the mouse exhibits all of the following three characteristics (i) increased expression of C9orf72 transcripts compared to a control animal comprising a wildtype C9orf72 locus, (ii) an increased number of RNA foci compared to a control animal comprising a wildtype C9orf72 locus, and (iii) an increased level of dipeptide repeat proteins compared to a control animal comprising a wildtype C9orf72 locus.

10. The rodent of claim 1, wherein the rodent is homozygous for the hexanucleotide repeat expansion sequence.

11. The rodent of claim 1, wherein the non-human animal is heterozygous for the hexanucleotide repeat expansion sequence.

12. The rodent of claim 11, wherein the hexanucleotide repeat expansion sequence is a first hexanucleotide expansion sequence, wherein the rodent is also heterozygous for a second hexanucleotide repeat expansion sequence, and wherein the first expansion sequence has a different number of repeats than the second hexanucleotide repeat expansion sequence.

13. The rodent of claim 12, wherein the first repeat expansion sequence comprises one to three repeats of the hexanucleotide sequence set forth as SEQ ID NO:1 and the second repeat expansion sequence comprises four to one hundred repeats of the hexanucleotide sequence set forth as SEQ ID NO:1.

14. A method of identifying a therapeutic candidate for the treatment of a disease or condition associated with the presence of a hexanucleotide repeat expansion sequence, the method comprising
(a) administering a candidate agent to a rodent or a rodent cell comprising a hexanucleotide repeat expansion sequence at an endogenous C9orf72 locus,
wherein the hexanucleotide repeat expansion sequence
(i) comprises at least one repeat of the hexanucleotide sequence set forth as SEQ ID NO: 1,
(ii) is in operable linkage to an endogenous C9orf72 regulatory sequence, and
(iii) is expressed from an endogenous C9orf72 promoter, and
wherein the rodent or rodent cell exhibits (i) increased expression of C9orf72 transcripts compared to a control rodent or rodent cell comprising a wildtype C9orf72 locus, (ii) an increased number of RNA foci compared to a control rodent or rodent cell comprising a wildtype C9orf72 locus, (iii) an increased level of dipeptide repeat proteins compared to a control rodent or rodent cell comprising a wildtype C9orf72 locus, or (iv) any combination of (i)-(iii);
(b) performing one or more assays to measure the level of a C9orf72 gene product expressed by the rodent or rodent cell derived therefrom, wherein the C9orf72 gene product is selected from the group consisting of sense C9orf72 RNA, antisense C9orf72 RNA, RNA foci comprising C9orf72 sense or antisense RNA, and dipeptide repeat proteins; and
(c) identifying the candidate agent that has an effect on the level of a C9orf72 gene product selected from the group consisting of sense C9orf72 RNA, antisense C9orf72 RNA, RNA foci comprising C9orf72 sense or antisense RNA, and dipeptide repeat proteins expressed by the rodent or rodent cell as the therapeutic candidate.

15. The method of claim 14, wherein the candidate agent is administered in vivo to a rodent or rodent cell, and optionally, the assay is performed in vitro on tissue isolated from the rodent or rodent cell after administration of the candidate agent.

16. The method of claim 14, wherein the candidate agent is administered in vitro to a rodent embryonic stem cell-derived motor neuron.

17. The method of claim 14, wherein the assay is quantitative polymerase chain reaction (qPCR) to detect C9orf72 gene products.

18. The method of claim 17, wherein qPCR is performed with a primer and/or probe having a nucleotide sequence set forth in SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, or any combination thereof.

19. The method of claim 14, wherein the assay is measures RNA foci comprising a C9orf72 sense or antisense RNA transcripts.

20. The method of claim 19, wherein the assay is fluorescent in situ hybridization using one or more probes having a nucleotide sequence as set forth in any one of SEQ ID NO:81, SEQ ID NO:82, SEQ ID NO:83, and/or SEQ ID NO:84.

21. The method of claim 14, wherein the assay is measures polyGA dipeptide repeat proteins.

22. A rodent cell comprising a hexanucleotide repeat expansion sequence at an endogenous C9orf72 locus,
wherein the hexanucleotide repeat expansion sequence
(i) comprises at least one repeat of the hexanucleotide sequence set forth as SEQ ID NO: 1,
(ii) is in operable linkage to an endogenous C9orf72 regulatory sequence, and
(iii) is expressed from an endogenous C9orf72 promoter.

23. The rodent cell of claim 22, wherein the non-human animal cell is an embryonic stem cell, an embryonic stem cell-derived motor neuron, a brain cell, a cortical cell, a neuronal cell, a muscle cell, a heart cell, or a germ cell.

24. An immortalized cell line or motor neuron derived from the embryonic stem cell of claim 23.

25. The rodent cell of claim 22, wherein the hexanucleotide repeat expansion sequence comprises at least at thirty repeats of the hexanucleotide sequence set forth as SEQ ID NO:1.

26. The rodent cell of claim 22, wherein the hexanucleotide repeat expansion sequence comprises at least 90 repeats of the hexanucleotide sequence set forth as SEQ ID NO:1.

27. The rodent cell of claim 22, wherein the rodent cell exhibits (i) increased expression of C9orf72 transcripts compared to a control rodent cell comprising a wildtype C9orf72 locus, (ii) an increased number of RNA foci compared to a control rodent cell comprising a wildtype C9orf72 locus, (iii) an increased level of dipeptide repeat proteins compared to a control rodent cell comprising a wildtype C9orf72 locus, or (iv) any combination of (i)-(iii).

28. The rodent cell of claim 22, wherein the hexanucleotide repeat expansion sequence comprises from 5' to 3': a first hexanucleotide flanking sequence, contiguous repeats of the hexanucleotide sequence set forth as SEQ ID NO: 1, and a second hexanucleotide flanking sequence,
wherein at least a portion of the non-coding sequence encompassing exon 1 and the ATG start codon of the endogenous C9orf72 locus is replaced with the hexanucleotide repeat expansion sequence.

29. The rodent cell of claim 28, wherein the first hexanucleotide flanking sequence comprises the sequence set forth as SEQ ID NO: 36 and the second hexanucleotide flanking sequence comprises the sequence set forth as SEQ ID NO: 37.

30. The rodent cell of claim 28, wherein the hexanucleotide repeat expansion sequence comprises a sequence set forth as SEQ ID NO: 2, SEQ ID NO:3, or variants thereof.

31. The rodent cell of claim 22, wherein the rodent cell is a rat cell or a mouse cell.

32. The rodent cell of claim 31, wherein the rodent cell is a mouse cell,
wherein the endogenous C9orf72 locus comprises from 5' to 3':
(i) a mouse C9orf72 sequence comprising the sequence set forth as SEQ ID NO:20 or SEQ ID NO:23,
(ii) a heterologous repeat expansion sequence comprising a sequence set forth as SEQ ID NO:2, SEQ ID NO:3, or variants thereof,
(iii) a mouse C9orf72 sequence comprising the sequence set forth as SEQ ID NO:22 or SEQ ID NO:25, and
(iv) mouse C9orf72 coding exons, and
wherein the mouse cell exhibits all of the following three characteristics (i) increased expression of C9orf72 transcripts compared to a control animal comprising a wildtype C9orf72 locus, (ii) an increased number of RNA foci compared to a control animal comprising a wildtype C9orf72 locus, and (iii) an increased level of dipeptide repeat proteins compared to a control animal comprising a wildtype C9orf72 locus.

33. A rodent embryonic stem cell whose genome comprises a hexanucleotide repeat expansion sequence at an endogenous C9orf72 locus,
wherein the hexanucleotide repeat expansion sequence
(i) comprises at least one repeat of the hexanucleotide sequence set forth as SEQ ID NO: 1,
(ii) is in operable linkage to an endogenous C9orf72 regulatory sequence, and
(iii) is expressed from an endogenous C9orf72 promoter.

34. A rodent embryo generated from the embryonic stem cell of claim 33.

35. A method of making a rodent whose genome comprises a hexanucleotide sequence, the method comprising
modifying the genome of the rodent so that it comprises a hexanucleotide repeat expansion sequence in an endogenous C9orf72 locus, and in operable linkage to an endogenous regulatory sequence, wherein the hexanucleotide repeat expansion sequence comprises at least one repeat of the hexanucleotide sequence set forth as SEQ ID NO: 1, and
wherein the hexanucleotide repeat expansion sequence is expressed from an endogenous C9orf72 promoter.

36. The method of claim 35, wherein the modifying is achieved by a process comprising
(a) introducing into a rodent embryonic stem cell a nucleic acid construct comprising an insert nucleic acid, wherein the insert nucleic acid comprises from 5' to 3' (i) a 5' homology arm that is homologous to a 5' target sequence of the C9orf72 locus, (ii) a hexanucleotide repeat expansion sequence, and (iii) a 3' homology arm that is homologous to a 5' target sequence of the C9orf72 locus;
(b) obtaining a genetically modified rodent embryonic stem cell from (a); and
(c) creating a rodent using the genetically modified rodent embryonic stem cell of (b).

37. The method of claim 36, wherein the insert nucleic acid further comprises between the 5' and 3' homology arms one or more genes encoding one or more selection markers.

38. The method of claim 36, wherein the insert nucleic acid further comprises one or more site-specific recombination sites between the 5' and 3' homology arms.

39. The method of claim 38, wherein the insert nucleic acid further comprises between the 5' and 3' homology arms a recombinase gene and a selection marker gene flanked by the recombinase recognition sites, which recombinase recognition sites are oriented to direct an excision.

40. The method of claim 36, wherein the 5' homology arm is identical or substantially identical to exon 1 of the endogenous C9orf72 locus, or a portion thereof.

41. The method of claim 40, wherein the 5' homology arm comprises the nucleotide sequence set forth as SEQ ID NO:20 or SEQ ID NO:23.

42. The method of claim 36, wherein the 3' homology arm is identical or substantially identical to at least a portion of intron 1 of the endogenous C9orf72 locus.

43. The method of claim 42, wherein the 3' homology arm comprises the nucleotide sequence set forth as SEQ ID NO:22 or SEQ ID NO:25.

44. The method of claim 36, wherein the insert nucleic acid comprises a nucleic acid sequence set forth in SEQ ID NO:2 or SEQ ID NO:4.

45. The method of claim 36, wherein the insert nucleic acid comprises a nucleic acid sequence set forth in SEQ ID NO:3 or SEQ ID NO:6.

46. The method of claim 36, further comprising a step of breeding the rodent generated in (c) so that a rodent homozygous for the insertion is created.

47. The method of claim 35, wherein the rodent is a rat or a mouse.

48. A rodent obtainable by the method of claim 35.

* * * * *

UNITED STATES PATENT AND TRADEMARK OFFICE
CERTIFICATE OF CORRECTION

PATENT NO. : 10,781,453 B2
APPLICATION NO. : 15/721517
DATED : September 22, 2020
INVENTOR(S) : David Heslin et al.

It is certified that error appears in the above-identified patent and that said Letters Patent is hereby corrected as shown below:

In the Claims

Column 149, Line 52 "repeat expansion sequence comprises at least at thirty" should read --repeat expansion sequence comprises at least thirty--.

Column 150, Line 54 "SEQ ID NO: 2, SEQ ID NO:3, or variants thereof." should read --SEQ ID NO:2, SEQ ID NO:3, or variants thereof.--.

Column 151, Line 4 "compared to a control animal comprising" should read --compared to a control rodent comprising--.

Column 151, Line 6 "RNA foci compared to a control animal comprising a" should read --RNA foci compared to a control rodent comprising a--.

Column 151, Line 8 "dipeptide repeat proteins compared to a control animal" should read --dipeptide repeat proteins compared to a control rodent--.

Column 151, Line 12 "The rodent of claim 1, wherein the non-human animal" should read --The rodent of claim 1, wherein the rodent--.

Column 151, Line 20 "wherein the first expansion sequence has a" should read --wherein the first hexanucleotide repeat expansion sequence has a--.

Column 151, Lines 23-24 "The rodent of claim 12, wherein the first repeat expansion sequence comprises one to three repeats of the" should read --The rodent of claim 12, wherein the first hexanucleotide repeat expansion sequence comprises one to three repeats of the--.

Column 151, Line 26 "second repeat expansion sequence comprises four to one" should read --second hexanucleotide repeat expansion sequence comprises four to one--.

Signed and Sealed this
Twelfth Day of January, 2021

Andrei Iancu
*Director of the United States Patent and Trademark Office*

CERTIFICATE OF CORRECTION (continued)
U.S. Pat. No. 10,781,453 B2

Column 152, Lines 17-18 "The method of claim 14, wherein the assay is measures" should read --The method of claim 14, wherein the assay measures--.

Column 152, Lines 25-26 "The method of claim 14, wherein the assay is measures" should read --The method of claim 14, wherein the assay measures--.

Column 152, Lines 35-36 "The rodent cell of claim 22, wherein the non-human animal cell" should read --The rodent cell of claim 22, wherein the rodent cell--.

Column 152, Line 42 "repeat expansion sequence comprises at least at thirty" should read --repeat expansion sequence comprises at least thirty--.

Column 153, Line 6 "forth as SEQ ID NO: 2, SEQ ID NO:3, or variants thereof." should read --forth as SEQ ID NO:2, SEQ ID NO:3, or variants thereof.--.

Column 153, Line 24 "compared to a control animal comprising a" should read --compared to a control mouse comprising a--.

Column 153, Line 26 "RNA foci compared to a control animal comprising a" should read --RNA foci compared to a control mouse comprising a--.

Column 153, Line 28 "dipeptide repeat proteins compared to a control animal" should read --dipeptide repeat proteins compared to a control mouse--.